US009974808B2

United States Patent
Bonini et al.

(10) Patent No.: US 9,974,808 B2
(45) Date of Patent: May 22, 2018

(54) USE OF COMMON γ CHAIN CYTOKINES FOR THE VISUALIZATION, ISOLATION AND GENETIC MODIFICATION OF MEMORY T LYMPHOCYTES

(71) Applicant: OSPEDALE SAN RAFFAELE S.R.L., Milan (IT)

(72) Inventors: Maria Chiara Bonini, Peschiera Borromeo (IT); Attilio Bondanza, Peschiera Borromeo (IT)

(73) Assignee: OSPEDALE SAN RAFFAELE S.R.L., Milan (IT)

( * ) Notice: Subject to any disclaimer, the term of this patent is extended or adjusted under 35 U.S.C. 154(b) by 385 days.

(21) Appl. No.: 14/660,484

(22) Filed: Mar. 17, 2015

(65) Prior Publication Data

US 2015/0306142 A1    Oct. 29, 2015

Related U.S. Application Data

(60) Division of application No. 13/240,009, filed on Sep. 22, 2011, now Pat. No. 8,999,715, which is a continuation of application No. 12/063,373, filed as application No. PCT/IT2006/000600 on Aug. 3, 2006, now abandoned.

(60) Provisional application No. 60/706,503, filed on Aug. 8, 2005.

(51) Int. Cl.
| | |
|---|---|
| *A61K 48/00* | (2006.01) |
| *A61K 35/17* | (2015.01) |
| *C12N 5/0783* | (2010.01) |
| *G01N 33/569* | (2006.01) |
| *G01N 33/68* | (2006.01) |
| *A61K 39/00* | (2006.01) |

(52) U.S. Cl.
CPC .......... *A61K 35/17* (2013.01); *A61K 48/0091* (2013.01); *C12N 5/0636* (2013.01); *G01N 33/56972* (2013.01); *G01N 33/6863* (2013.01); *A61K 2039/5156* (2013.01); *C12N 2501/23* (2013.01); *C12N 2501/2302* (2013.01); *C12N 2501/2306* (2013.01); *C12N 2501/2307* (2013.01); *C12N 2501/2315* (2013.01); *C12N 2501/51* (2013.01); *C12N 2501/515* (2013.01); *C12N 2506/11* (2013.01); *C12N 2510/00* (2013.01)

(58) Field of Classification Search
None
See application file for complete search history.

(56) References Cited

U.S. PATENT DOCUMENTS

| | | |
|---|---|---|
| 2005/0074822 A1 | 4/2005 | Nixon et al. |
| 2006/0034810 A1 | 2/2006 | Riley et al. |
| 2006/0121005 A1 | 6/2006 | Berenson et al. |

OTHER PUBLICATIONS

Zhang et al., J Immunol 2005; 174:3051-3058.*
Webster's New World Dictionary, Third College Edition, 1988, see p. 1067.*
McKinney, J Neurol Neurosurg Psychiatry 2004;75(Suppl II):ii12-ii17.*
Geginat, J., et ai, "TCR-independent proliferation and differentiation of human CD4+ T cell subsets induced by cytokines.", Adv Exp Med Biol, vol. 512, 2002, pp. 107-112.
Talayev V. Yu, et al., "Ex vivo stimulation of cord blood mononuclear cells by dexamethasone and interleukin-7 results in the maturation of interferon-gamma-secreting effector memory T cells.", Clin Exp Immunol, vol. 141, No. 3, Jun. 29, 2005 (Jun. 29, 2005), pp. 440-448.
Lynch, D. H., et al., "Interleukin 7 promotes long-term in vitro growth of antitumor cytotoxic T lymphocytes with immunotherapeutic efficacy in vivo.", J Exp Med, vol. 179, No. 1, Jan. 1, 1994 (Jan. 1, 1994), pp. 31-42.
Caccamo, N., et al., "Differential requirements for antigen or homeostatic cytokines for proliferation and differentiation of human Vgamma9Vdelta2 naive, memory and effector T cell subsets.", Eur J Immunol, vol. 35, No. 6, Jun. 2005 (Jun. 2005), pp. 1764-1772.
Berard, M., et al., "IL-15 promotes the survival of naive and memory phenotype CD8+ T cells.", J Immunol, vol. 170, No. 10, May 15, 2003 (May 15, 2003), pp. 5018-5026.
Geginat, J., et al., "Proliferation and differentiation potential of human CD8+ memory T-cell subsets in response to antigen or homeostatic cytokines.", Blood, vol. 101, No. 11, Jun. 1, 2003 (Jun. 1, 2003), pp. 4260-4266.
Zhang, X., et al., "Potent and selective stimulation of memory-phenotype CD8+ T cells in vivo by IL-15.", Immunity, vol. 8, No. 5, May 1998 (May 1998), pp. 591-599.
Kanegane, H., et al., "Activation of naive and memory T cells by interleukin-15.", Blood, vol. 88, No. 1, Jul. 1, 1996 (Jul. 1, 1996), pp. 230-235.
Von Holzen, U., et al., "Selective responsiveness to common gamma chain cytokines in peripheral blood-derived cytotoxic T lymphocytes induced by Melan-A/MART-1(27-35)targeted active specific immunotherapy.", Int J Cancer, vol. 115, No. 2, Jun. 10, 2005 (Jun. 10, 2005), pp. 248-255.
Ho, W. Y., et al., "Adoptive immunotherapy: engineering T cell responses as biologic weapons for tumor mass destruction.", Cancer Cell, vol. 3, No. 5, May 2003 (May 2003), pp. 431-437.
Foster, A. E., et al., "Ex-vivo uses and applications of cytokines for adoptive immunotherapy in cancer.", Curr Pharm Design, vol. 10, No. 11, 2004, pp. 1207-1220.
Bollard, C. M., et al., "Adoptive immunotherapy for post-transplantation viral infections.", Biol Blood Marrow Transpl, vol. 10, No. 3, Mar. 2004 (Mar. 2004), pp. 143-155.
Sprent, J., et al., "Generation and maintenance of memory T cells.", Curr Opin Immunol, vol. 13, No. 2, Apr. 1, 2001 (Apr. 1, 2001), pp. 248-254.
Caserta, S., et al., "IL-7 is superior to IL-2 for ex vivo expansion of tumour-specific CD4+ T-cells.", European Journal of Immunology, vol. 40, 2010, pp. 470-479.

(Continued)

*Primary Examiner* — Zachary S Skelding
(74) *Attorney, Agent, or Firm* — Lucas & Mercanti, LLP

(57) ABSTRACT

It is described in vitro methods for expanding, detecting or isolating rare populations of antigen specific memory T cells. It is also described an in vitro method for obtaining a genetically modified memory T cell population. Uses of cells so obtained are also disclosed.

9 Claims, 40 Drawing Sheets

(56) References Cited

OTHER PUBLICATIONS

Figure 1:
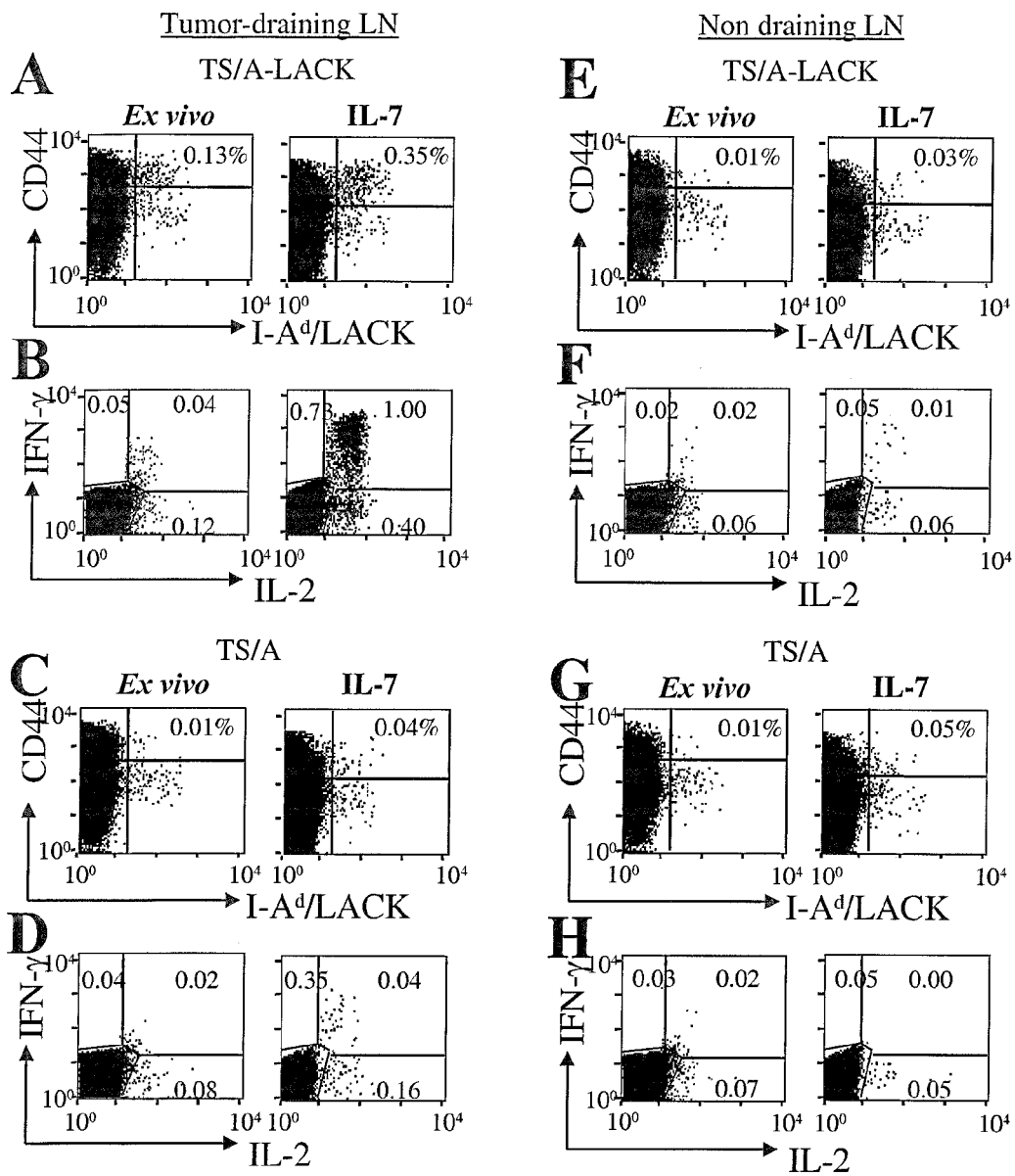

International Search Report issued in PCT/IT2006/000600 dated Mar. 27, 2007.
Whitty, et al, "Small molecule cytokine mimetics", Chem. Biol., Apr. 1999, vol. 6(4), pp. R107-R118.
Sprent, et al., "T cell memory", Annu. Rev. Immunol., 2002, vol. 20, pp. 551-579.
Geginat, et al., "Cytokine-driven proliferation and differentiation of human naive, central memory and effector memory CD4+ T cells", Pathol. Biol., Paris, Mar. 2003, vol. 51(2), pp. 64-66.
Chen, et al., "Ex vivo expansion of dendritic-cell-activated antigen-specific CD4+ T cells with anti-CD3/CD28, interleukin-7, and interleukin-15: potential for adoptive T cell immunotherapy.", Clin Immunol., Apr. 2006, 119(1):21-31.
Pepper, et al., "Origins of CD4(+) effector and central memory T cells.", Nat Immunol., Jun. 2011;12(6):467-471.
Klebanoff, et al., "CD8+ T-cell memory in tumor immunology and immunotherapy.", Immunol Rev., Jun. 2006, 211:214-24.
Berger, et al., "CD28 costimulation and immunoaffinity-based selection efficiently generate primary gene-modified T cells for adoptive immunotherapy.", Blood, Jan. 15, 2003, 101(2):476-484.
Gattinoni, et al., "Acquisition of full effector function in vitro paradoxically impairs the in vivo antitumor efficacy of adoptively transferred CD8+ T cells.", J Clin Invest., Jun. 2005, 115(6):1616-1626.
Kaech, et al., "Selective expression of the interleukin 7 receptor identifies effector CD8 T cells that give rise to long-lived memory cells.", Nat Immunol., Dec. 2003, 4(12):1191-1198.
Huster, et al., "Selective expression of IL-7 receptor on memory T cells identifies early CD40L-dependent generation of distinct CD8+ memory T cell subsets.", Proc Natl Acad Sci., USA, Apr. 13, 2004, 101(15):5610-5615.
Gett, et al., "T cell fitness determined by signal strength.", Nat Immunol., Apr. 2003, 4(4):355-360.
Baron, et al., "The repertoires of circulating human CD8(+) central and effector memory T cell subsets are largely distinct.", Immunity, Feb. 2003, 18(2)193-204.

* cited by examiner

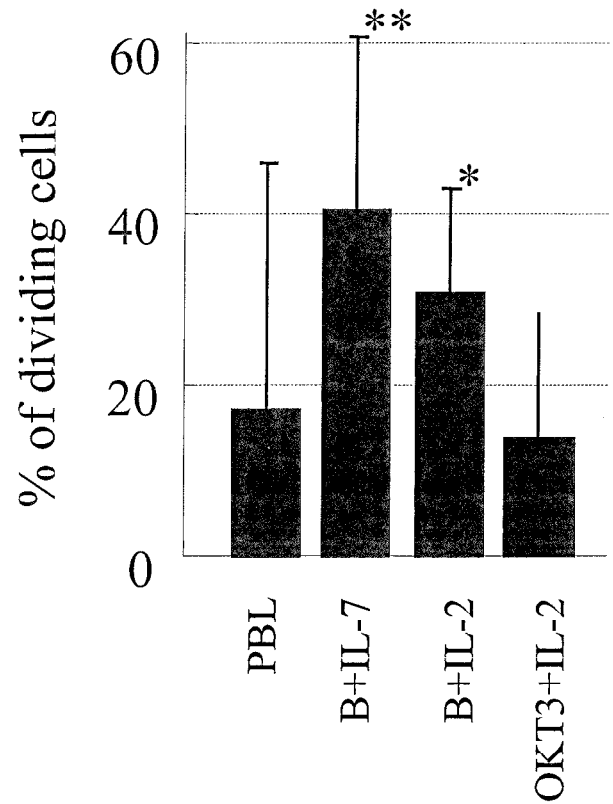
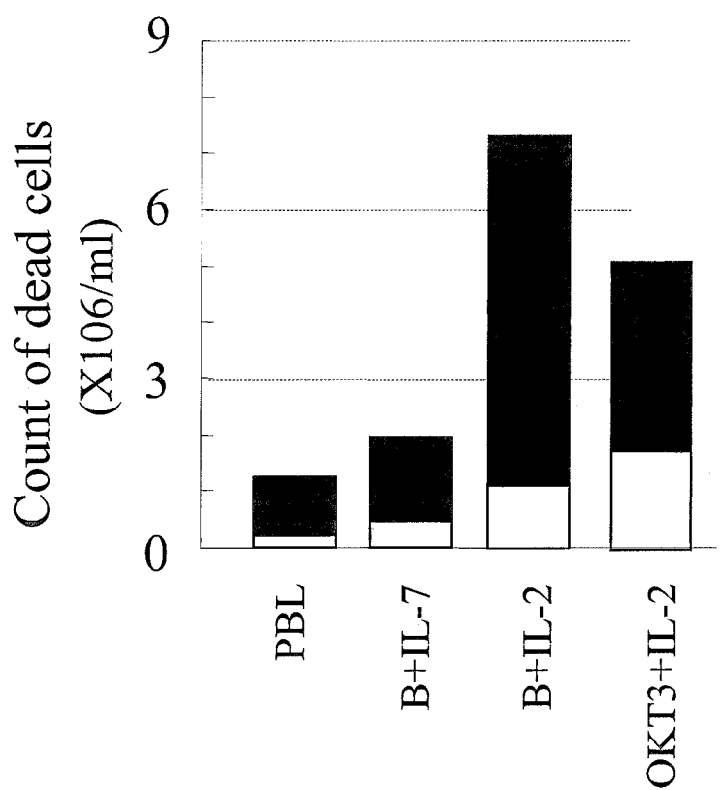
Fig. 35

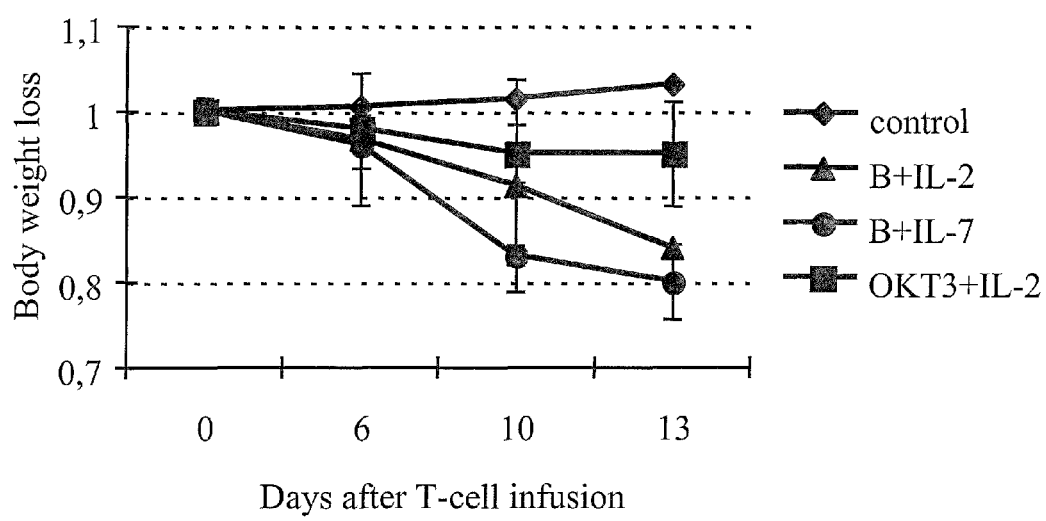
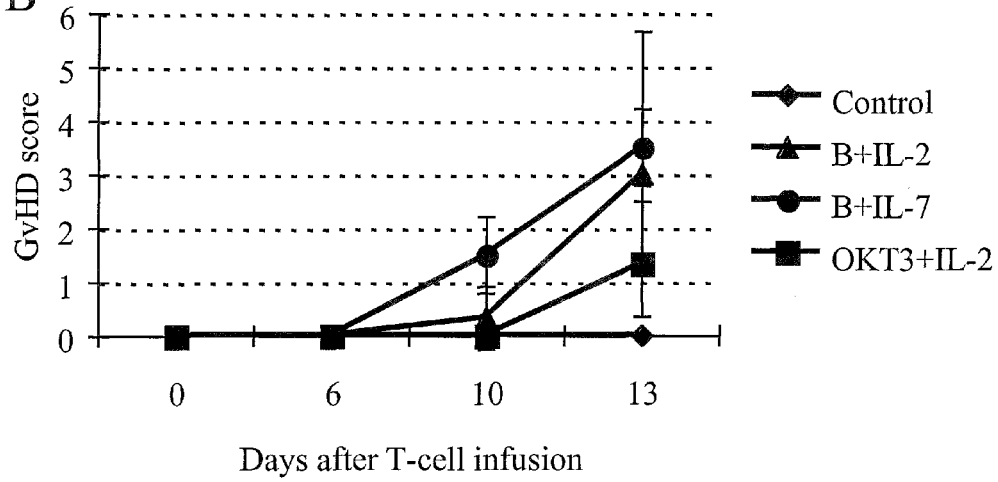
Fig. 38

HE
 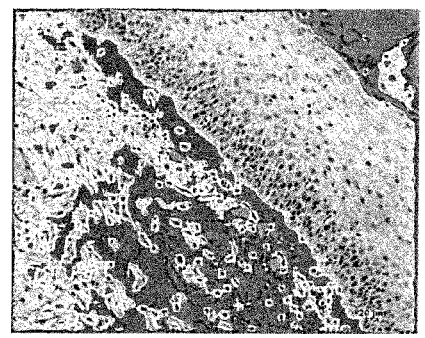
αhCD3
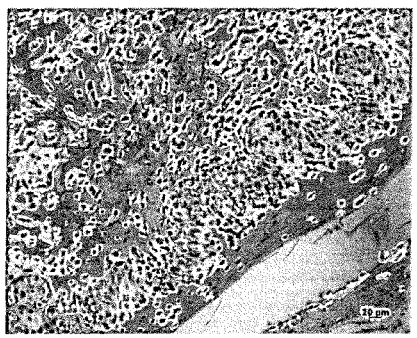 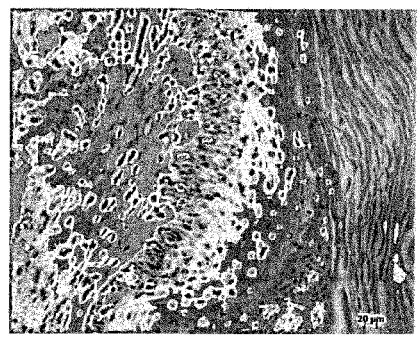
B+IL-7  OKT3+IL-2
Fig. 39

USE OF COMMON γ CHAIN CYTOKINES FOR THE VISUALIZATION, ISOLATION AND GENETIC MODIFICATION OF MEMORY T LYMPHOCYTES

CROSS-REFERENCE TO RELATED APPLICATIONS

This application is a divisional application of U.S. patent application Ser. No. 13/240,009 filed Sep. 22, 2011 which is a continuation application of U.S. patent application Ser. No. 12/063,373 filed Sep. 16, 2008 which is a 371 of PCT Application Serial No. PCT/IT2006/000600 filed Aug. 3, 2006 which claims benefit of U.S. Provisional Application No. 60/705,503 filed Aug. 8, 2005, the contents of each of which are incorporated herein by reference in its entirety.

INTRODUCTION

The repertoire of antigen (Ag)-specific T-cells is tightly regulated by homeostatic mechanisms that ensure their persistence and functionality even in the absence of the antigen. Following Ag encounter, naïve T cells undergo rapid clonal expansion and differentiate into effector T-cells (1, 2). The life-span of effector T-cells is limited by cell death which can occur upon further Ag encounter (activation induced cell death) or due to the lack of survival factors. During an immune response, memory T-cells are also generated. Memory T-cells can survive throughout life, thus providing long-lasting protection against re-call pathogens (3). The frequencies of antigen-specific memory T-cells in most biological samples, however, remain below the limit of detection of Ag/MHC (Major Histocompatibility Complex) tetramer staining and functional assays, such as intracellular cytokine staining and ELISpot (4, 5). Ag-specific $CD4^+$ T cells in particular are mostly undetectable ex vivo and thus analyzed after multiple rounds of in vitro Ag-driven T cell expansion. In vitro re-stimulation however, is likely to favor terminal differentiation of the cells, hampering their long-term survival. As a consequence, in vitro Ag re-stimulated T cells might also exhibit a phenotype not entirely representative of the one found in vivo. For these reasons alternative strategies improving the ex vivo detection of Ag-specific T cells are needed to better characterize ongoing immune responses, and evaluate the immuno-competence of patients with immune-related disorders.

Several studies have shown that the establishment and the maintenance of T cell memory is controlled by cell associated (Ag/MHC complex) and soluble (cytokines) driven signals (3, 6, 7). Triggering of the TCR by self and non self Ag/MHC complexes regulates the transition from naïve to memory cells, the survival and the proliferation of memory cells. The pool of memory lymphocytes is possibly highly heterogeneous. Recently, two types of memory T-cells have been identified: effector memory T-cells (CD45RA−, CCR7−, CD62L−) and central memory T-cells that are CD45RA negative cells characterized by the expression of CCR7 and CD62L, two molecules required for homing in T-cell areas of secondary lymphoid organs. Upon antigenic stimulation, central memory T-cells produce low levels of effector cytokines such as IL-4 and IFN-γ, but high levels of IL-2, which is able to sustain their rapid and consistent proliferation. Upon antigen encounter central memory T-cells undergo: 1) Proliferation, resulting in an auto-regenerative process, aimed at increasing their pool, and 2) differentiation, resulting in the generation of effector memory T-cells, which are characterized by a low proliferative potential but are able to migrate to inflamed non-lymphoid tissues and mediate the effector phase of the immune response (8). Ag withdrawal is critical to avoid excessive TCR stimulation and activation-induced cell death, and for the generation of central memory T cells. Appropriate T-cell homeostasis is ensured by cytokines tightly regulating survival, proliferation and apoptosis of human and murine T lymphocytes. Among the soluble factors the common γ chain-binding cytokines such as IL-2, IL-4, IL-7, IL-9, IL-15 and IL-21 promote cell survival and homeostatic proliferation (2). In particular, IL-2 sustains both T-cell proliferation and apoptosis upon antigen encounter. TCR as well as IL-7-generated signals control proliferation and survival of naïve and memory cells (7, 9-14). In the absence of TCR engagement, IL-7 renders mature human naïve and memory $CD4^+$ T cells less susceptible to Fas-induced cell death (15). Moreover, by inducing the upregulation of Bcl-2 it favors the transition of Ag-experienced $CD4^+$ T cells to resting memory cells (9, 11). Finally, IL-15, combines an anti-apoptotic activity with a consistent effect in promoting the proliferation of naïve and memory T cells (16). For these reasons the common γ chain-binding cytokines have been previously used in combination with Ag-driven cell expansion for the in vitro maintenance and expansion of Ag-specific T cell lines. In some instance common γ chain-binding cytokines were also used to ameliorate the detection of Ag-specific T cells.

US patent application US2005/0074822 refers to a method of detecting an antigen specific T cell population wherein the cells are exposed to the antigen in the presence of common γ chain-binding cytokines. This method does not allow the expansion, or the enrichment of Ag-specific memory cells.

DESCRIPTION OF THE INVENTION

On the contrary in the present invention, the authors have investigated whether IL-7 and/or IL-15, would allow:
1) Memory T cells to accumulate in an Ag-free environment, (and, can be thus used in short-term in vitro culture in the absence of Ag-driven cell expansion to enrich for rare populations of in vivo-primed antigen-specific T cells each of one being specific for an antigen encountered in vivo) granting the identification of pathogen/tumor/allergen/self-specific T cells. 2) Central memory cells to expand while maintaining their functional phenotype (and can thus be used to promote gene-modification of central memory lymphocytes by viral vectors).

To validate the invention, the authors took advantage of three unrelated preclinical animal models, and furthermore validation on human samples was generated. The first two models allow the enumeration of Ag-specific T cells at the single cell level in the context of tumor disease (17) and of dendritic cell-based vaccination (18). These models allow validating the concept of T cell accumulation in vitro in an Ag-free environment. The third model is based on the engraftment of human T cells in immunedeficient mice, thus allowing to evaluate the immune competence of genetically modified central memory T cells.

Model 1.

To study tumor-specific T cell responses, the authors took advantage of an animal model recently developed (17). In this model, TS/A-LACK tumors (TS/A adenocarcinoma tumor cells expressing the *Leishmania Major*-derived antigenic protein LACK) are grown in syngeneic BALB/c mice and LACK-specific T cells are studied in the peripheral lymphoid organs (lymph nodes, spleen or blood) by flow cytometry with fluorescent LACK-peptide/MHC class II multimers. In this model, LACK-specific T cells can also be independently characterized by Ag-induced intracellular cytokine release. TS/A-LACK-specific T cells can be traced in BALB/c mice and in 16.2β TCR transgenic mice, which express a transgenic TCR β chain specific for LACK allowing an easier characterization of LACK-specific CD4 T-cell response. Furthermore, TS/A cells naturally express the envelope protein gp70 of an endogenous MuLV for which an immunodominant epitope was previously described (AH-1, (19)). Thus in addition to the LACK-specific CD4 T cell response, also the AH-1-specific T cell responses can be traced in TS/A-LACK tumor-bearing mice.

Model 2.

To study vaccine-specific T cell responses, the authors used bone-marrow-derived dendritic cells (DC) pulsed with the viral SV40-derived antigenic peptide Tag IV and vaccined syngeneic C57BL/6 mice (18). In this model, Tag IV-specific T cells were also characterized by antigen-specific cytokine secretion assay ex vivo in order to enumerate TAG IV-specific CD8 T cell response.

The study of Ag-specific CD4 (LACK) and CD8 (AH-1, Tag IV) T cell response was performed ex vivo and after the proposed short-term in vitro culture performed in the presence of IL-7 in the absence of Ag-driven cell stimulation. Optimal amounts of IL-7 and, as comparison IL-2, or IL-15, and as negative controls, IL-6, IL-10 and TNF-α were used. In all the experimental conditions the authors found that a simple short-term culture in optimal amounts of IL-7 allowed the accumulation of in vivo-primed Ag-specific T lymphocytes bypassing the need of Ag-driven cell expansion and maintaining the lymphocyte original phenotype. Most importantly, the short-term culture in IL-7 in some instances unmasked rare population of Ag-specific T cells, otherwise undetectable by conventional assays.

As for validating results on human samples T lymphocytes were derived from healthy donors and *Mycobacterium tuberculosis* infected patients and analyzed ex vivo and after an IL-7-driven short-term culture by antigen-specific cytokine release. In all cases, IL-7 favored the accumulation of antigen-specific IL-2 and IFN-γ-producing intermediate memory T cells by sustaining their in vitro proliferation and survival. IL-7 efficacy relied on in vivo antigen encounter, optimal cytokine amounts, and high cell density conditions, and was prevented by anti-LFA-1 antibody and by Cyclosporin A. IL-7 was markedly more efficient than IL-2 and IL-15 for CD4 memory T cell expansion, while IL-15 and IL-2 favored CD8 memory T cell expansion.

Results from the study show that:
1) A short-term culture in high cell density, and optimal IL-7, or IL-15 amounts is suitable for the maintenance and the selective expansion of a population of in vivo primed memory CD4 and CD8 T cells. These cells are best defined as capable of IL-2 and IFN-g secretion and of fast proliferation in response to IL-7 (CD4) or IL-15 (CD8).
2) The short-term culture in IL-7 (and to some extent IL-15 or IL-2) allows the detection of in vivo primed rare Ag-specific CD4+ or CD8+ T cells possibly undetectable by conventional methods, bypassing the need for in vitro Ag-driven expansion.
3) The culture in IL-7 (and to some extent in IL-2, or IL-15) enriches both the frequency and total number of in vivo primed Ag-specific T cells in an Ag-independent manner.
4) The short-term culture in IL-7 (and not IL-2) preserves all of the lymphocyte subsets independently from their activation status, does not favour terminal differentiation of the cells, and maintains the original phenotype of in vivo primed T cells.
5) The short-term culture in IL-7 in the absence of the Ag allows the accumulation of $CD4^+$ effector and central memory T lymphocytes capable of Ag-specific responses and long-term survival.
6) IL-7/IL-15-expanded cells are of clinical relevance as they are capable of delaying tumor growth when transferred into naive animals.

The advantage of the proposed strategy over the existing protocols lies on:
A) The possibility to enrich biological samples for antigen-specific memory T cells in the absence of TCR engagement (i.e. Ag-stimulation). Differently from existing strategies, this protocol does not alter the surface and functional phenotype of the cells. By coupling this new approach to the spreading techniques of peptide/MHC I or MHC II multimer staining it would be possible to enumerate Ag-specific T cell in biological sample and evaluate their in vivo frequency.
B) The possibility to reveal rare antigen-specific T cells otherwise undetectable ex vivo by conventional techniques. This will be critical for all those clinical condition for which the enumeration of rare antigen-specific in vivo primed CD4 and CD8 T cells is of diagnostic and prognostic interest, and currently relies on repeated and time-consuming in vitro Ag-driven cell expansion.
C) The possibility to expand effector, central and intermediate memory T lymphocytes. No protocols are currently available to maintain central memory lymphocytes in vitro. The present invention has an impact on adoptive immuno-therapeutic strategies. Indeed while available strategies require the transfer of high numbers of short-lived effector cells, comparable or even improved clinical results are likely to be achieved by the transfer of limited numbers of renewable long-lived memory IL-7/IL-15-cultured cells.

Overall, the present invention has both diagnostic and therapeutic implication. On one hand it will aid the identification of rare populations of clinically relevant pathogen/tumor-specific T cells, and on the other hand it will also ameliorate current adoptive immunotherapeutic strategies.

It is expected that the defined in vitro culture will be applicable for the study of several infectious and immune-mediated diseases such as HIV, CMV, RSV, Flu, HBV, HPV, Cancer, Diabetes, Rheumatoid Arthritis, Lyme Arthritis, Multiple Sclerosis, Celiac Disease).

Model 3.

Another aspect of this invention relies on the concept that central memory cells, upon TCR triggering in the presence of co-stimulation and culture with gamma-cytokines, can expand in vitro and be genetically modified by a viral vector, while maintaining their functional phenotype.

It is believed that cellular therapy with T lymphocytes has a tremendous potential to cure cancer, infections, immuno-deficiencies and autoimmunity. Moreover, it can be used to modulate the immune responses occurring in the context of transplantation. Genetic modification is aimed at broaden the therapeutic interval of T lymphocytes by increasing their efficacy and/or limiting their toxicity. This is achieved by the transfer of genes encoding for novel receptors, biologically active products, resistance and control factors. Control factors are expected to provide selective in vivo elimination/inactivation of gene-modified cells if a toxic/unwanted effect ensues. Suicide gene therapy in the context of allogeneic hematopoietic cell transplantation (allo-HCT) is the clearest example of how genetic modification of T-cells with a control factor achieves a therapeutic benefit. In allo-HCT, the immune recognition of host antigens by donor T-cells is a "double-edged" sword, leading to specific beneficial effects: T cells 1) mediate a direct anti-tumor effect (graft-versus-leukemia-GvL); 2) promote the engraftment of hematopoietic precursors; 3) provide an intact immune system to transplanted patients thus allowing to abate the incidence and severity of post-transplant infections. Unfortunately donor T-cells may also react against healthy host tissues, thus leading to the life-threatening graft-versus-host disease (GvHD) (20). Genetic modification of T-cells with a retroviral vector expressing the Herpes Simplex Virus-thymidine kinase (TK) suicide gene confers selective sensitivity to the pro-drug ganciclovir (GCV). In patients, the infusion of $TK^+$ lymphocytes and the subsequent administration of GCV resulted in a time-wise modulation of anti-host reactivity for the preservation of T-cell benefits, and a selective control of GvHD (21-23).

The success of T-cell therapy and T-cell gene therapy depends on the ability of T-cells to proliferate and survive long-term in vivo. To achieve this goal, T-cells need to properly home to secondary lymphoid organs, where appropriate encounter with the antigen occurs and induces T-cells to acquire effector functions. It is becoming increasingly recognized that these attributes tends to segregate at early stages of mature T-cell differentiation, and in particular in the central memory compartment. Genetic modification with viral vectors may alter T-cell physiology. In particular, genetic modification through retroviral vectors (RV) requires cellular proliferation. This is currently achieved by activation with polyclonal stimuli and culture in the presence of high doses of recombinant human IL-2. The authors found that gene-modified human T lymphocytes generated with current protocols, i.e. activation with soluble anti-CD3 antibodies and culture in the presence of IL-2, are mainly effector memory cells, that readily display effector functions in vitro but that poorly engraft in conditioned immunodeficient hosts. Since expansion and persistence of human T cells is a crucial pre-requisite for an effective T-cell based gene therapy, the present invention provides a method of T cell culture and transduction able to generate genetically modified central memory T cells. To this purpose, the authors combined:

activation of T cells with beads conjugated with anti-CD3 and anti-CD28 antibodies culture with IL-7 and IL-15 at low doses transduction with a retroviral vector.

Results indicate that the production of gene-modified lymphocytes with beads in the presence of IL-7 and IL-15 is feasible and that these cells have a physiologic CD4/CD8 ratio and a central memory functional phenotype, as defined by i) an absence of CD45RA expression and presence of CD62L expression, ii) a co-expression of the molecules CD27 and CD28 and iii) a production of IL-2 in the absence of IFN-γ and/or IL-4.

Furthermore, the authors observed that genetically modified central memory T-cells infused in conditioned immunodeficient hosts i) engraft and expand at significantly higher levels than effector memory genetically modified T cells and ii) are more potent than effector memory genetically modified lymphocytes at inducing an immune response to host antigens.

These results demonstrate that fully functional central memory recombinant lymphocytes can be obtained and exploited for the cure of human diseases.

In the present invention, fully functional central memory recombinant lymphocytes means central memory T-cells with long-term survival potential, able to home to peripheral lymphoid organs, and to differentiate into effector cells upon antigen re-encounter in vivo. Therefore it is an object of the instant invention an in vitro method for expanding rare populations of antigen specific memory T cells in a sample comprising the step of exposing said sample to an effective amount of at least one cytokine receptor agonist able to selectively expand said rare populations of antigen specific memory T cells. Preferably the cytokine receptor agonist is a cytokine or a derivative thereof.

In a preferred embodiment the at least one cytokine receptor agonist is a IL-7 receptor agonist or a IL-15 receptor agonist, preferably a IL-15 receptor agonist or a IL-7 receptor agonist is also present, respectively.

In a preferred embodiment the rare populations of antigen specific memory T cells comprise $CD4^+$ and/or $CD8^+$ and/or γδ and/or NKT T cell populations.

In a preferred embodiment said sample is a biological sample belonging to the group of: blood and other liquid samples of biological origin, solid tissue samples, tissue cultures of cells derived therefrom and the progeny thereof, isolated cells from biological samples as i.e. PBMCs.

It is a further object of the invention an in vitro method for detecting a rare population of antigen specific memory T cells in a sample comprising the steps of:

a) exposing said sample to an effective amount of at least one cytokine receptor agonist able to selectively expand rare populations of antigen specific memory T cells as previously described;

b) incubating said sample with at least one ligand, being the ligand specific for one of said expanded rare populations of antigen specific memory T cells;

c) detecting the expanded rare population of antigen specific memory T cells bound to the specific ligand.

Preferably said specific ligand is the specific antigen, or a derivative thereof for one of said rare populations of antigen specific memory T cells, more preferably the specific antigen is associated to a microbial pathogen including but not limited to *Mycobacterium, Pneumocystic carinii, Plasmodium falciparum, Candida, Toxoplasma*, CMV, EBV, BPV, HCV, HBV, HIV. Alternatively the antigen is a tumor-associated antigen. Alternatively the antigen is an allergen. Alternatively the antigen is a self-antigen.

In a preferred embodiment the specific antigen is present as an antigen-MHC complex, or a derivative thereof.

In a preferred embodiment the detecting of said expanded rare populations of antigen specific memory T cells is performed by a binding assay. Alternatively the detecting of said expanded rare populations of antigen specific memory T cells is performed by a cytokine release assay. Alternatively the detecting of said expanded rare populations of antigen specific memory T cells is performed by a proliferation assay.

In a preferred embodiment cells are labeled with a fluorescent vital dye before incubating the sample with the specific ligand and the detecting step is performed by a dye dilution assay. It is a further object of the invention a kit for carrying out the method for detecting a rare population of antigen specific memory T cells in a sample as above described comprising at least one cytokine receptor agonist; at least one ligand specific for the rare populations of antigen specific memory T cells; detecting means.

It is a further object of the invention an in vitro method for isolating a rare population of antigen specific memory T cells in a sample comprising the steps of:

a) exposing said sample to an effective amount of at least one cytokine receptor agonist able to selectively expand rare populations of antigen specific memory T cells as above described;
b) incubating said sample with at least one ligand, being the ligand specific for one of said expanded rare populations of antigen specific memory T cells;
c) isolating the expanded rare population of antigen specific memory T cells bound to the specific ligand.

Preferably said specific ligand is the specific antigen or a derivative thereof for one of said rare populations of antigen specific memory T cells; more preferably the specific antigen is associated to a microbial pathogen including but not limited to *Mycobacterium, Pneumocystic carinii, Plasmodium falciparum, Candida, Toxoplasma*, CMV, EBV, BPV, HCV, HBV, HIV. Alternatively the antigen is a tumor-associated antigen. Alternatively the antigen is an allergen. Alternatively the antigen is a self-antigen.

In a preferred embodiment the specific antigen is present as an antigen-MHC complex, or a derivative thereof.

In a preferred embodiment the isolating of said expanded rare populations of antigen specific memory T cells is performed by a binding step. Alternatively the isolating of said expanded rare populations of antigen specific memory T cells is performed by measuring cytokine and cytotoxin production, including but not limited to ELISPOT assay, ELISA assay, flow cytometry cytokine detection assay for IL-2, IFN-g, IL-4, IL-5, IL-10, TNF-alfa, TGF-beta, granzymes.

It is a further object of the invention the in vitro methods as described for the diagnostic and/or prognostic clinical investigation of immune-, infectious-, cancer-, allergy-, auto-immune-related pathologies.

It is a further object of the invention the use of the rare T cell populations isolated according to the method as described above for the treatment and/or the prevention of immune-, infectious-, cancer-, allergy-, auto-immune-related pathologies. In a particular embodiment said rare T cell populations are genetically modified.

It is a further object of the invention an in vitro method for obtaining a genetically modified memory T cell population, comprising the steps of:
a) activating lymphocytes with at least two specific activating receptor agonists, including but not limited to agonist antibodies, recombinant ligands and derivatives thereof, able to drive lymphocyte activation;
b) exposing activated lymphocytes to an effective amount of at least one cytokine receptor agonist, able to selectively expand populations of memory T cells;
c) inserting and expressing an exogenous gene by means of an appropriate vector into cells as obtained in b).

Preferably the populations of memory T cells comprise CD4$^+$ and/or CD8$^+$ and/or γδ and/or NKT T cell populations.

Preferably lymphocytes are derived from a biological sample belonging to the group of: blood and other liquid samples of biological origin, solid tissue samples, tissue cultures of cells derived therefrom and the progeny thereof, isolated cells from biological samples as i.e. PBMCs.

Preferably the specific lymphocyte activating receptor agonist is conjugated to cell-mimicking supports, more preferably the cell-mimicking supports are paramagnetic beads. In a preferred embodiment one of the lymphocyte activating receptor agonists is specific for the CD3 polypeptide, preferably another of the lymphocyte activating receptor agonists is specific for a costimulatory receptor, i.e. CD28.

In a preferred embodiment the at least one cytokine receptor agonist is a IL-7 receptor agonist or a IL-15 receptor agonist, preferably a IL-15 receptor agonist or a IL-7 receptor agonist is also present, respectively.

In a preferred embodiment the vector is a viral vector.

In a preferred embodiment the exogenous gene encodes for a suicide gene, and/or a marker gene, and/or a biologically active molecule, and/or a receptor, and/or a soluble factor retained in the cell or released outside the cell, and/or a gene conferring resistance to a prodrug.

It is a further object of the invention the use of the genetically modified memory T cell population generated according to the method above described for the treatment and/or the prevention of cancer, infections, immunodeficiencies or autoimmunity or for transplantation of hematopoietic precursors or solid organs.

The invention will be now described by means of non-limiting examples, making reference to the following figures:

FIG. 1. IL-7 favors the accumulation of tumor-specific memory CD4$^+$ T cells without the need of Ag-stimulation. BALB/c mice (5 per group) were challenged with 3×10$^5$ TS/A-LACK or TS/A tumor cells and sacrificed 21 days later. Cells from pools of tumor-draining LN (A-D), and non draining LN (E-H) were analyzed ex vivo and after 7 days in culture with IL-7 alone. A, C, E, G) cells were stained as described in Material and Methods. Representative flow cytometry profiles are shown after gating on viable CD4$^+$, B220$^-$, CD8$^-$, CD11b$^-$, TOPRO-3$^-$ cells. The frequency of CD44$^{high}$I-A$^d$/LACK$^+$ CD4$^+$ cells is indicated. B, D, F, H) lymphocytes were stimulated with LACK aAPC (see Materials and Methods), fixed, permeabilized, stained with anti-CD4 mAb, anti-IL-2 and anti-IFN-γ mAbs, and analyzed by flow cytometry. Representative dot plots showing IL-2 and IFN-γ production by CD4$^+$ are shown. The frequency of cytokine-producing cells is reported in each quadrant. The experiment is representative of 6 independent determinations. In some cases, LACK-specific IFN-γ release was detected in IL-7-treated LN culture of TS/A-tumor-bearing mice. Even though the nature of these cells remains to be elucidated, these cells might be specific for the LACK homologue mammalian RACK (24).

Figure 2:
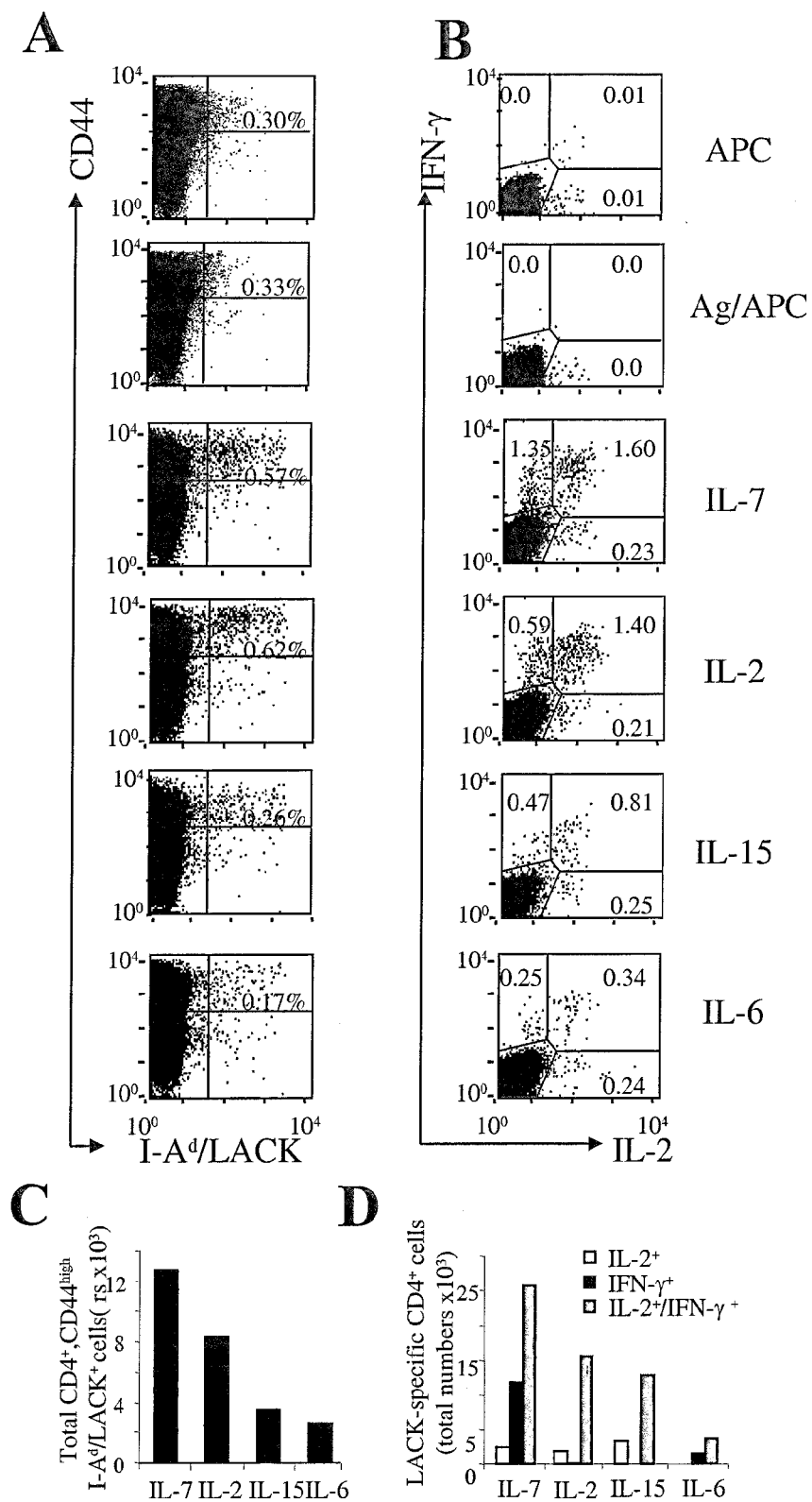

FIG. 2. IL-7 and IL-2, but not Ag, IL-15 and IL-6 elicit the accumulation of tumor-specific CD4$^+$ T cells. Pools of LN cells recovered from TS/A-LACK tumor-bearing BALB/c mice (n=5) were cultured with irradiated splenocytes in the absence (APC) or in the presence of the LACK peptide (Ag/APC) or with IL-7, IL-2, IL-15 and IL-6 alone. After 7 days, cells were recovered and surface stained to determine the frequency of Ag-experienced LACK-specific T cells (A, C), or stimulated with LACK aAPC to evaluate LACK-specific intracellular cytokine release (B, D), as described in FIG. 1. A) Representative flow cytometry profiles are shown after gating on viable CD4$^+$, B220$^-$, CD8$^-$, CD11b$^-$, TO-PRO-3$^-$ cells. The frequency (A) and total number (C) of CD44$^{high}$ I-A$^d$/LACK$^+$ CD4$^+$ cells among CD4$^+$ cells is indicated. B) Representative dot plots depict IL-2 and IFN-γ production by CD4$^+$ T cells. The frequency (B) and total number (D) of LACK-specific cytokine-producing cells among CD4$^+$ T cells is reported. The experiments are representative of 3 to 5 independent determinations.

Figure 3:
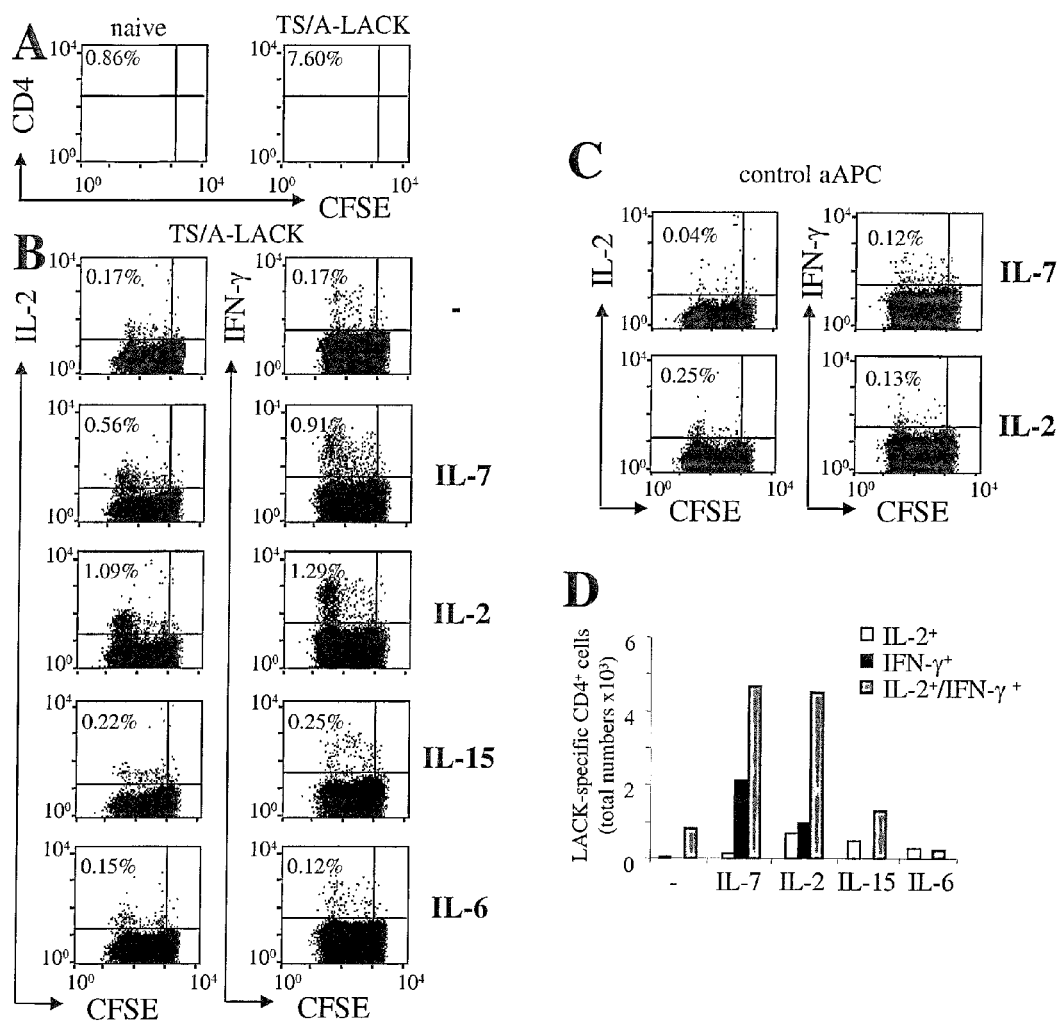

FIG. 3. IL-7 and IL-2 sustain the Ag-independent proliferation of in vivo-primed tumor-specific CD4$^+$ T cells. A) Pools of LN cells recovered from naïve or TS/A-LACK tumor-bearing BALB/c mice (n=5) were labeled with the CFSE vital dye and cultured for a week in plain medium. Representative dot plots of viable CD4$^+$ T cells are shown.

B-D) CFSE-labeled LN cells derived from TS/A-LACK-tumor-draining LNs were cultured without (nil) or with IL-7, IL-2, IL-15 and IL-6 for 7 days. Cells were then stimulated with LACK aAPC (B, D) or control aAPC (C), and analyzed by flow cytometry for intracellular cytokine release as described in FIG. 1. Representative dot plots showing the CFSE content and IL-2 or IFN-γ production by viable CD4$^+$ T cells are shown in B and C. In D, the total number of CFSE$^{dim}$ CD4$^+$≥T cells producing IL-2 and/or IFN-γ is depicted. The experiment is representative of 3 independent determinations.

Figure 4:
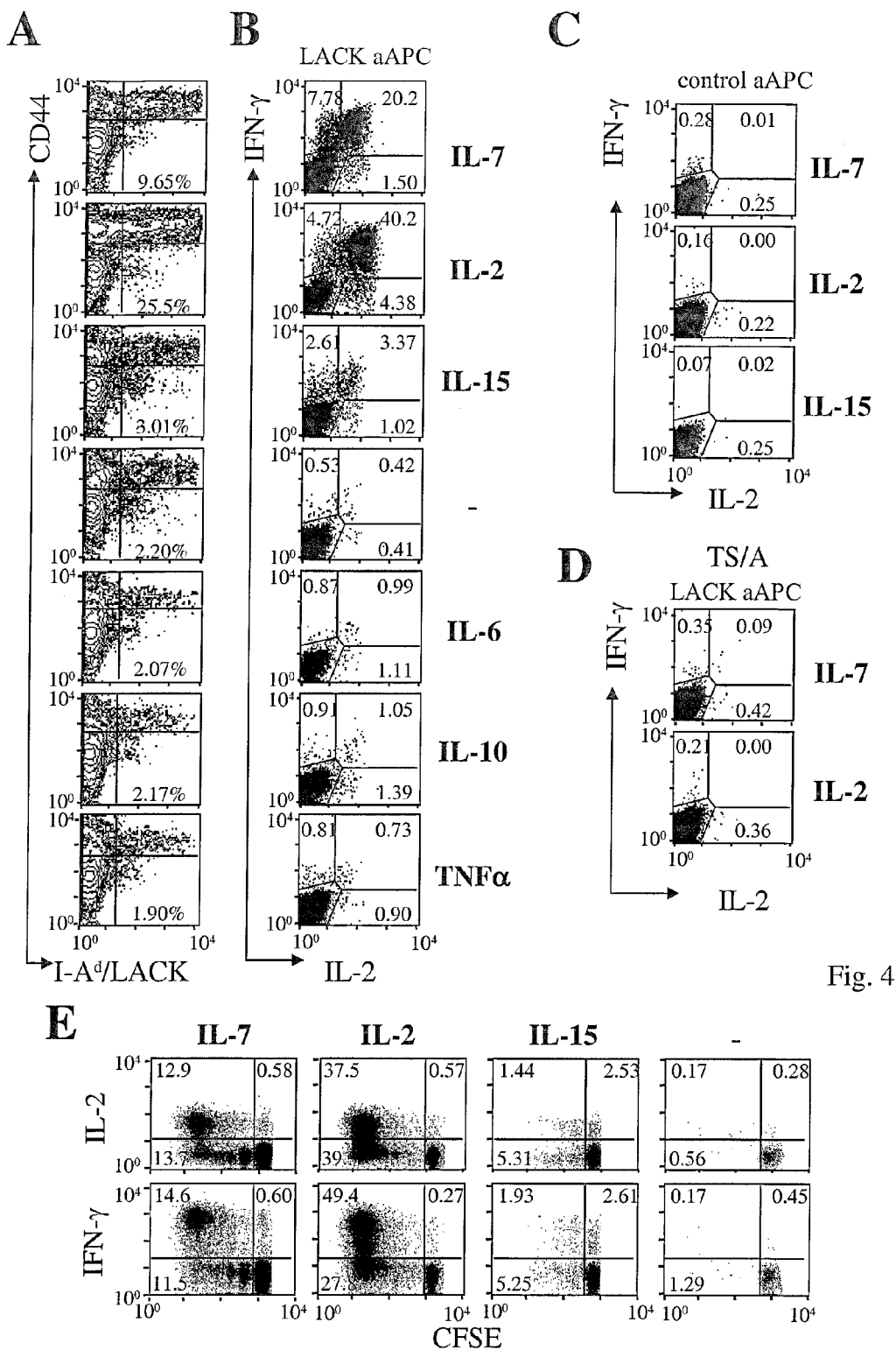

FIG. 4. IL-2, but not IL-15 and IL-6, IL-10, TNF-α mimics IL-7 and enriches cell cultures for tumor-specific memory CD4$^+$ T cells in the absence of Ag. TS/A-LACK and TS/A-tumor-draining LN derived from 16.2β transgenic mice were cultured for a week in the absence (−) or in the presence of the indicated recombinant cytokine alone and analyzed by flow cytometry as described in FIG. 1. A) Representative dot plots are shown after gating on viable CD4$^+$, B220$^−$, CD8$^−$, CD11b$^−$, TOPRO-3$^−$ cells. The frequency of I-A$^d$/LACK$^+$ CD4$^+$ cells is indicated. B-D) Lymphocytes derived from TS/A-LACK-(B, C) and TS/A-(D)-tumor draining LN cultures were stimulated with LACK aAPC (B, D) or control aAPC (C) to detect intracellular IL-2, IFN-γ and IL-4. Representative dot plots showing IL-2 and IFN-γ production by CD4$^+$ are shown. IL-4$^+$ cells were within background levels in all experiments. The frequency of IL-2$^+$, IFN-γ$^+$ cytokine-producing cells is reported in each quadrant. E) Tumor-draining LN cells from TS/A-LACK-tumor-bearing 16.2β mice were labeled with CFSE, and cultured in the absence (−) and in the presence of the indicated cytokines for a week. Thereafter the cells were re-stimulated with LACK aAPC ad analyzed by flow cytometry. Representative dot plots showing the CFSE content and IL-2, and IFN-γ production by CD4$^+$ are shown. The experiment is representative of 3 independent determinations.

Figure 5:
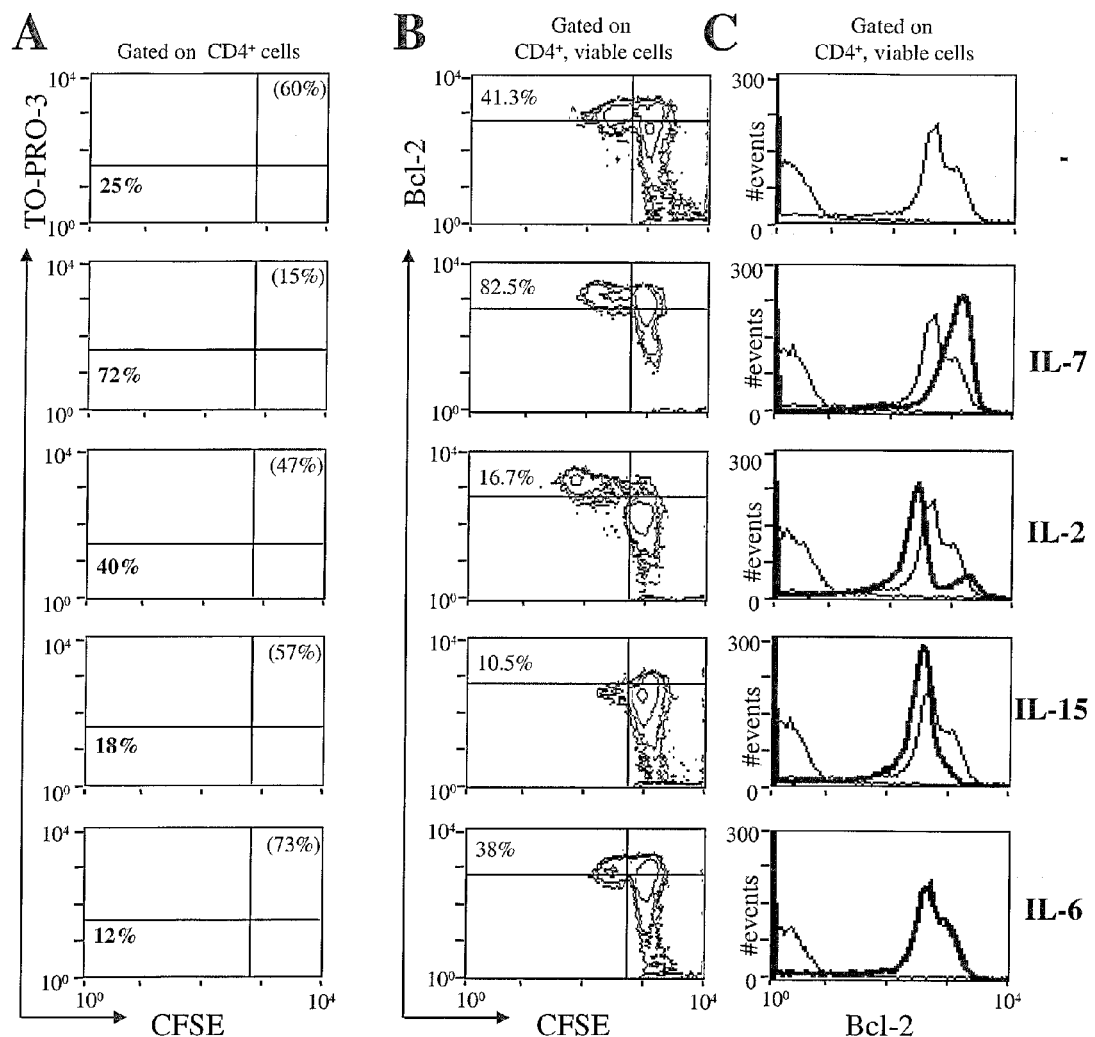

FIG. 5. IL-7 and IL-2 favor T cell survival and the optimal expression of Bcl-2. Cells from TS/A-LACK tumor draining LN were labeled with the CFSE vital dye and cultured in the absence (−) or in the presence of IL-7, IL-2, IL-15 and IL-6 alone. After 7 days, cells were recovered and stained with anti-CD4 mAb and TO-PRO-3 (A) and with anti-Bcl-2 mAb (B, C). A) representative dot plots of total CD4$^+$ cells are shown. The frequencies of total CD4$^+$ TOPRO-3$^+$ (brackets) and of CFSE dim, TO-PRO-3$^−$ cells (bold) are reported. B-C) events are shown after physical gating on viable CD4$^+$ lymphocytes. C) thin line: isotype control; thin lines-shaded profile: anti-Bcl-2 Ab, medium cultured cells; thick lines: anti-Bcl-2 Ab, cytokine-cultured cells. The experiment is representative of 2 independent determinations.

Figure 6:
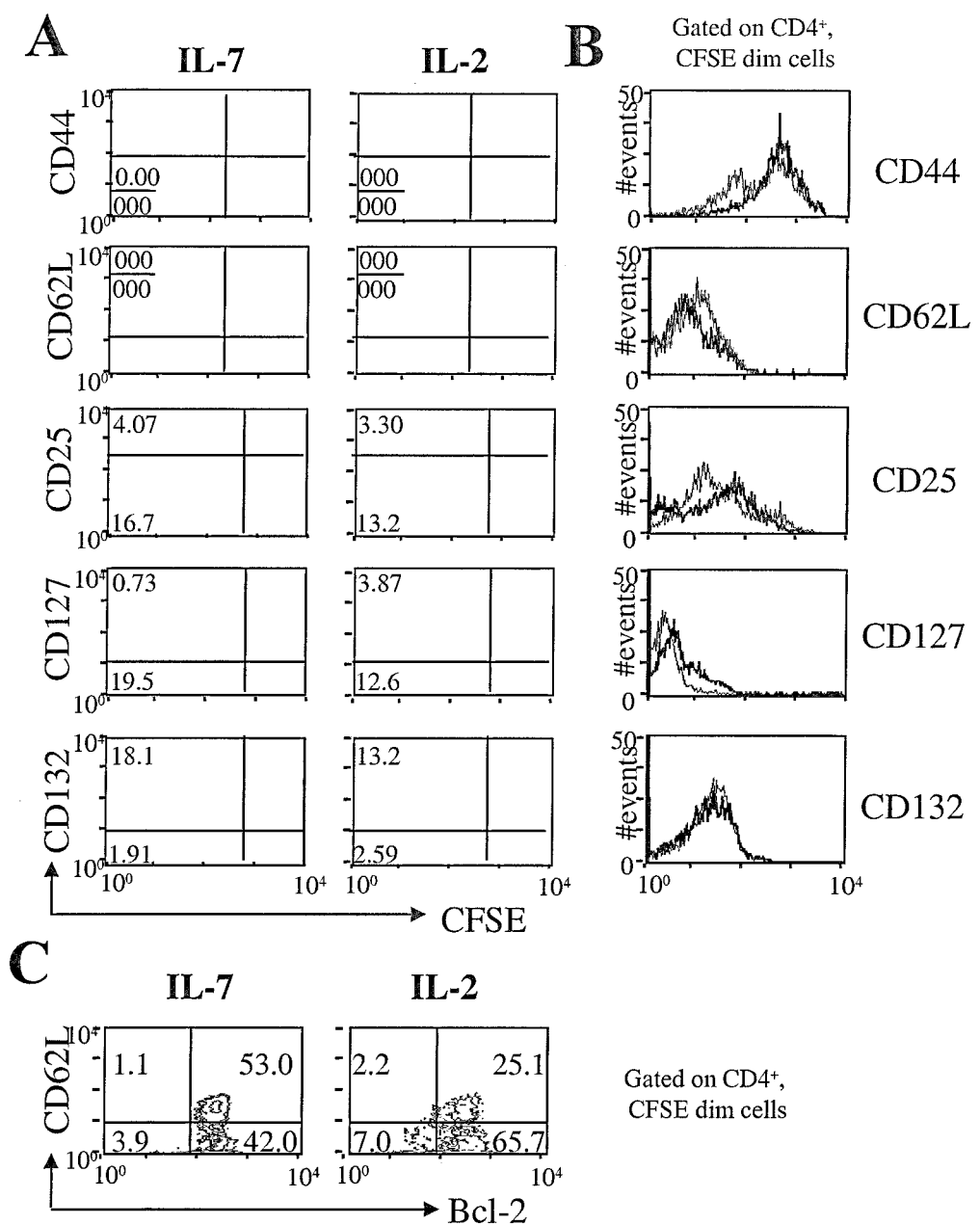

FIG. 6. Phenotype and subset representation of lymphocytes maintained in IL-7 and IL-2. CFSE-labeled TS/A-LACK-tumor-draining LN cultures were maintained for a week in the presence of IL-7 or IL-2. Thereafter the cells were stained with anti CD4, CD44, CD25, CD127, and CD132 mAbs. A) representative dot plots report the expression levels of CD44, CD62L, CD25, CD127, and CD132 of viable CD4+. B) overlay of CD4$^+$, CFSE dim cells derived from IL-7 (thin lines) and IL-2 (thick lines) cultures in the absence of Ag-stimulation are shown. C) CFSE-labeled cells were surface stained for CD4 and CD62L surface levels, and for intracellular Bcl-2. Dot plots are shown after gating on CD4$^+$ CFSE dim cells. The experiment is representative of 3 independent determinations.

Figure 7:
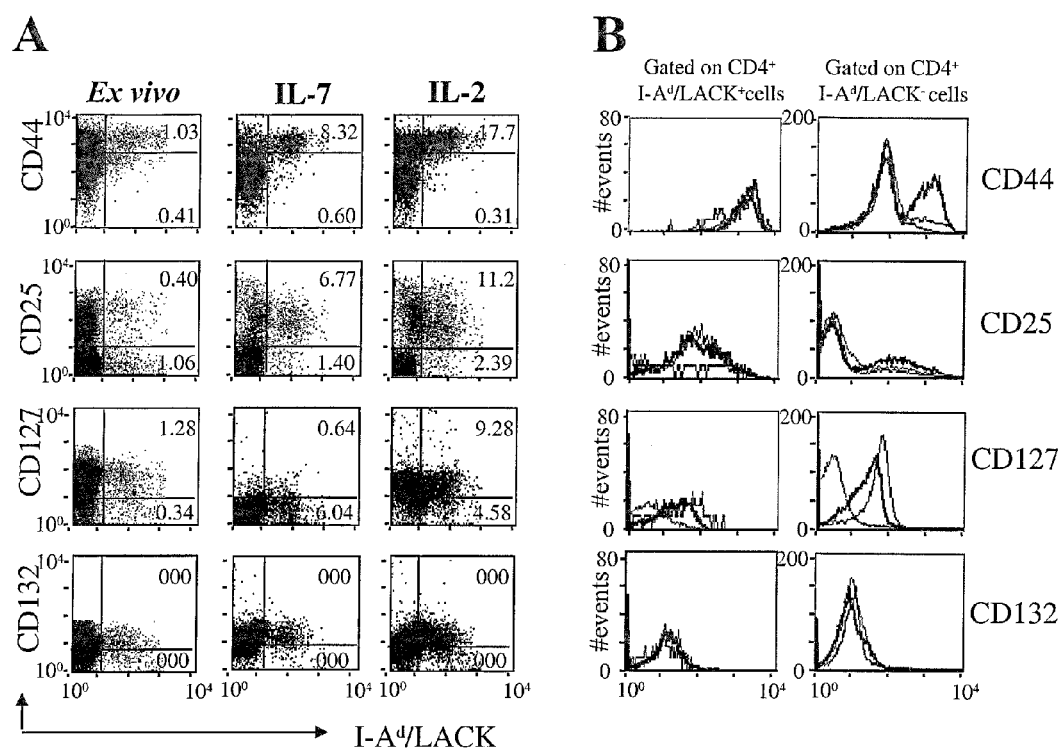

FIG. 7. IL-7-cultured cells are comparable to the ones found at the time of sacrifice. TS/A-LACK-tumor-draining LN derived from 16.20 transgenic mice were analyzed by I-A$^d$/LACK staining as described in FIG. 1 ex vivo and after the short-term culture in IL-7 or IL-2 in the absence of Ag-stimulation. A) representative dot plots report the expression levels of CD44, CD25, CD127, and CD132 of viable CD4$^+$, B220$^−$, CD8$^−$, CD11b$^−$, TOPRO-3$^−$ cells. B) overlay of CD4$^+$, I-A$^d$/LACK$^+$ and CD4$^+$, I-A$^d$/LACK$^−$ after gating on B220$^−$, CD8$^−$, CD11b$^−$, TOPRO-3$^−$ lymphocytes are shown. Ex vivo: dotted lines; thin line: IL-7; thick line: IL-2.

Figure 8:
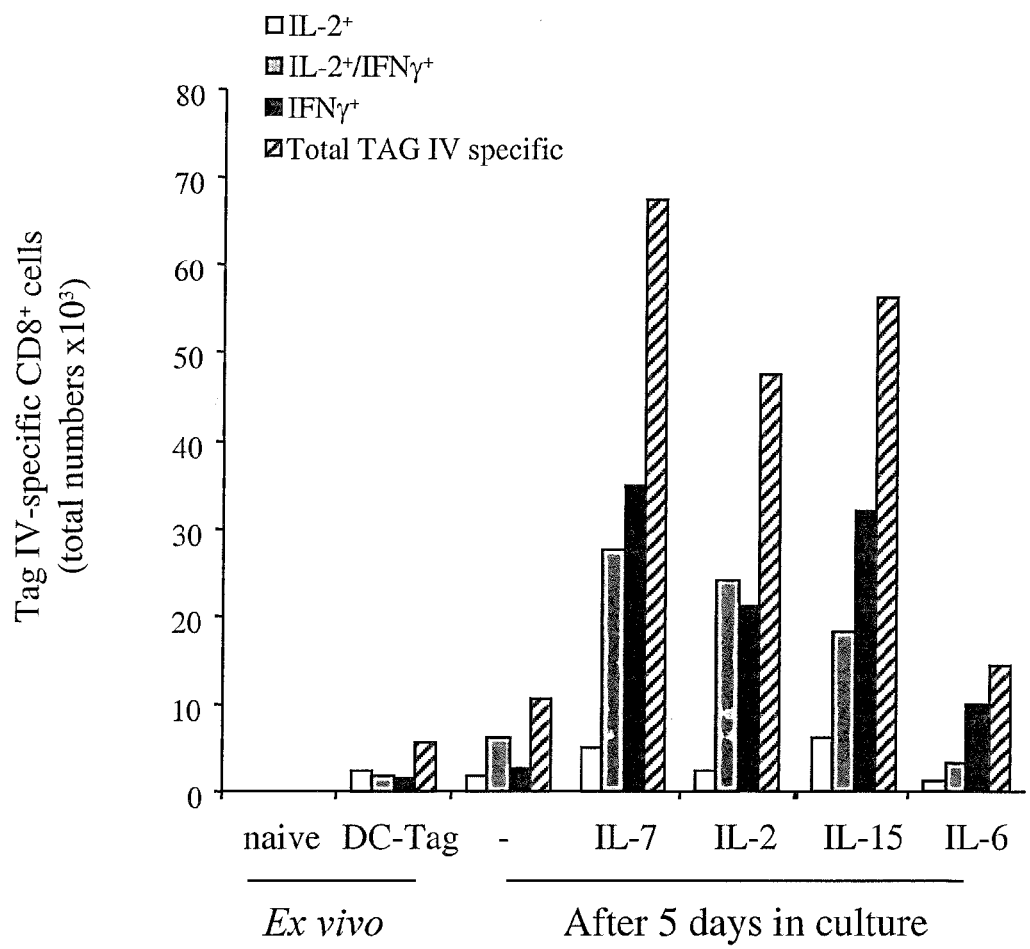

FIG. 8. IL-7-, IL-2- or IL-15-driven cultures are enriched for in vivo-primed TAG IV-specific memory CD8+ T cells. C57BL/6 mice were immunized with bone marrow-derived dendritic cells pulsed with the Tag IV peptide. Fourteen days later axillary, brachial and inguinal LN cells were recovered and analyzed ex vivo and after a week in culture in the absence or in the presence of IL-7, IL-2, IL-15, IL-6. The total number of Tag IV-specific cytokine-producing CD45.1$^−$ CD8$^+$ T cells is reported. The experiments are representative of 2 independent determinations.

Figure 9:
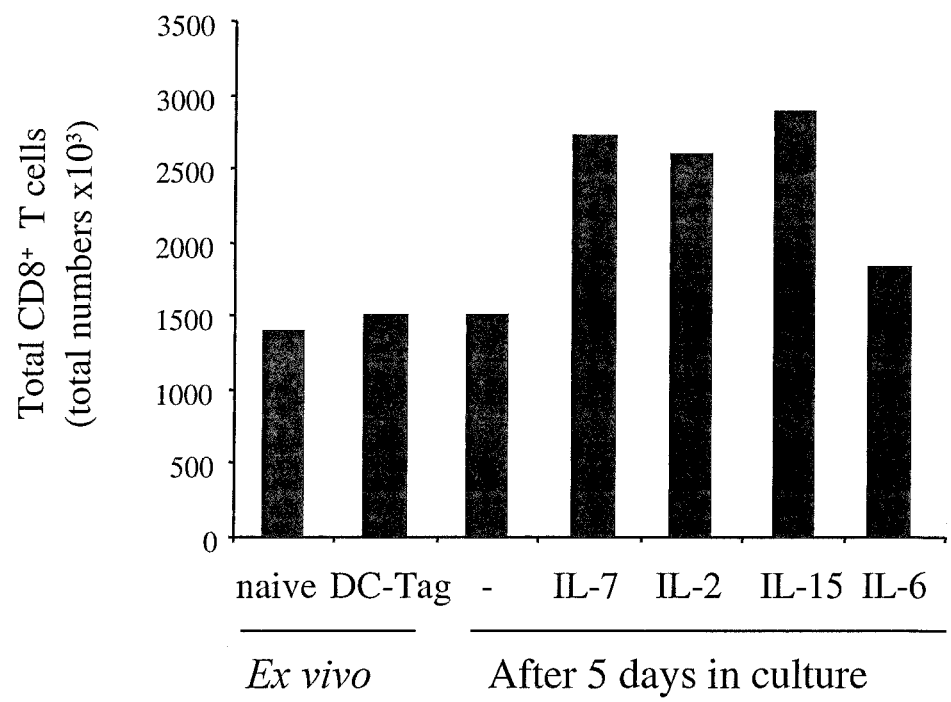

FIG. 9. IL-7-, IL-2- or IL-15-driven cultures rescue comparable numbers of CD8+ T cells. C57BL/6 mice were immunized with bone marrow-derived dendritic cells pulsed with the Tag IV peptide. Fourteen days later axillary, brachial and inguinal LN cells were recovered and analyzed ex vivo and after a week in culture in the absence or in the presence of IL-7, IL-2, IL-15, IL-6. The total number of CD45.1$^−$ CD8$^+$ T cells is reported. The experiments are representative of 2 independent determinations.

Figure 10:
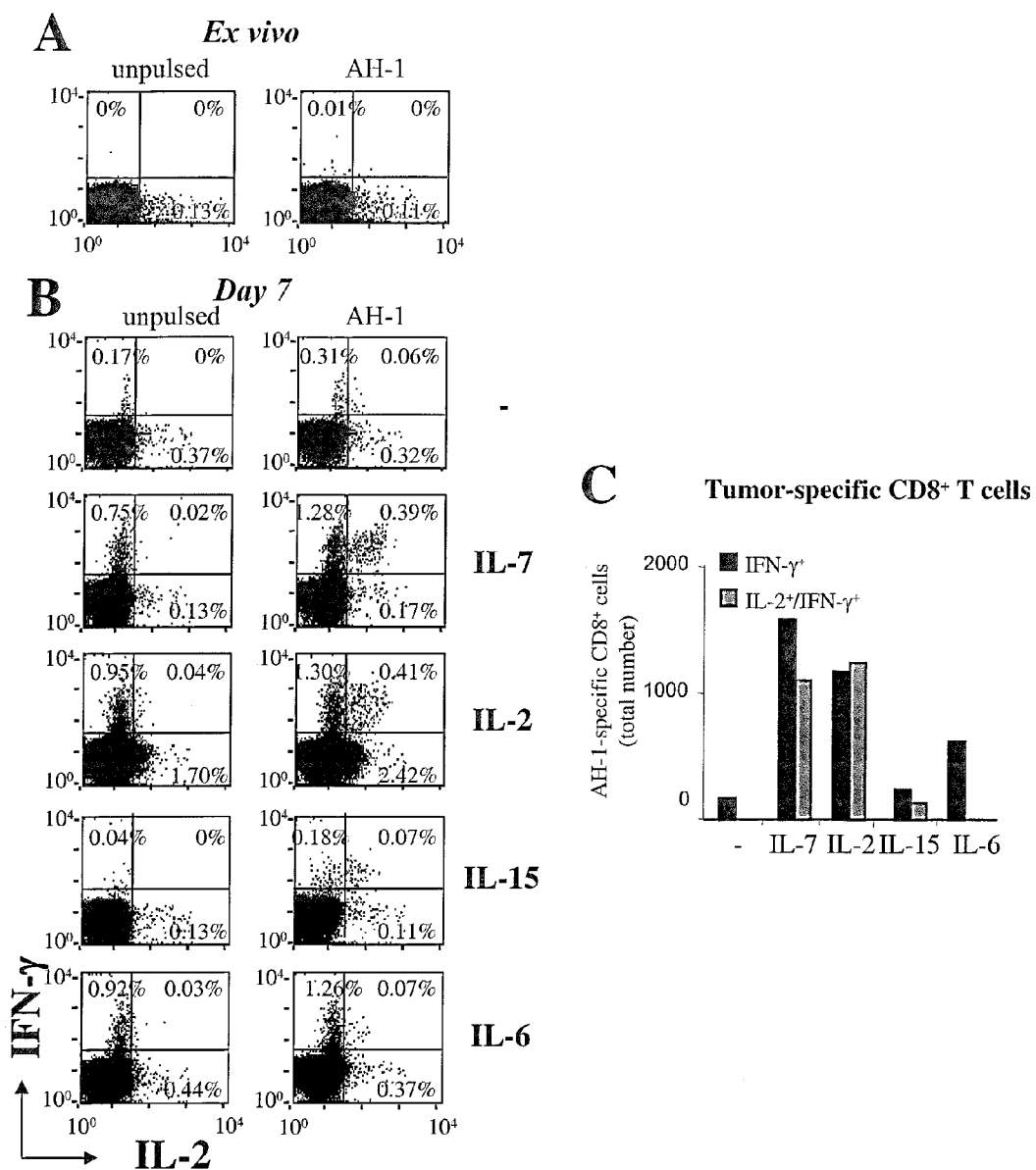

FIG. 10. IL-7 favors the accumulation of tumor-specific memory CD8$^+$ T cells otherwise undetectable ex vivo. A) BALB/c mice (5 mice per group) were challenged with 3×10$^5$ TS/A-LACK tumor cells and sacrificed 21 days later. Cells from pools of tumor draining LN (A-C) were analyzed ex vivo (A) and after 7 days in culture in the absence or in the presence of IL-7, IL-2, IL-15, IL-6 (B-C). A) Representative dot plots depict IL-2 and IFN-γ production by KJ1.26$^−$ CD8$^+$ T cells. The frequency (A, B) and total number (C) of AH-1-specific cytokine-producing KJ1.26$^−$ CD8$^+$ T cells is reported.

Figure 11:
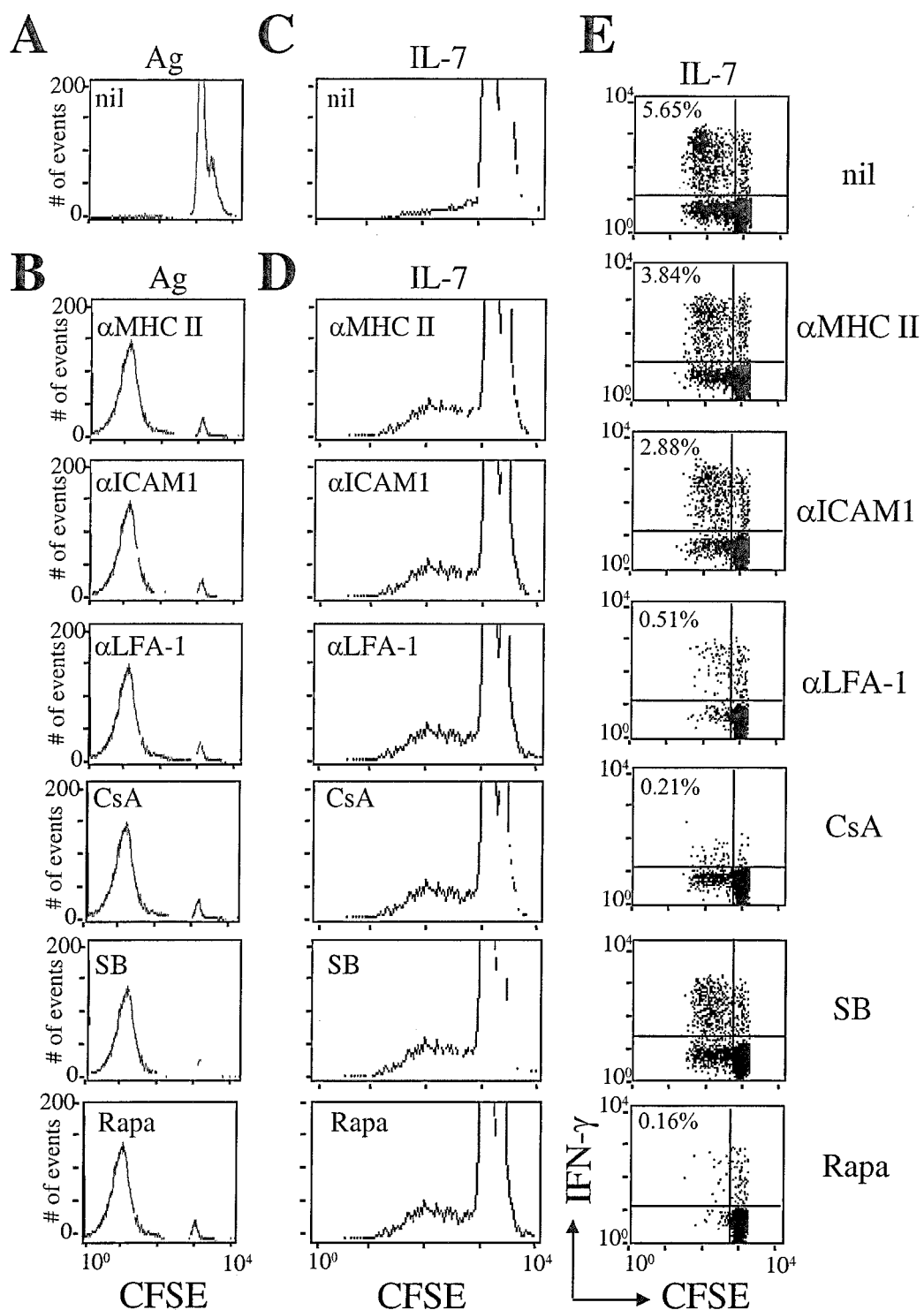

FIG. 11. Intermediate memory CD4$^+$ T cells accumulate in the presence of IL-7 in a cell-density dependent, CsA-sensitive manner. Cells derived from the axillary, brachial and inguinal LN of naïve (A, B) and TS/A-LACK tumor-bearing (C-E) 16.2β mice were labeled with CFSE and respectively cultured for 7 days in plain medium, in the presence of LACK peptide (Ag) (A, B) or IL-7 (C-E) in the absence (nil) or in the presence of the indicated inhibitors. At the end of the culture the cells were stimulated for 5 h with L/28 aAPCs, and intracellular cytokine release was determined. A-D) Histograms show the CFSE dilution profile of equivalent numbers of (7×10$^4$) CD4$^+$ T cells. In A and C the thin lines reflect the CFSE profile of CD4+ T cells cultured in plain medium, while the thick lines depict the CFSE profile of CD4+ T cells cultured in Ag or IL-7, respectively. In B and D, thin line: cells cultured in the absence of the inhibitor, thick line: cells cultured in the presence of the inhibitor. E) Dot plots are shown after gating on viable CD4$^+$ T cells. Percentages indicate the frequency of LACK-specific cytokine secreting cells.

Figure 12:
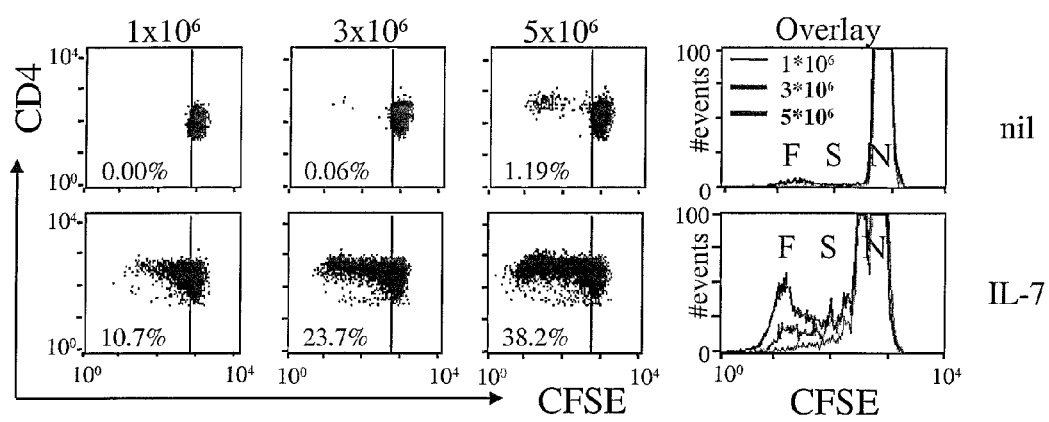

FIG. 12. IL-7 sustains the fast, Ag-independent proliferation of a fraction of human peripheral blood CD4$^+$ T cells. Human PBMCs from healthy donors were labeled with the CFSE vital dye and cultured for 7 days in the absence (nil) or in the presence of recombinant human IL-7 (100 ng/ml) at the indicated cell densities. Representative dot plots of viable CD4$^+$ T cells are depicted. The frequency of CFSE$^{dim}$ CD4$^+$ T cells is indicated. B) Histogram overlays of CD4$^+$ T cells cultured at the indicated cell density (N:non proliferating cells, S and F: slow and fast-proliferating cells).

Figure 13:
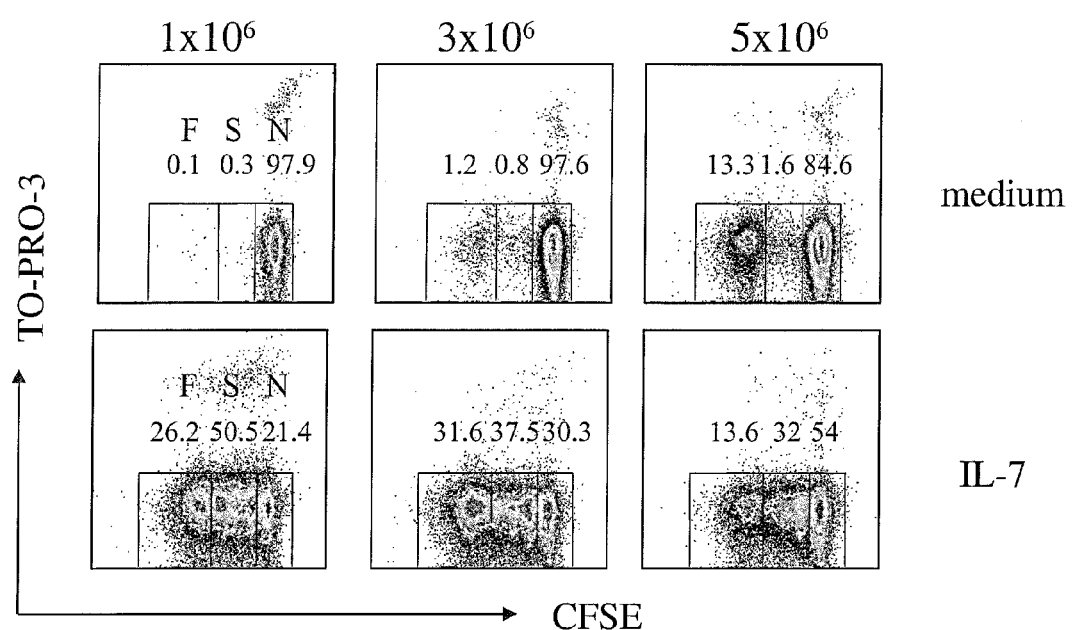

FIG. 13. IL-7 sustains the accumulation of fast-dividing cells in autologous serum. Human PBMCs from a healthy donor were labeled with the CFSE vital dye and cultured for 7 days in culture medium addition of 10% autologous serum in the absence (nil) or in the presence of recombinant human IL-7 (100 ng/ml) at the indicated cell densities. Representative dot plots of viable CD4$^+$ T cells are depicted. The frequency of non proliferating (N), and slow-(S) and fast-(F) proliferating CFSE$^{dim}$ CD4$^+$ T cells is indicated.

Figure 14:
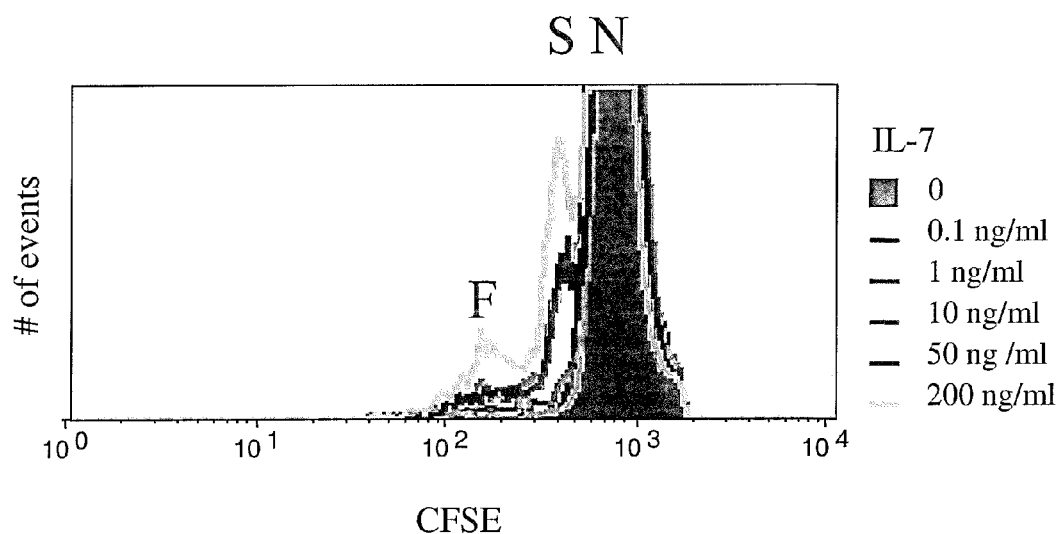

FIG. 14. IL-7-driven accumulation of fast-dividing CD4 T cells is dose dependent. Human PBMCs from healthy donors were labeled with the CFSE vital dye and cultured for 7 days in the presence of the indicated amounts of recombinant human IL-7. Representative dot plots of viable CD4$^+$ T cells are depicted. Non proliferating (N), and slow-(S) and fast-(F) proliferating CFSE$^{dim}$ CD4$^+$ T cells are indicated.

Figure 15:
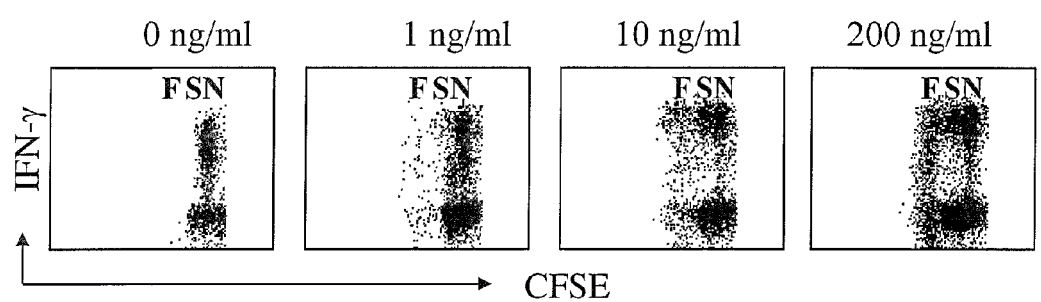

FIG. 15. IL-7 sustains the accumulation of fast-dividing IFN-γ-producing memory CD4$^+$ T cells. Human PBMCs from healthy donors were labeled with the CFSE vital dye and cultured for 7 days in the presence of the indicated amounts of recombinant human IL-7. After 7 days, cells were harvested and re-stimulated with PMA and Ionomycin for 6 hours. Cells were then surface stained, fixed and stained with anti-IFN-γ mAb. Representative dot plots of viable CD4$^+$ T cells are depicted.

Figure 16:
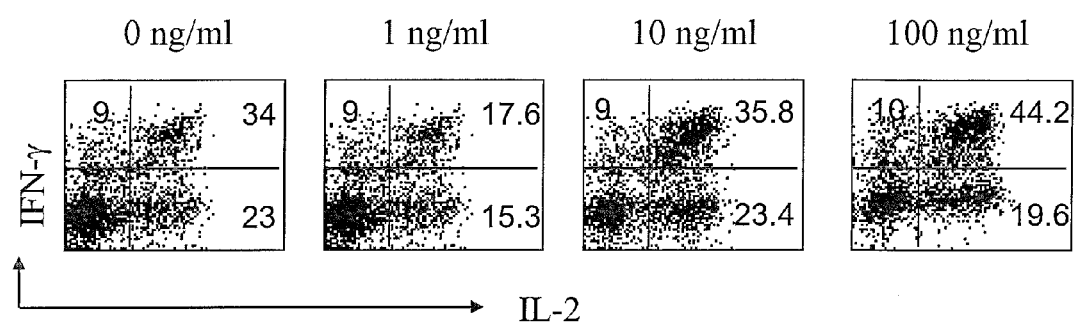

FIG. 16. IL-7-driven accumulation of IL-2/IFN-γ$^+$ CD4$^+$ T cells is dose dependent. Human PBMCs from healthy donors were cultured for 7 days in the presence of the indicated amounts of recombinant human IL-7. After 7 days, cells were harvested and re-stimulated with PMA and Ionomycin for 6 hours. Cells were then surface stained, fixed and stained with anti-IFN-γ mAb. Representative dot plots of viable CD4$^+$ T cells are depicted.

Figure 17:
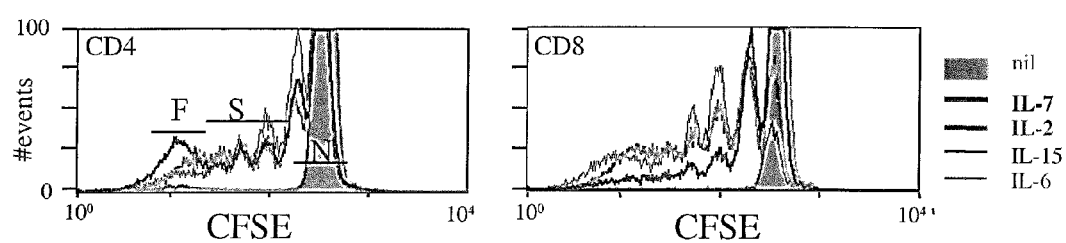

FIG. 17. IL-7 best expands fast-dividing memory CD4$^+$ lymphocytes, while IL-15 drives the accumulation of fast-dividing memory CD8$^+$ T lymphocytes. CFSE-labeled human PBMCs were cultured in plain medium (nil) or in the presence of human recombinant IL-7, IL-2, IL-15, and IL-6 for 7 days, then stained with anti-CD4 and anti-CD8 mAb, and analyzed by flow cytometry. Histogram overlays show the CFSE content within the same number of CD4$^+$ (A) and CD8$^+$ (B) lymphocytes. Fast-(F), Slow-(S), and Non-(N) proliferating cells are indicated.

Figure 18:
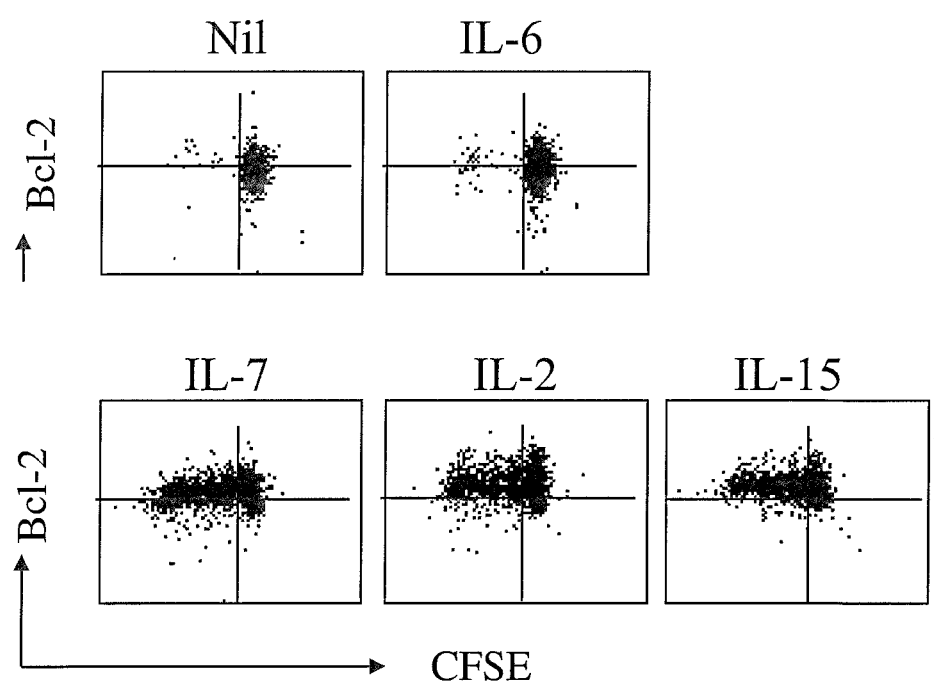

FIG. 18. IL-7, IL-2 and IL-15 drive optimal Bcl-2 expression on cultured human cells. Human PBMCs from healthy donors were labeled with the CFSE vital dye and cultured in the absence (nil) or in the presence of human recombinant IL-6, IL-7, IL-2 and IL-15 for 7 days. Cells were then stained with anti-CD4 mAb, fixed and intracellular Bcl-2 levels were determined by intracellular staining. Events are depicted after gating on CD4$^+$ T cells.

Figure 19:
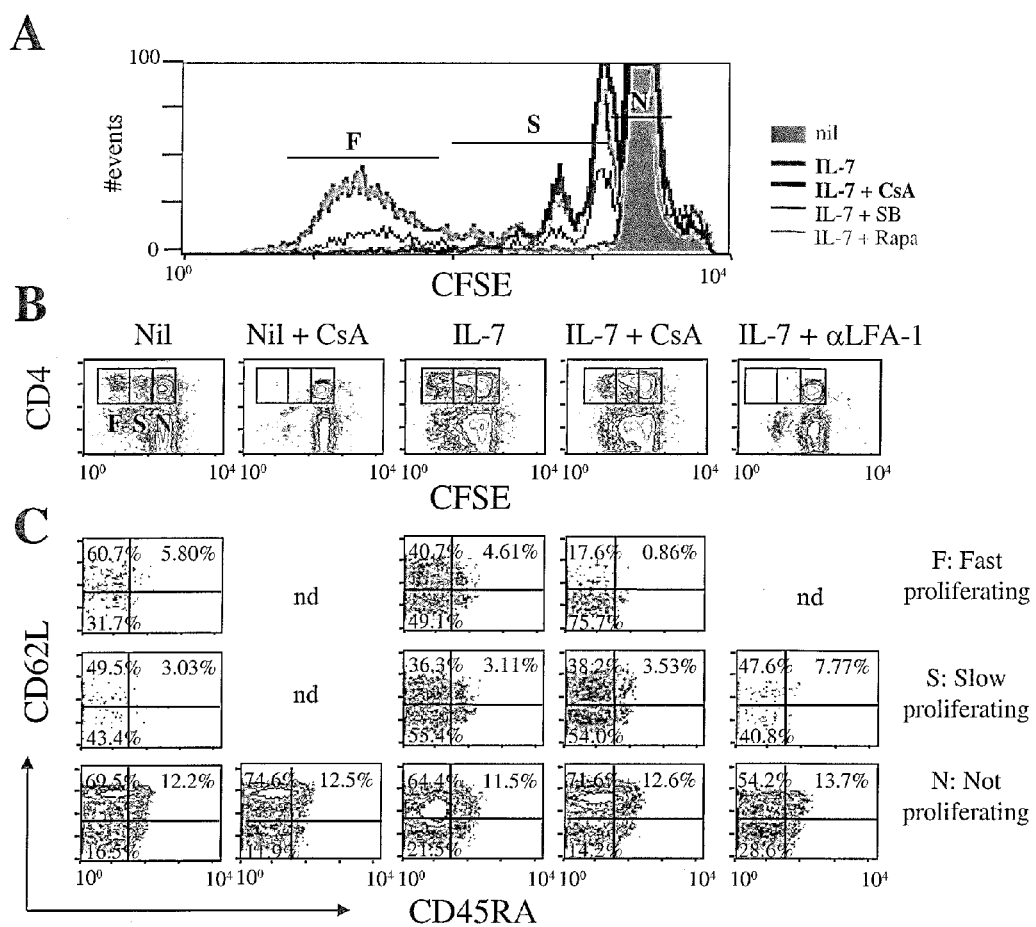

FIG. 19. IL-7-driven CD4 T cell proliferation of human peripheral blood memory CD4 T cells relies on CsA and LFA-1/ICAM-dependent signaling. Human PBMCs from healthy donors were labeled with the CFSE vital dye and cultured in the presence of human recombinant IL-7 for 7 days in the absence (nil) or in the presence of the indicated inhibitors. Cells were then stained with anti-CD4, antiCD45RA and anti-CD62L mAb and analyzed by flow cytometry. A) Histograms depict the overlay of the CFSE profiles of viable CD4$^+$ T cells. B) Dot plots depict viable CD4$^+$ T cells. Fast (F), Slow (S), and Non (N) proliferating cells were electronically defined and are shown in C. The relative representation of naive and memory T cells is indicated in the figure. Results are representative of 2 independent determinations.

Figure 20:
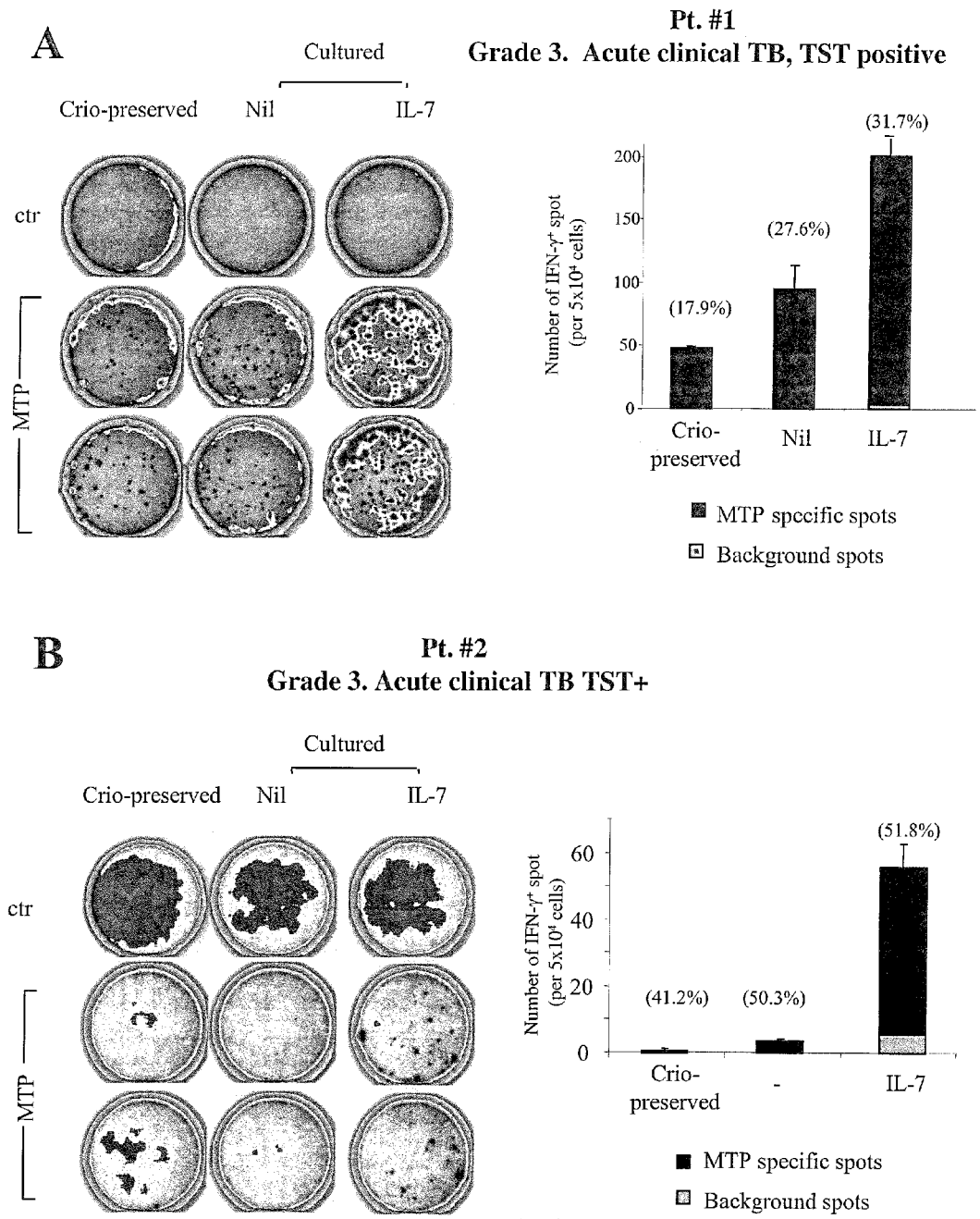
Figure 20:
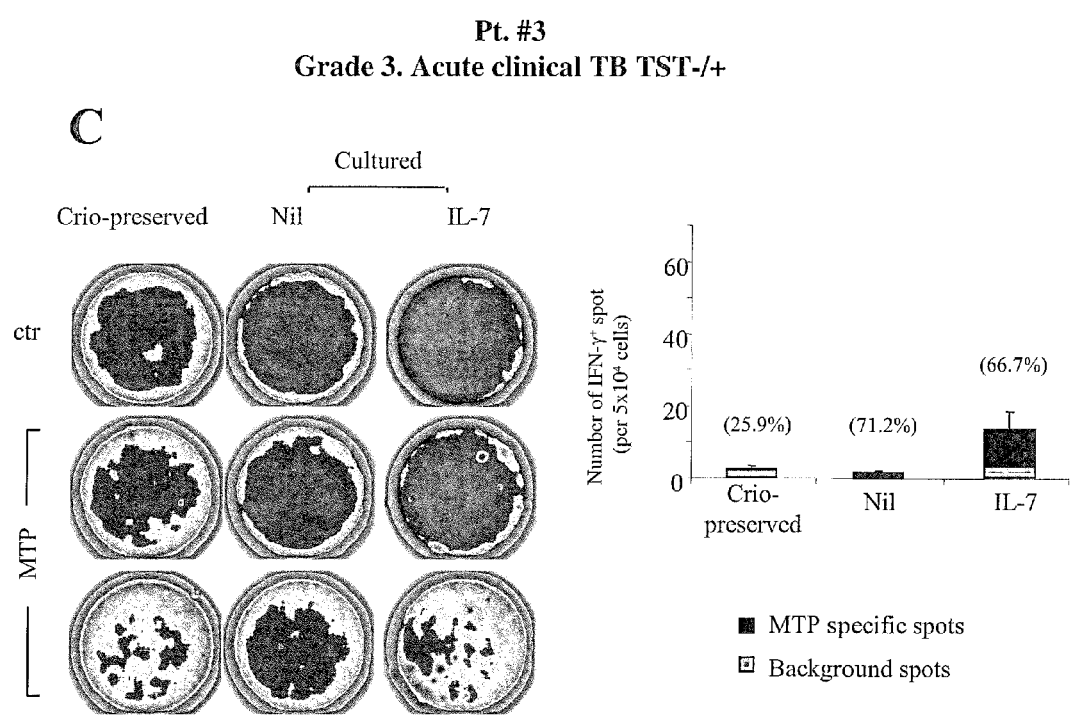

FIG. 20. Mycobacterium tuberculosis specific CD4$^+$ T cells are enriched for by IL-7-driven cultures. PBMC from three TB patients (Pt. #1, FIG. 20 A; Pt#2, FIG. 20 B; and Pt#3, FIG. 20 C) were analyzed for MTP-specific IFN-γ release by an ELISPOT assay at the time of thawing (crio-preserved) and after a 7 days culture in the absence (nil) or in the presence of human recombinant IL-7 (cultured). Background IFN-γ release was measured in unpulsed control wells (ctr). B) The total number of MTP-specific IFN-γ-producing cells is depicted.

Figure 21:
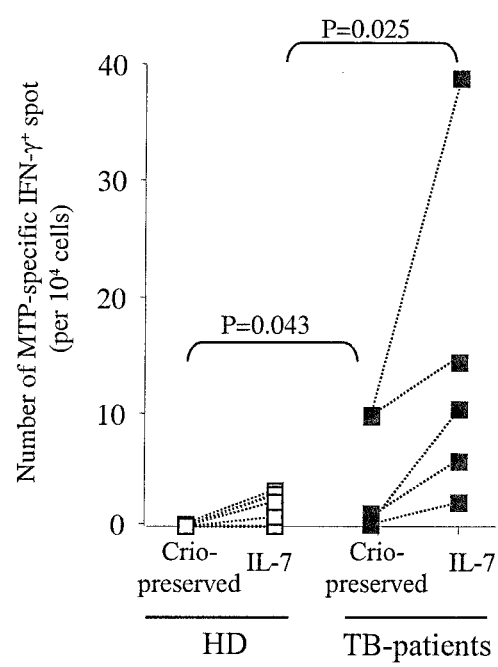

FIG. 21. The IL-7-driven culture facilitates the Identification of Mycobacterium tuberculosis specific CD4$^+$ T cells. MTP-specific IFN-γ production by crio-preserved and IL-7 cultured PBMCs derived from 8 healthy donors and 5 TB-patients were analyzed by ELISPOT. Statistical significance was evaluated by a paired two-tail T-test.

Figure 22:
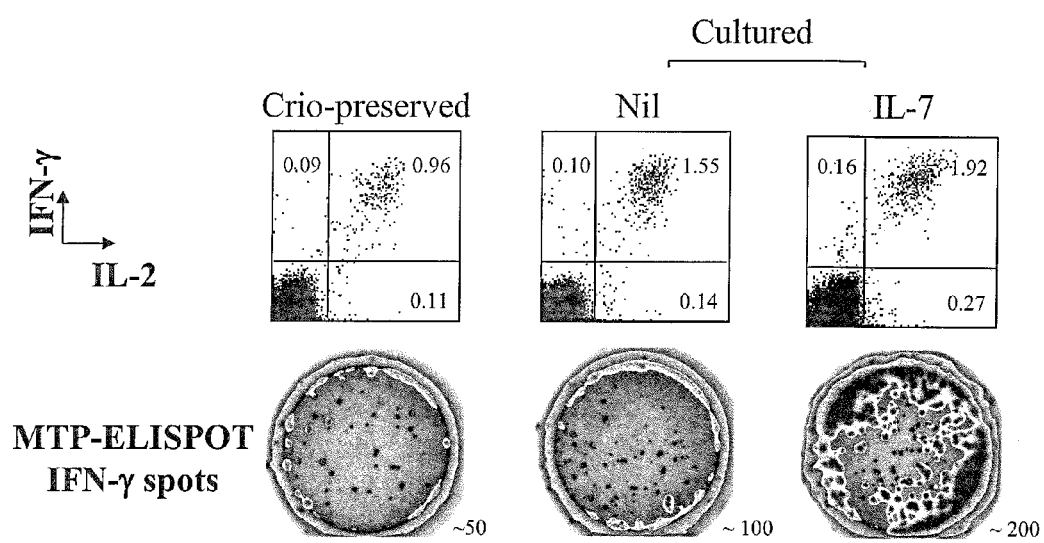

FIG. 22. Mycobacterium tuberculosis specific IL-2/IFN-γ$^+$ CD4$^+$ cells accumulate in IL-7 driven cultures. Pt#1 cells were cultured in the absence (nil) or in the presence of human recombinant IL-7 (cultured). A) MTP-specific IFN-γ release detected by ELISPOT (also depicted in FIG. 20A). B) A parallel set of cultured cells were also re-stimulated for 6 hours with MTP-pulsed autologous irradiated PBMC, surface stained with anti-CD4 mAb, fixed and further stained with anti-IFN-γ mAb. Events are depicted after gating on viable CD4$^+$ T lymphocytes.

Figure 23:
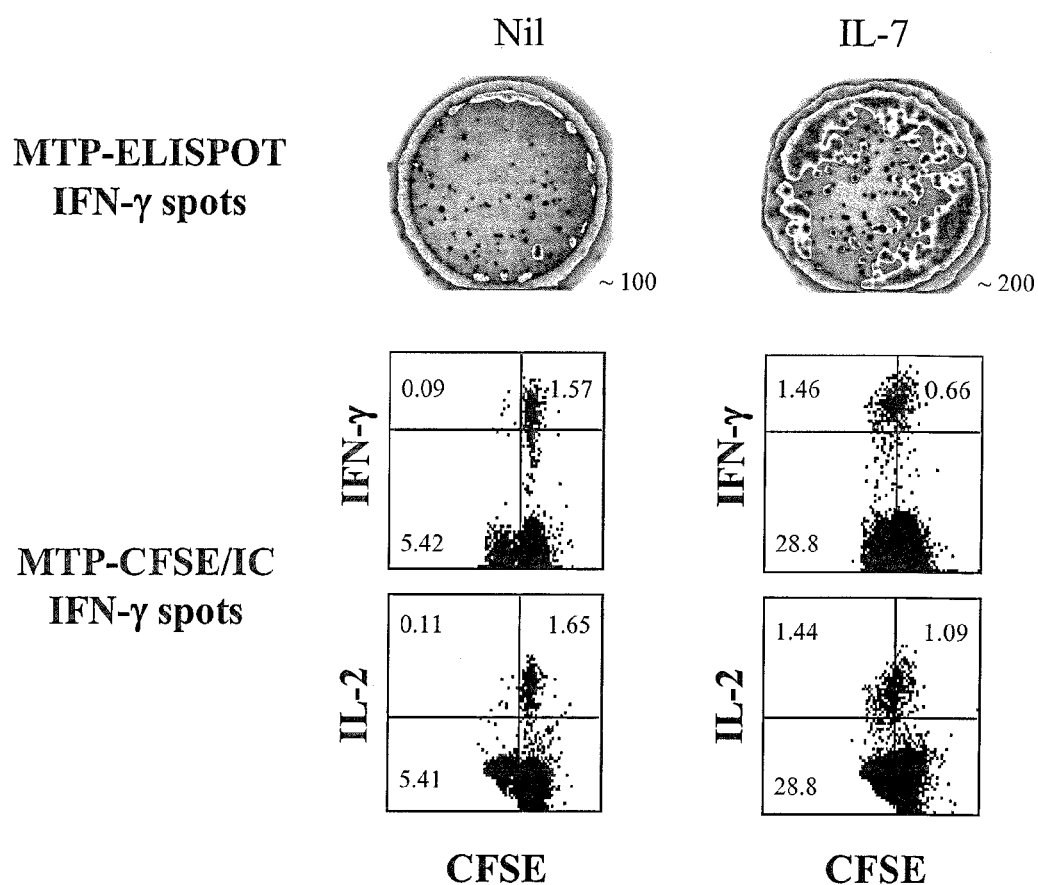

FIG. 23. Mycobacterium tuberculosis specific CD4$^+$ T cells proliferate in IL-7-driven cultures. A) Pt#1 cells were cultured in the absence (nil) or in the presence of human recombinant IL-7 (cultured). MTP-specific IFN-γ release detected by ELISPOT (also depicted in FIG. 20A). B) Parallel cultures were set up with CFSE-labeled PBMCs. After 7 days the cells were stimulated with MTP-pulsed autologous irradiated PBMCs, and intracellular IFN-γ release was determined by flow cytometry. Events are shown after gating on viable CD4$^+$ T cells.

Figure 24:
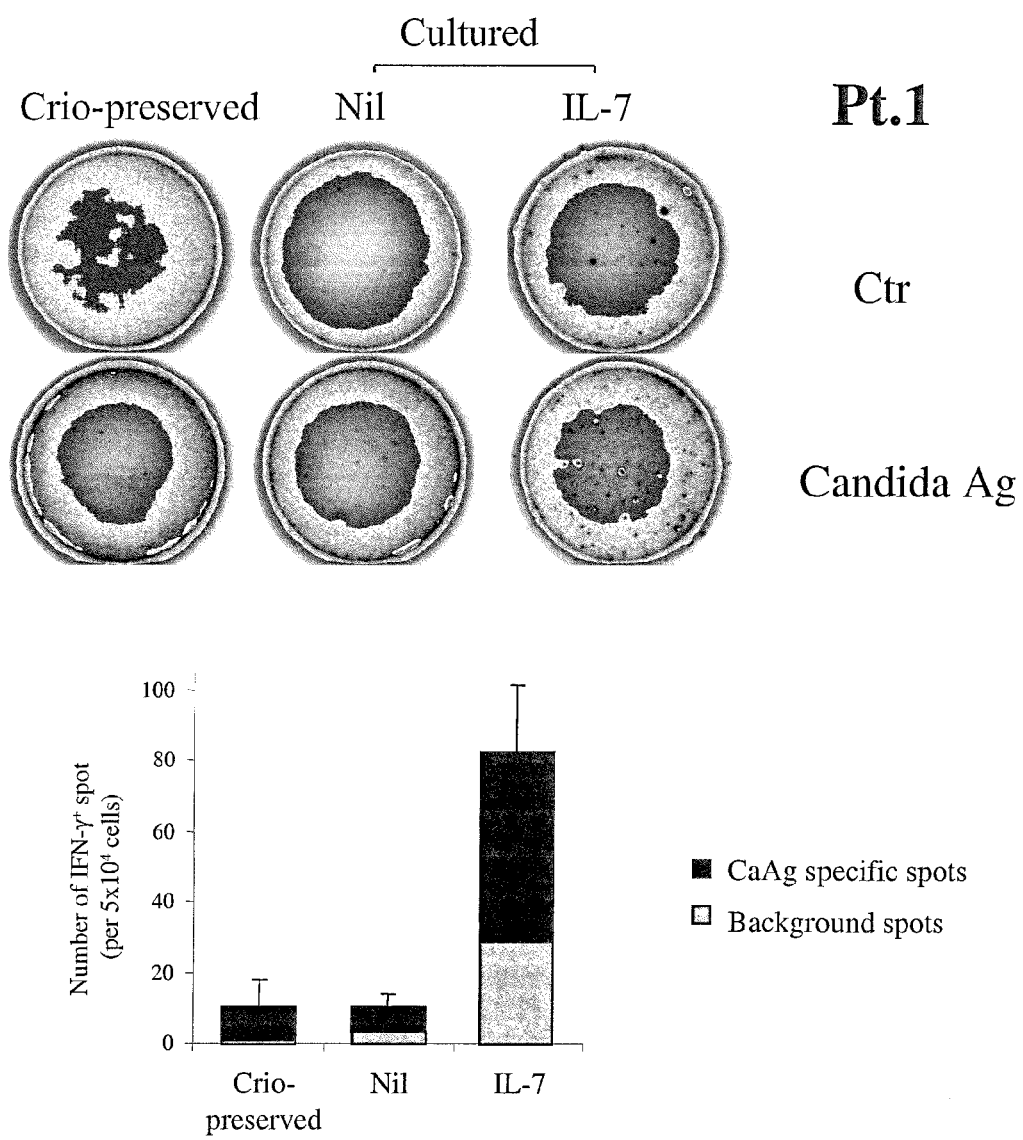

FIG. 24. Candida Albicans specific IFN-γ$^+$ memory T cells accumulate in IL-7-driven cultures. A) C. Albicans-specific IFN-γ release an ELISPOT assay by Pt#1 cells either crio-preserved or cultured for 7 days in the absence (nil) or in the presence of human recombinant IL-7 is depicted. Background IFN-γ release was measured in unpulsed control wells (ctr). B) The total number of IFN-γ-producing cells is depicted.

Figure 25:
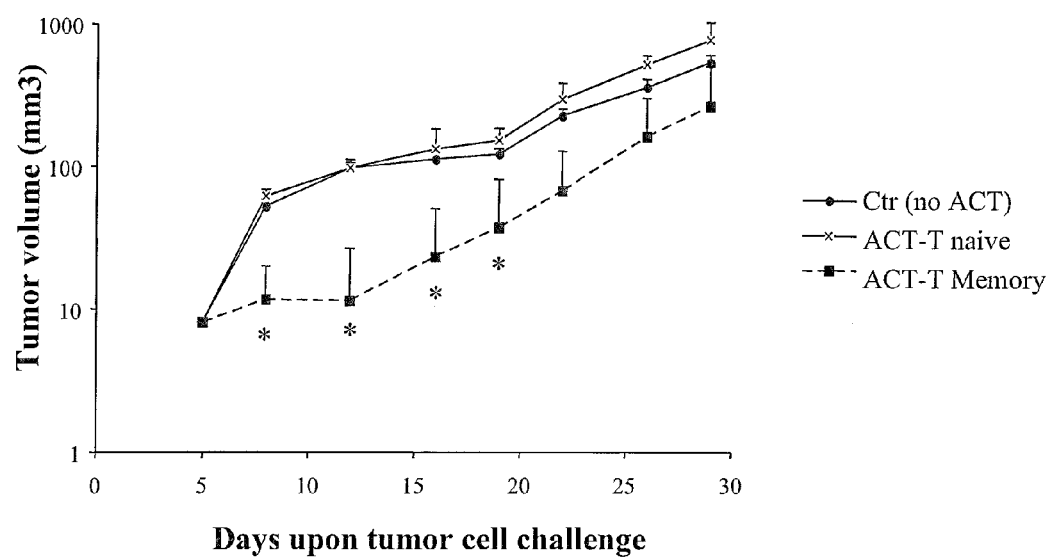

FIG. 25. IL-7/IL-15 cultured memory cells delays tumor growth upon adoptive cell transfer in vivo. Lymph nodes cells derived from control (naïve) and TS/A-LACK tumor-bearing mice were cultured for 7 days in high cell density (5×10$^6$ cells/ml) in the presence of IL-7 and IL-15 (both at 50 ng/ml). Thereafter 10$^7$ cultured cells adoptively transferred into naïve BALB/c mice. 48 hours later mice were challenged with 300.000 TS/A-LACK cells and tumor growth was monitored overtime. Statistical significance was evaluated by a paired two-tail T-test.

Figure 26:
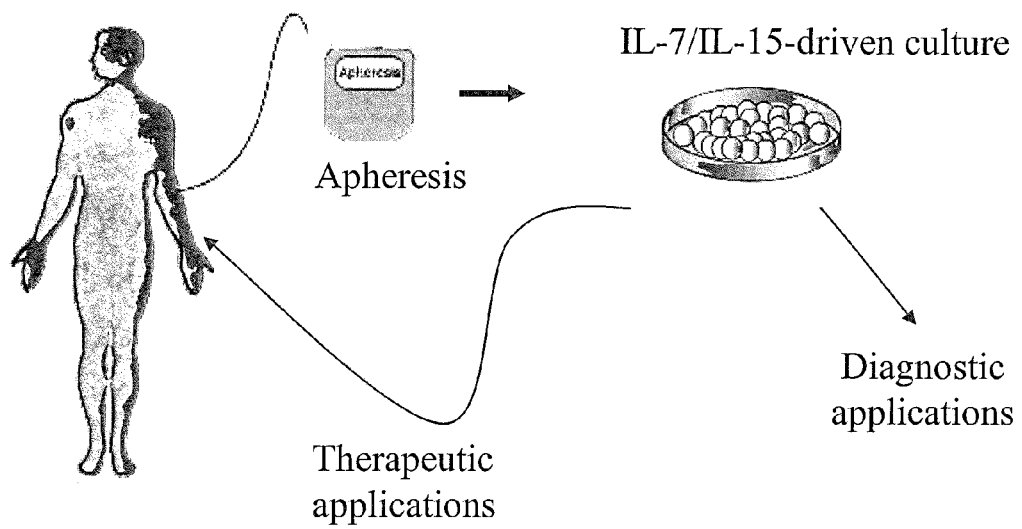

FIG. 26. Schematic representation of the proposed strategy and Its diagnostic and therapeutic implications.

Figure 27:
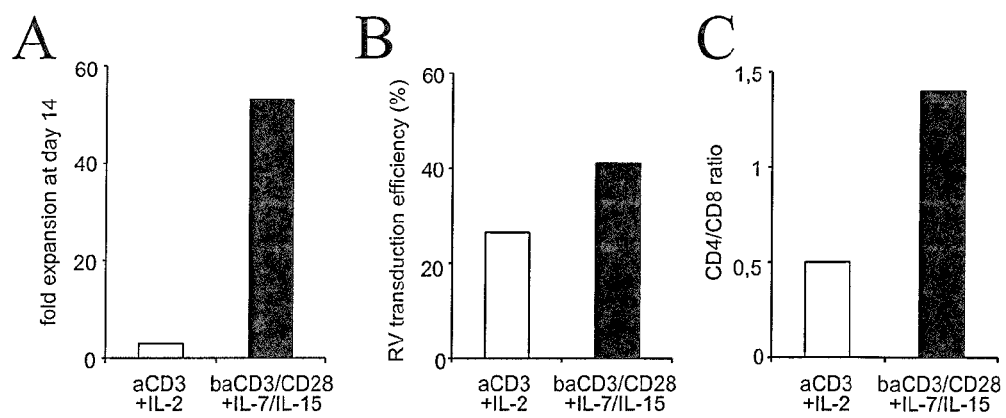

FIG. 27. Activation with beads conjugated with anti-CD3 and anti-CD28 antibodies (ba CD3/CD28) and culture with IL-7 and IL-15 promote T cell expansion and efficiently generate genetically modified human lymphocytes with a preserved CD4/CD8 ratio. 5×10$^6$ PBMC were stimulated either with aCD3 and cultured with IL-2 or with baCD3/CD28 and cultured with IL-7 and IL-15. At day 14, cells were counted by trypan blue exclusion. (A) Averages of T cell fold expansion in the two stimulation and culture conditions are reported (n=4 donors). 48 and 72 h after initial stimulation, cells were transduced by the SFCMM3 retroviral vector. At day 6, genetically modified cells were quantified by flow-cytometry after staining with anti-LNGFR antibodies. (B) Averages of transduction efficiency (in %) in the two stimulation and culture conditions are reported (n=4 donors). At day 14, cells were analyzed by flow-cytometry for ΔLNGFR expression and for the expression of CD4 and CD8. (C) Averages of CD4/CD8 ratio in genetically modified cells generated with the two protocols are reported (n=4 donors).

Figure 28:
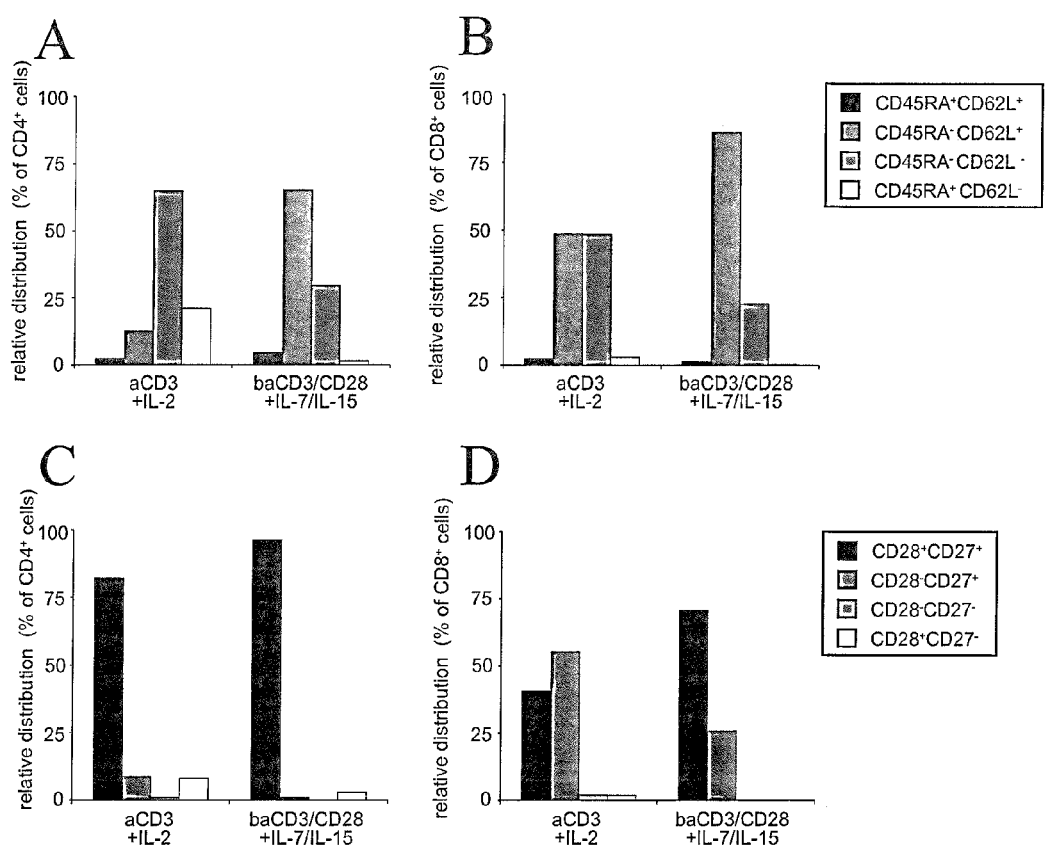

FIG. 28. Activation with baCD3/CD28 and culture with IL-7 and IL-15 generate TK$^+$ human lymphocytes with central memory phenotype. At day 14, TK$^+$ cells generated with aCD3 and cultured with IL-2 or generated with baCD3/CD28 and cultured with IL-7 and IL-15 were analyzed for memory phenotype. After gating for LNGFR expression, cells were analyzed by flow-cytometry for CD45RA and CD62L co-expression. Averages of the relative distribution (y axis, %) of CD45RA$^+$CD62L$^+$ (black bars), CD45RA$^-$CD62L$^+$ (dark grey bars), CD45RA$^-$ CD62L$^-$ (light grey bars) or CD45RA$^+$ CD62L$^-$ (white bars) are reported (A) for CD4 and (B) for CD8$^+$ cells obtained from n=4 donors. Cells were also analyzed by flow-cytometry for CD27 and CD28 co-expression. Averages of the relative distribution (y axis, %) of CD28$^+$CD27$^+$ (black bars), CD28$^-$CD27$^+$ (dark grey bars), CD28$^-$ CD27$^-$ (light grey bars) or CD28$^+$CD27$^-$ (white bars) are reported (C) for CD4$^+$ and (D) for CD8$^+$ cells obtained from n=4 donors.

Figure 29:
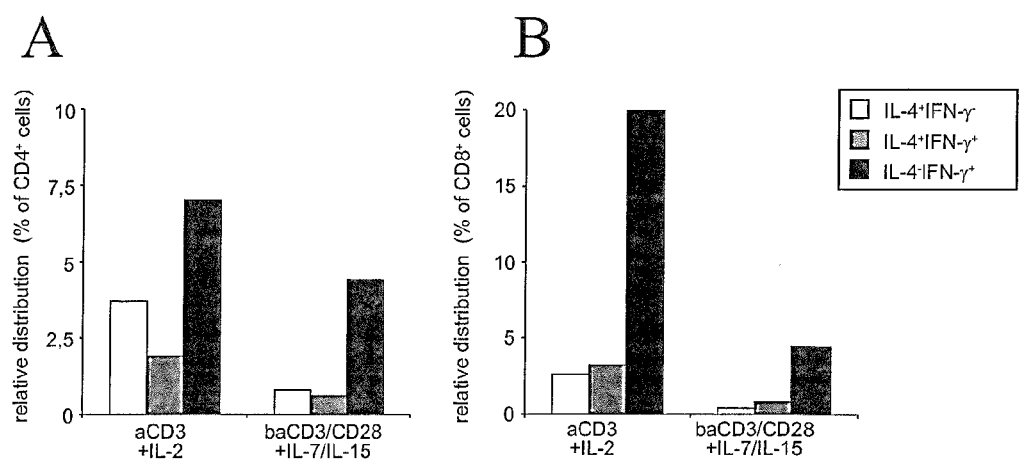

FIG. 29. Central memory TK$^+$ human lymphocytes are un-polarized cells. At day 14, TK$^+$ cells generated with aCD3 and cultured with IL-2 or generated with baCD3/CD28 and cultured with IL-7 and IL-15 were analyzed for cytokine production. After gating for ΔLNGFR expression, cells were analyzed by flow-cytometry for IFN-γ and IL-4 production. Averages of the relative distribution (y axis, %) of IL-4$^+$IFN-γ$^-$ (white bars), IL-4$^+$IFN-γ$^+$ (grey bars) or IL-4$^-$IFN-γ$^+$ (black bars) are reported (A) for CD4$^+$ and (B) for CD8$^+$ cells.

Figure 30:
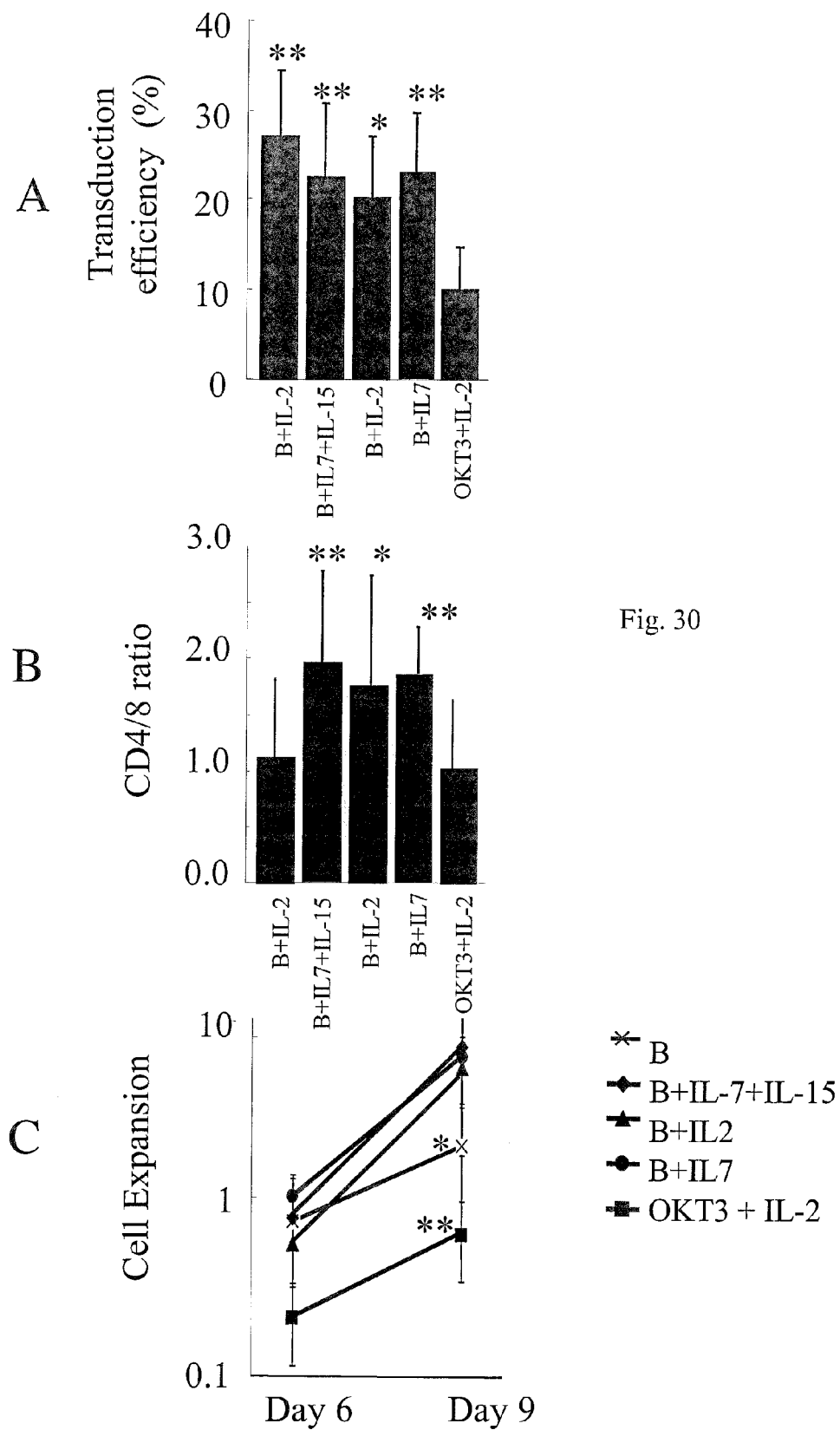

FIG. 30. Activation with beads conjugated with anti-CD3 and anti-CD28 antibodies and culture with IL-7+/−IL-15 or IL-2 promote T cell expansion and efficiently generate genetically modified human lymphocytes with a preserved CD4/CD8 ratio. PBMC were stimulated either with beads conjugated with anti-CD3 and anti-CD28 (named "B") and cultured with no cytokines, IL-7+IL-15, IL-2, or IL-7, or were stimulated with soluble anti-CD3 and cultured with IL-2. 48 and 72 h after initial stimulation, cells were transduced by the SFCMM3 retroviral vector. A) At day 6, genetically modified cells were quantified by flow-cytometry after staining with anti-LNGFR antibodies. Averages of transduction efficiency (in %) in the different stimulation and culture conditions are reported. B) At day 10, cells were analyzed by flow-cytometry for ΔLNGFR expression and for the expression of CD4 and CD8. Averages of CD4/CD8 ratio in genetically modified cells generated with the different protocols are reported. C) At days 6 and 9, cells were counted by trypan blue exclusion. Averages of T cell fold expansion in the different stimulation and culture conditions are reported (n=5 donors). *=p<0.05 **=p<0.01.

Figure 31:
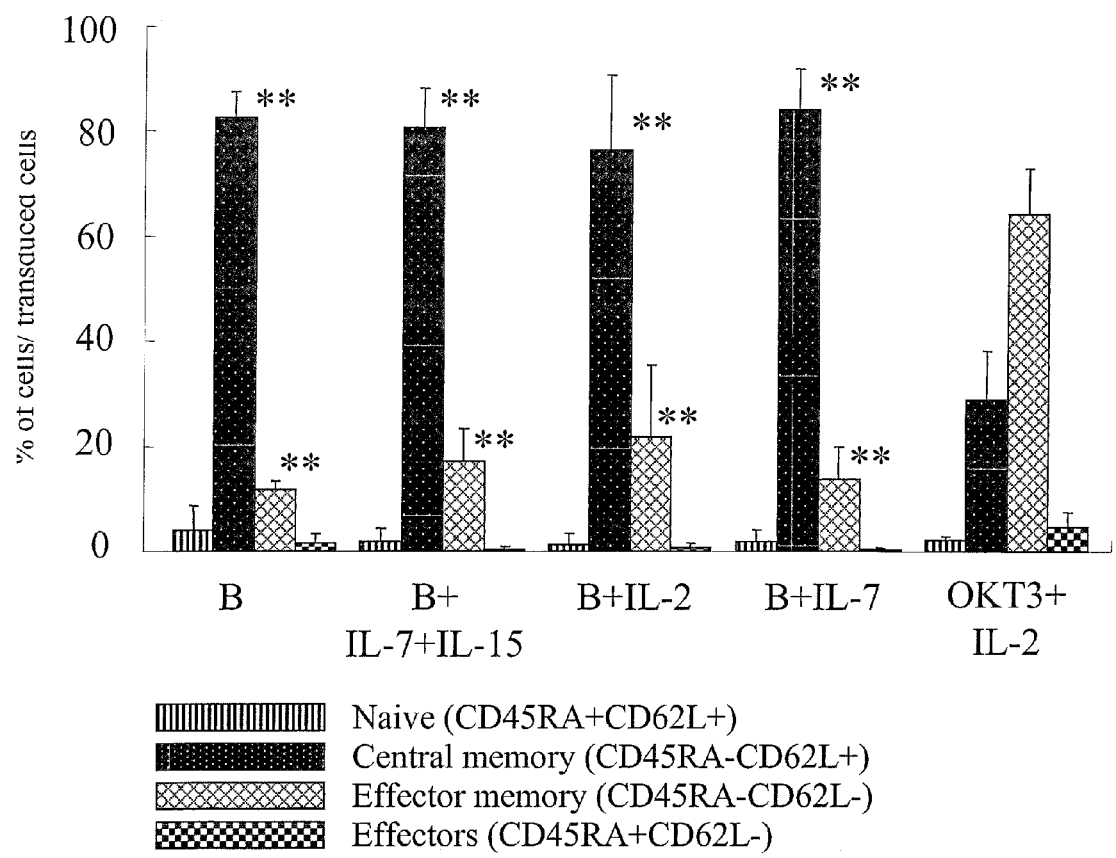

FIG. 31. Activation with beads conjugated with anti-CD3 and anti-CD28 antibodies and culture with IL-7+/−IL-IS or IL-2 generate transduced human lymphocytes with central memory phenotype. At day 10 transduced lymphocytes generated either with beads conjugated with anti-CD3 and anti-CD28 and cultured with no cytokines, IL-7+IL-15, IL-2, or IL-7, or stimulated with soluble anti-CD3 and cultured with IL-2 were analyzed for memory phenotype. Cells were analyzed by flow-cytometry for CD45RA and CD62L co-expression. Averages of the relative distribution (y axis, %) of CD45RA$^+$CD62L$^+$ (naïve cells), CD45RA$^-$CD62L$^+$ (central memory cells), CD45RA$^-$ CD62L$^-$ (effector memory cells) or CD45RA$^+$ CD62L$^-$ (terminally differentiated effectors) are reported on CD3+ ΔLNGFR+ cells. (n=−6 donors). *=p<0.05 **=p<0.01.

Figure 32:
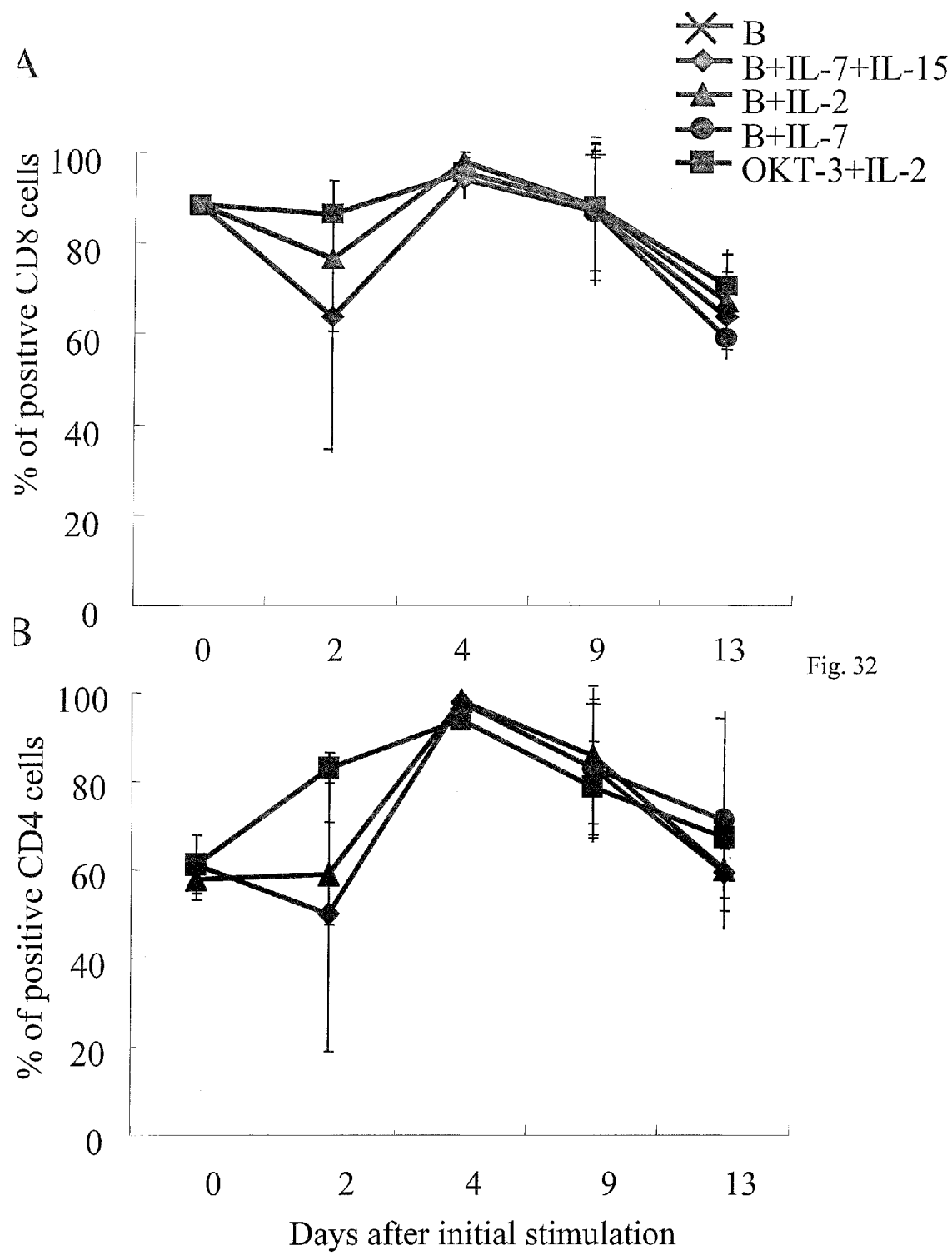

FIG. 32 kinetic of expression of IL-2/15 receptor β (CD122) does not depend from the activation, culture and transduction procedure. At days 0, 2, 4, 9 and 13, after initial stimulation, transduced lymphocytes generated either with beads conjugated with anti-CD3 and anti-CD28 and cultured with no cytokines, IL-7+ IL-15, IL-2, or IL-7, or stimulated with soluble anti-CD3 and cultured with IL-2 were analyzed for the expression of CD122. The % of CD3+ cells (at days 0, 2 and 4) and of transduced cells (at days 9 and 13) expressing CD122 at different time-points are reported on A) CD8+ and B) CD4+ cells. (n=4 donors).

Figure 33:
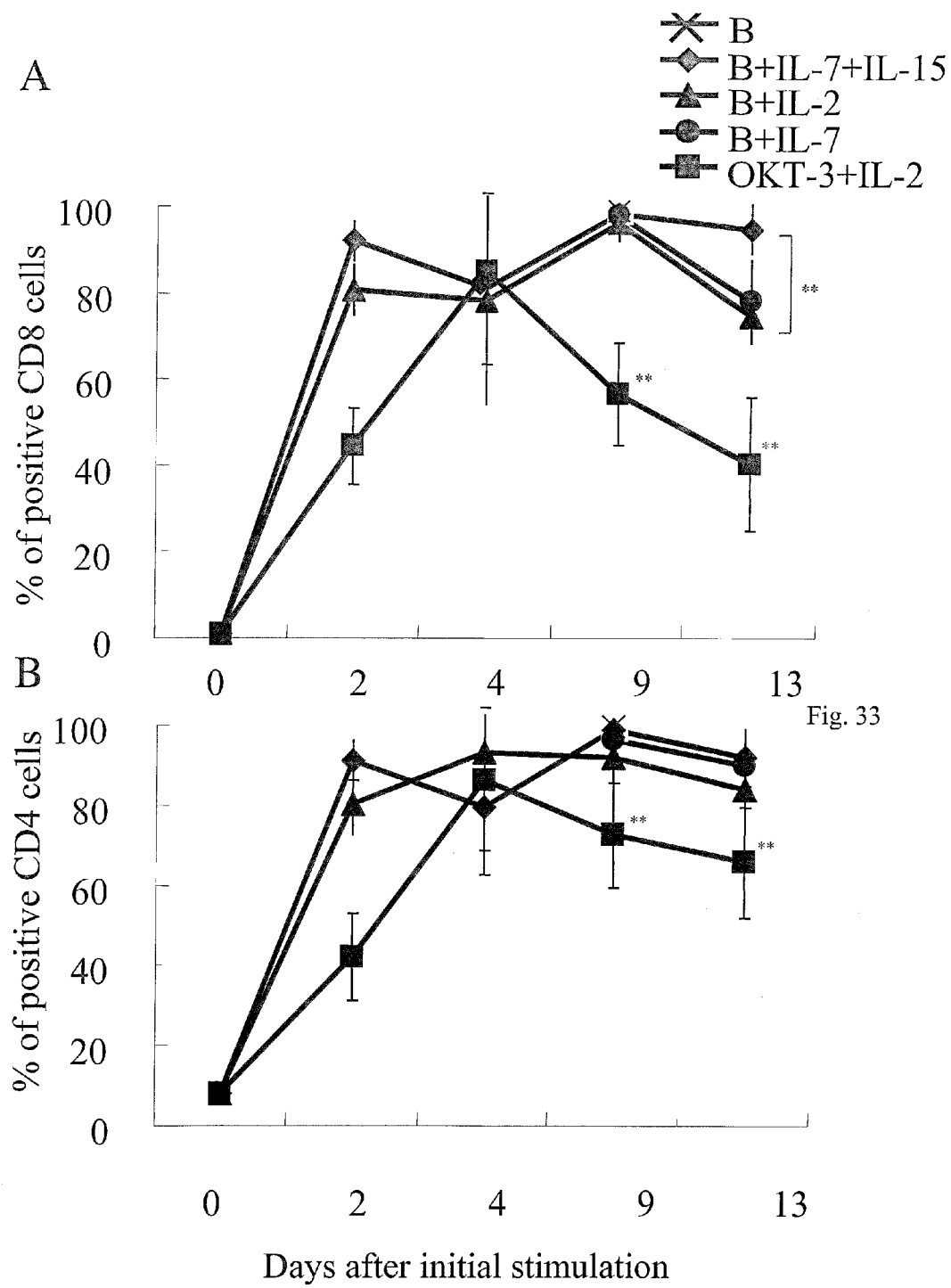

FIG. 33 Activation with beads conjugated with anti-CD3 and anti-CD28 antibodies and culture with IL-7+/−IL-15 or IL-2 promote intense and prolonged expression of IL-2 receptor α (CD25) on transduced lymphocytes. At days 0, 2, 4, 9 and 13, after initial stimulation, transduced lymphocytes generated either with beads conjugated with anti-CD3 and anti-CD28 and cultured with no cytokines, IL-7+ IL-15, IL-2, or IL-7, or stimulated with soluble anti-CD3 and cultured with IL-2 were analyzed for the expression of CD25. The % of CD3+ cells (at days 0, 2 and 4) and of transduced cells (at days 9 and 13) expressing CD25 at different time-points are reported on A) CD8+ and B) CD4+ cells. (n=4 donors). *=p<0.05 **=p<0.01.

Figure 34:
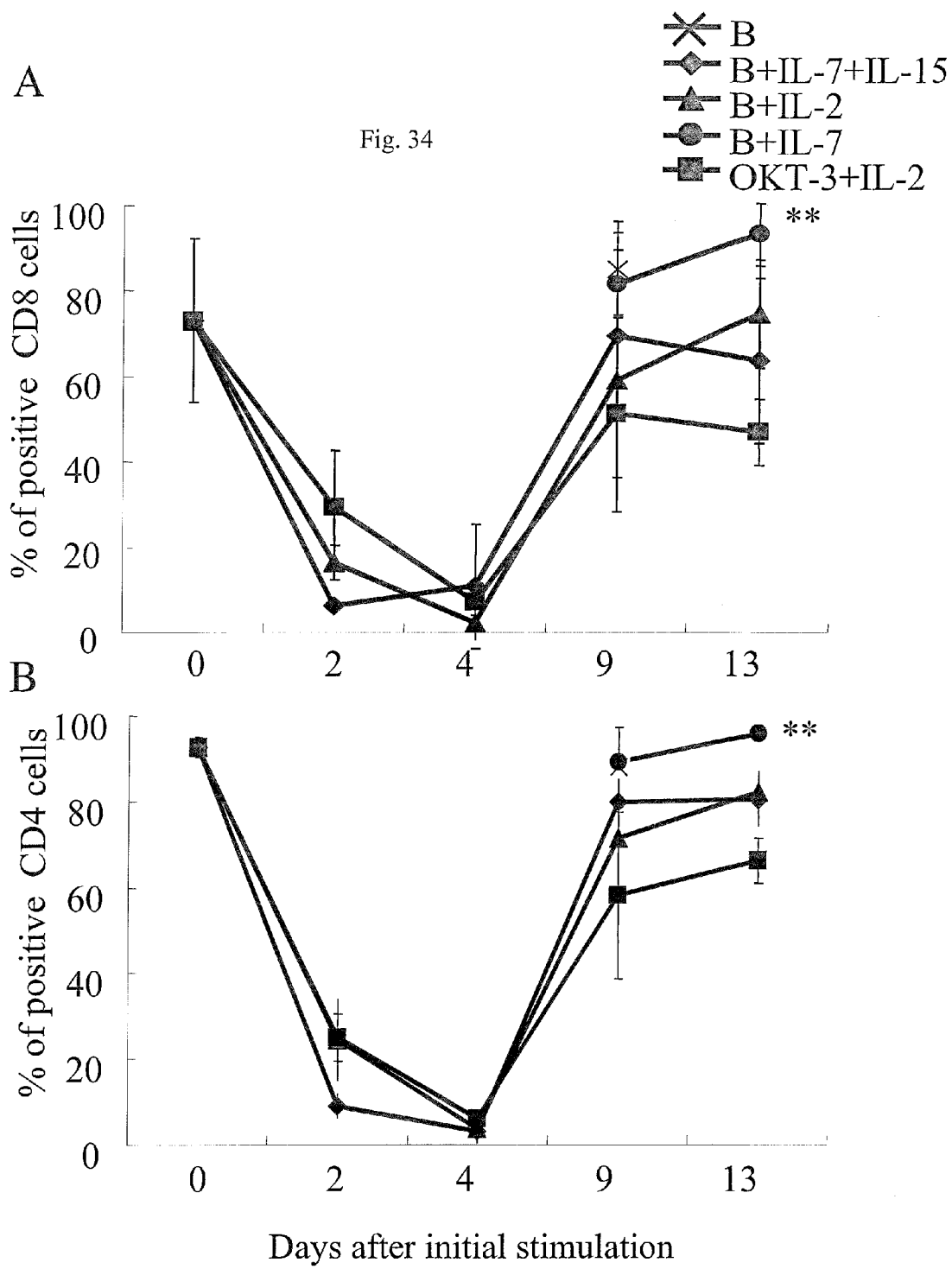

FIG. 34 Activation with beads conjugated with anti-CD3 and anti-CD28 antibodies and culture with IL-7 promotes intense and prolonged expression of IL-7 receptor α (CD127) on transduced lymphocytes. At days 0, 2, 4, 9 and 13, after initial stimulation, transduced lymphocytes generated either with beads conjugated with anti-CD3 and anti-CD28 and cultured with no cytokines, IL-7+ IL-15, IL-2, or IL-7, or stimulated with soluble anti-CD3 and cultured with IL-2 were analyzed for the expression of CD127. The % of % of CD3+ cells (at days 0, 2 and 4) and of transduced cells (at days 9 and 13) expressing CD127 at different time-points are reported on A) CD8+ and B) CD4+ cells. (n=4 donors). *=p<0.05 **=p<0.01.

FIG. 35 Activation with beads conjugated with anti-CD3 and anti-CD28 antibodies and culture with IL-7 preserves a high alloreactive proliferative potential and a low sensitivity to apoptotic signals in transduced cells.

Transduced T cells generated either with beads conjugated with anti-CD3 and anti-CD28 and cultured with IL-7 or IL-2, or by activation with soluble anti-CD3 and culture in IL-2 were stained with CFSE at day 9 after initial stimulation, and were co-cultured with irradiated allogeneic PBMCs. Unmanipulated peripheral blood lymphocytes (PBL) from the same donors were stained with CFSE, co-cultured with the same irradiated allogeneic PBMCs and used as controls. After 7 days cells were counted, stained with To-pro3, and analysed by FACS to evaluate the percentage of dividing and/or dying cells. A) Percentage of dividing cells. B) Total number of dying cells. Activation induced cell death was calculated on dividing cells (white, lower part of histograms) and death for neglect was calculated on non-dividing cells (black, upper part of histograms). *=p<0.05 **=p<0.01.

Figure 36:
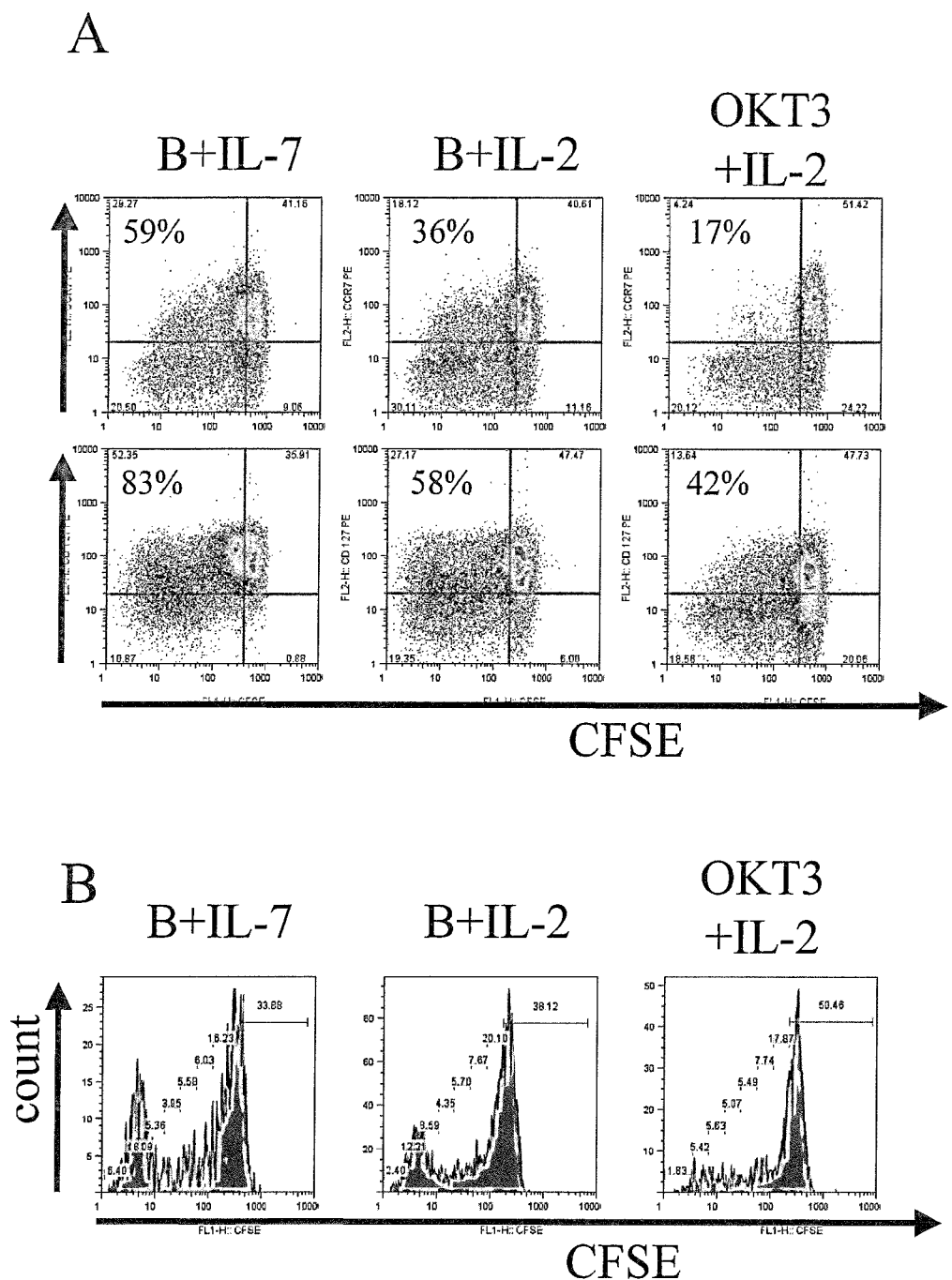

FIG. 36 Self-renewal capacity of central memory genetically modified cells generated with beads conjugated with anti-CD3 and anti-CD28 antibodies and culture with IL-7, after allogeneic stimulation.

A) Cells treated as described in FIG. 35 were analysed for the expression of CCR7 and IL-7Ra 7 days after the MLR was started. The percentage of CCR7+(upper panel) and IL-7Ra+ (lower panel) dividing cells is shown in the left upper quadrant. B) Cells were then re-challenge in vitro with the same allogeneic stimulators, following the same culture conditions utilized in the first stimulation. The percentage of dividing cells after the second stimulation is shown.

Figure 37:
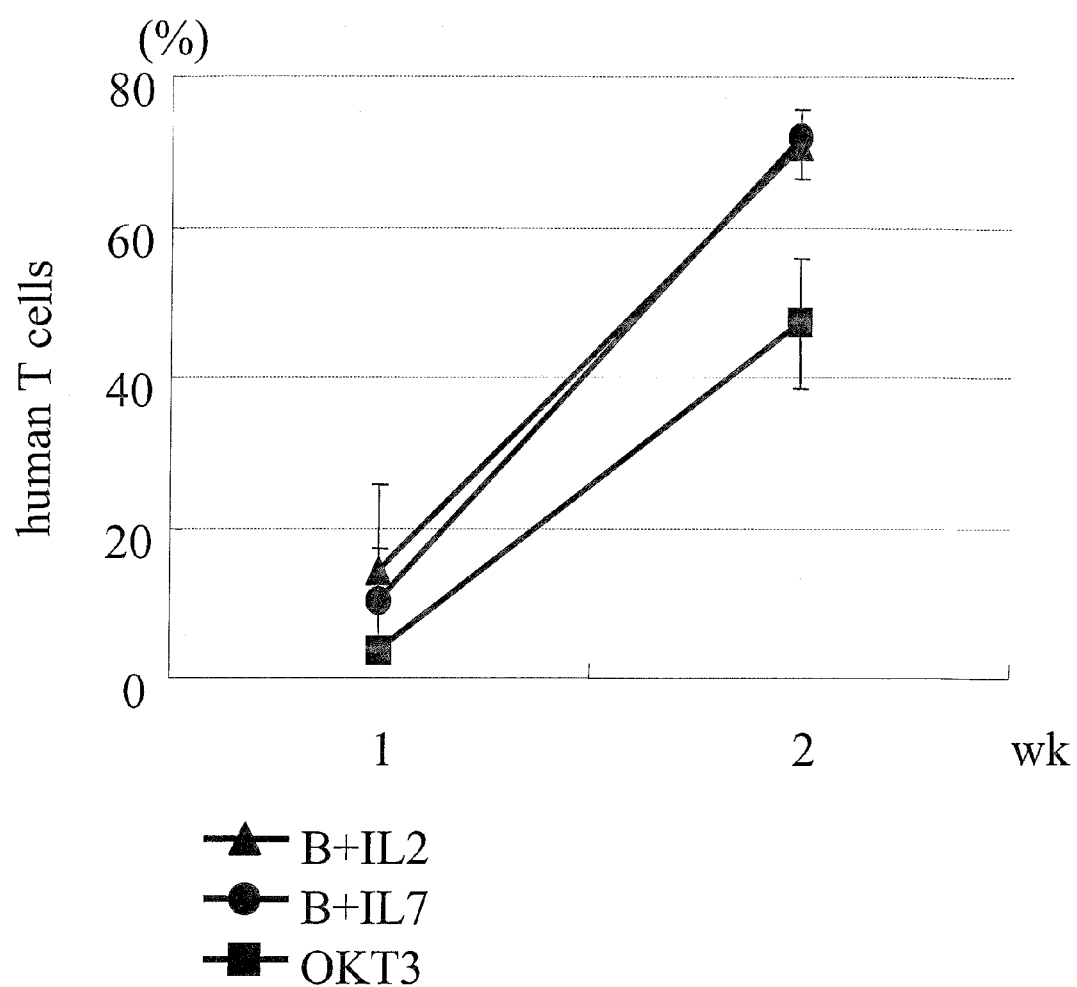

FIG. 37. Transduced lymphocytes generated with beads CD3/CD28 antibodies rapidly engraft in NOD/scid mice NOD/scid mice were conditioned and transplanted with human skin, were infused i.v. with $20 \times 10^6$ transduced lymphocytes generated with beads CD3/CD28 and culture with IL7 or IL2, or with OKT3 and culture with IL-2. Human chimerism was assessed weekly by flow-cytometry after staining for human CD3 and mouse CD45. Quadrants and percentages were set according to isotype control staining. Kinetic of human chimerism is shown (n=4 donors).

FIG. 38. Transduced lymphocytes generated with beads CD3/CD28 and cultured with IL-7 induce severe xenogenic GvHD in NOD/scid mice NOD/scid mice were conditioned and transplanted with human skin, were infused i.v. with $20 \times 10^6$ transduced lymphocytes generated with beads CD3/CD28 and culture with IL7 or IL2, or with OKT3 and culture with IL-2. Mice were monitored for xenogenic GvHD according 1) Weight loss. 2) GvHD clinical score (described in material and methods). Controls: animals that did not receive infusions of lymphocytes.

FIG. 39. Transduced lymphocytes generated with beads CD3/CD28 and cultured with IL-7 induce severe allogenic GvHD in NOD/scid mice Three weeks after human T-cell infusion, NOD/Scid chimera mice were sacrificed and human skin was removed bilaterally. All biopsies were subsequently blindly analysed by pathologists through ematossilin-eosin (EE) and anti human CD3 staining (αhCD3). Representative sections are reported.

MATERIALS AND METHODS

Experimental protocols were approved by the Ethical Committee of the San Raffaele Scientific Institute and performed according to its guidelines.

Mice and Tumor Cells

Seven to 8-week old BALB/c and CD45.2$^+$ C57BL/6 mice were purchased from Charles River (Charles River Italia, Milano, Italy). CD45.1$^+$ C57BL/6, DO11.10 and 16.2β Transgenic (Tg) (BALB/c background) (25) mice were bred in the Institute specific pathogen free facility. TS/A and TS/A-LACK mouse mammary adenocarcinoma were previously described (17, 19, 26). Exponentially growing $4 \times 10$ tumor cells were subcutaneously injected in 100 μl of PBS in the right flank of syngeneic mice (BALB/c). Typically, five mice per group were used in each experiment.

T Cell Primary Cultures

Twenty days after tumor cell injection mice were sacrificed and the axillary, brachial and inguinal peripheral lymph nodes (LN) draining and distal (non draining LN) to the site of tumor growth were recovered. In the experiments of dendritic cell (DC) vaccination, mice were sacrificed fourteen days after DC administration and the axillary, brachial and inguinal LN were surgically excised. LN cells were cultured in 24 well plates at the density of $5 \times 10^6$ in complete medium in the absence or in the presence of recombinant murine IL-7 (200 ng/ml), IL-2 (20 ng/ml), IL-6 (45 ng/ml), or IL-15 (100 ng/ml) (all from Peprotech). In parallel cultures, cells were in vitro stimulated with the LACK-derived MHC II-restricted peptide (5 μM, (25)) and $5 \times 10^6$ irradiated syngeneic splenocytes. As a control similar cultures were set up from syngeneic naïve mice. In some experiments, LN cells were labeled with the fluorescent dye CFSE (5-(and -6)-carboxyfluorescein diacetate, succinimilyl ester) at the final concentration of 1 μM accordingly to manufacturer instruction.

Dendritic Cell (DC) Preparation

Bone Marrow derived DC were obtained as previously described (18). Briefly, CD45.2$^+$ C57BL/6 bone marrow precursors were propagated for 7 days in complete Iscove's medium containing 25 ng/ml recombinant murine GM-CSF and 5 ng/ml recombinant murine IL-4 (Pharmingen, San Diego, Calif.). Then, BMDC were matured at 37° C. in the presence of LPS (1 μg/ml, Sigma, Milan, Italy) for 8 hours and pulsed for 1 hour with 10 μg/ml of the large T Ag-derived Tag IV peptide (18). DC maturation and purity were routinely evaluated by flow cytometry after staining with mAb recognizing CD11c, MHC class II, B7.1, B7.2 and CD40 molecules (all from Pharmingen). $2 \times 10^5$ pulsed mature DC were subcutaneously injected in 200 μl of PBS in the right flank of syngeneic C57BL/6 mice.

Flow Cytometry Analysis

I-A$^d$/LACK multimer staining was previously described. Briefly I-A$^d$/LACK dimers (MHC II-peptide complexes, 3 μg/sample) are multimerized by the addition of Alexa 488-coupled protein A (Molecular Probes Inc., Eugene, 0.3 μg/sample) in PBS for 30 minutes at room temperature. Free protein A binding sites were saturated by the addition of total IgG (1 μg/sample). $6 \times 10^5$ cells were first incubated with a blocking buffer (5% rat serum+95% culture supernatant of 2.4G2 anti-FcR mAb-producing hybridoma cells, 20 minutes) and then stained with the multimers (1 h at 4° C., in PBS supplemented with 0.5% BSA). The cells were then stained with anti-CD4, anti-CD44, anti-CD11b, anti-B220, anti-CD8a mAbs (PharMingen, San Diego, Calif., USA) and TO-PRO-3 (1 nM, Molecular Probes). $3 \times 10^5$ CD4$^+$ or $10^3$ CD4$^+$ I-A$^d$/LACK$^+$ events were collected by excluding all of the anti-CD11b$^+$, anti-B220$^+$, anti-CD8a$^+$ and TO-PRO-3$^+$ events. Where indicated the cells were surface stained with anti-CD4 or anti-CD8 mAb, and anti-CD44, anti-CD127, anti-CD25, anti-CD132 and anti-CD62L mAbs (all from PharMingen except anti-CD127 Ab, A7R34 clone, from Bioscience), and fixed, permeabilized and further stained with anti-Bcl-2 mAb according to to manufacturer instruction.

LACK-Specific Artificial Antigen Presenting Cells (aAPC) and Cytokine Secretion Assays 5 μm polystyrene sulfate latex beads (Interfacial Dynamics) were coated with I-A$^d$/LACK dimers (20 μg/ml) and anti-CD28 mAb (37.51; 2 μg/ml) (LACK aAPC) or with anti-CD28 mAb only (control aAPC). Coating of the proteins was monitored by flow cytometry analysis. Typically $5 \times 10^5$ LN cells were cultured with $5 \times 10^6$ aAPC for 5 hours at 37° C. Brefeldin A (5 pig/ml, Sigma) was added to the cultures for the last 2 hours. Cytokine release induced by LACK aAPC was comparable to the one induced by LACK-pulsed syngeneic splenocytes (not shown). In the case of AH-1 and Tag IV-induced cytokine production, splenocytes were derived from DO11.10 and CD45.1$^+$ C57BL/6 mice and used as antigen presenting cells. Splenocytes ($3 \times 10^7$ cells/ml) were pulsed with 1 μM AH-1 (19) and 10 μg/ml Tag IV (18) peptides for 1 hour at 37° C. and then used to stimulate syngeneic LN cells derived from the LN of tumor-bearing mice and DC-vaccinated mice, respectively. Thereafter the cells were stained with anti-CD8, and IL-2 and IFN-γ as described above and with the anti-clonotipic KJ1.26 mAb, and the anti-CD45.1$^+$ marker to exclude T cells of APC origin. CD4$^+$, KJ1.26$^-$ or CD8$^+$ CD45.1$^-$ events were then collected on a FACS Calibur. The total number of Ag-specific IL-2$^+$/IFN-γ$^+$ T cells was determined by multiplying the percentage by the total number of Trypan Blue-negative LN cells.

Human T Cell Cultures and ELISPOT Assay.

Peripheral blood mononuclear cells (PBMC) were obtained from patients with tuberculosis (TB) and healthy donors by blood centrifugation over Fycoll-Hypaque density gradient and analyzed right away or frozen for future analysis. Where indicated cells were stained with CFSE (1 μM). Cells were cultured in the absence or in the presence of human IL-7 (200 ng/ml), IL-2 (20 ng/ml, IL-15 (100 ng/ml) or IL-6 (45 ng/ml) for 7 days. Where indicated Ciclosporin A (CsA) (0.5 μg/ml) or anti-LFA-1 (5 μg/ml) blocking antibody were added. Cells were then harvested and stained with CD4, CD8, CD3, CD56, CD45RA, CD62L mAbs (all from PharMingen) and analyzed by flow cytometry.

The ELISPOT assay for IFN-γ secretion was performed as previously reported (28). Briefly cells were seeded in duplicate at 5×10$^4$ cells/well in 96-well plates (MAIPS4510; Millipore, Bedford, Mass.) pre-coated with anti-IFN-γ capture mAb (B-B1; Diaclone, Besanon, France) in the presence of autologous irradiated PBMC (5×10$^4$ cells/well), and a pool of MTP peptides for 18 h at 37° C. in air plus 5% CO$_2$. Biotinylated anti-IFN-γ detection mAb (B-G1; Diaclone) was added for 4 h, followed by the addition of streptavidin-alkaline phosphatase conjugate (Amersham Pharmacia Biotech Europe GmbH, Freiburg, Germany) for 1 h. After a washing step, the nitroblue tetrazolium-BCIP (5-bromo-4-chloro-3-indolylphosphate; Sigma, St. Louis, Mo.) chromogenic substrate was added. Individual spot forming cells (SFC) were counted using an automated image analysis system ELISPOT reader (AID-GmbH, Strassberg, Germany). A pool of six synthetic *Mycobacterium tuberculosis* peptides (MTP; Primm srl, Milano, Italy) with a length of 20 amino acids, >70% purified, derived from the sequences of ESAT-6 and CFP-10 secretory proteins of *M. tuberculosis* were used at a final concentration of 2 μg/ml per peptide for the detection of a specific response (28). PBMCs in medium alone or stimulated with phytohaemagglutinin (PHA-P; Sigma) 5 μg/ml were respectively used as negative and positive controls.

In some instances, MTP-specific IFN-γ release was analyzed at the single cell level by intracellular cytokine secretion assay, Briefly, 0.6×10$^6$ CFSE labeled cells-were re-stimulated for 6 hours in the presence of human anti-CD28 stimulating mAb (2 μg/ml) and 3×10$^6$ autologous irradiated (5000 rad) PBMCs pulsed with HLA-DR-restricted MTP (4 μg/ml) or left unpulsed, in negative controls. In the last 5 hours Brefeldin A (10 μg/ml) was added to the cells. Thereafter the cells were fixed, permeabilized and stained with anti-CD4, anti-IL-2 and anti-IFN-γ mAbs and analyzed on a FACS Calibur.

Classification of TB Patients.

Five HIV-seronegative patients with active TB (clinic and culture confirmed) were recovered at the Clinic of Infectious Diseases, S. Raffaele Hospital. They underwent tuberculin skin test (TST) administered by the Mantoux method with 0.1 ml (5 tuberculin units) of Biocinetest-PPD tuberculin (Chiron Italia srl, Milano, Italy). The size of induration was evaluated after 48-72 hours (an induration ≥10 mm was classified as positive). Peripheral blood was withdrawn before starting any therapy and with a previous written informed consent. Healthy controls (n=8) were selected among HIV-seronegative individuals with no history of TB exposure, no infection and with negative reaction to the TST.

Activation, Culture and Retroviral Transduction of Human T-Cells

Peripheral blood mononuclear cells (PBMC) were isolated by Lymphoprep gradient separation from buffy coats of healthy donors obtained after informed consent (Fresenius, Oslo, Norway). PBMC were cultured in RPMI1640 medium (GIBCO-BRL, Gaithersburg, Md.) supplemented with antibiotics, glutamine and with 10% heat-inactivated FBS (Bio-Whittaker-Italia, Milano, Italy). PBMC were seeded in 6-well plates (1×10$^6$/ml) and activated with anti-aCD3 (OKT3 30 ng/ml, OrthoBiotech, Raritan, N.J.) or paramagnetic baCD3/CD28 (3:1 beads/T-cell) (Dynabeads, Dynal Biotech, or Xcyte Therapies Inc., Seattle Wash., USA, Invitrogen). T-cells were enriched by baCD3/CD28 before culture. Cells activated with aCD3 were cultured with human recombinant IL-2 at 600 IU/ml (Chiron, Emeryville, Calif.).

Cells activated with baCD3/CD28 were cultured: 1. In the absence of cytokines; 2. with human recombinant IL-7 at the minimal concentration of 5 ng/ml (Peprotech, London, UK); 3. with human recombinant IL-7 and IL-15 both at the minimal concentration of 5 ng/ml each (Peprotech, London, UK). At day 2 and 3, cells were transduced with the SFCMM3 (39-40) retroviral supernatant by spinoculation at 2400 rpm for 2 h at 37° C. with 8 μg/ml polybrene (Sigma, St Louis, Mo.). The SFCMM3 retroviral vector encodes for the TK suicide gene under the LTR promoter and for a truncated form of the low affinity receptor for nerve growth factor (ΔLNGFR) under the SV40 promoter (27). The retroviral supernatant was provided by Molmed s.p.a. At day 6 after T-cell activation, cell-sized beads used for the stimulation were removed from T-cells, according to manufacturer's instructions. In some experiments, at day 7 after T-cell activation, transduced lymphocytes were positively selected according to the protocol that follows (protocol entitled: Positive immuneselection of transduced lymphocytes).

Cells were cultured up to 14 days. At day 14, fold expansion was calculated by multiplying the percentages of LNGFR$^+$ cells determined by flow-cytometry with the trypan blue counts. Medium and cytokines were replaced, according to the initial protocol, every 3-4 days. At selected time-points, fold expansion was calculated by multiplying the percentages of ΔLNGFR$^-$ cells determined by flow-cytometry with the trypan blue counts.

Positive Immuneselection of Transduced Lymphocytes

At day 7 after T-cell activation transduced lymphocytes were positively selected. Since transduced cells expressed ΔLNGFr on their surface, anti-LNGFr antibodies covered with magnetic beads were used to separate transduced from untransduced lymphocytes. Cells were collected from plates in tubes, washed (1500 rpm, 10 min. at room temperature-RT) and resuspended in WB at a final concentration of 5×10$^6$/ml. Anti-LNGFr antibody 20.1 was then added to the cell suspension (10 g/20×10$^6$) and cells were placed to rotate at 10 rpm for 30 min at RT. T-cells were then washed once and resuspended in WB at 25×10$^6$/ml. Dynabeads M-450 Sheep anti-Mouse IgG were then added (5×10$^6$ beads/10$^6$ positive cells) and cells were placed to rotate at 10 rpm for 30° at room temperature. Transduced cells were then magnetically selected. To this purpose, tubes were placed near the magnet for 3 min and the negative fraction was discarded. This procedure was repeated for a total of three times. Finally the fraction of cells bound to the beads was removed from the magnet, washed, and resuspended in fresh medium with the appropriate cytokine cocktail at a concentration of $1\times10^6$ cells/ml.

Flow Cytometry of Transduced T-Cells

Flow cytometry was used for analysis of surface phenotype, transduction efficiency, cell cycle, and cytokine production. The following antibodies (Pharmingen) were used: FITC-conjugated mAb to human CD4, CD8, CD45RA, CD27 and IFN-γ, (PE)-conjugated mAb to human CD4, CD8, LNGFR, CD62L, CD28 and IL-4, peridinin chlorophyll-a protein (PerCP)-conjugated mAb to mouse CD45 (Ly5.1), and allophycocyanin (APC)-conjugated mAb to human CD3 Samples were run through a Facscalibur flow-cytometer (Becton Dickinson, Mountain View, Calif.) after isotype-matched fluorochrome-conjugated irrelevant mAb-stained control and data were analyzed using CellQuest Software (Becton Dickinson). Fluorochrome-conjugated antibodies to CD127, CD122, CCR7, and to mouse CD45 (Pharmingen, San Diego, Calif., USA) were also utilized to stain lymphocytes.

Cytokine Production

For determination of cytokine production, cells were seeded in 24-well plates ($1\times10^6$/ml) and stimulated with 50 ng/ml PMA (Sigma) and 1 g/ml ionomycin (Sigma). After 4 h, brefeldin A (Sigma) were added for additional 2 h (0 μg/ml). Cells were then stained with the appropriate fluorochrome-conjugated anti-surface marker antibodies and fixed with 1% para-formaldehyde at 4° C. for 10 min. Intracellular staining was performed with the appropriate fluorochrome-conjugated anti-cytokine antibodies after incubation for 20 min at RT in PBS 2% FBS containing 0.05% saponin (Sigma).

CFSE Dilution Assay and Mixed Lymphocyte Reaction (MLR)

Analysis of T-cell alloreactivity was performed at day 10 after initial culture of lymphocytes. Transduced T-cells were stained with CFSE at day 10, and then cultured with irradiated allogeneic PBMCs. CFSE consists of a fluorescein molecule containing a succinimidyl ester functional group and two acetate moieties. CFSE diffuses freely into cells and intracellular esterases cleave the acetate groups converting it to a fluorescent, membrane impermeant dye. The dye is not transferred to adjacent cells. CFSE is retained by the cell in the cytoplasm and does not adversely affect cellular function. During each round of cell division, the relative intensity of the dye decreases by half.

CFSE Staining Procedure:

Cells were washed twice in PBS (in the absence of serum) and adjusted to $2\times10^7$/ml. CFSE was diluted to 1 μM in PBS and mixed with the cell suspension at a 1:1 ratio. Cells were vortexed quickly, and mixed for 8 min. at RT. FBS was then added at a 1:1 ratio and 1 minute later cells were centrifuged at 2000 rpm for 2 min. Supernatant was then discarded, cells washed twice with a 10% FBS containing solution (PBS or medium).

MLR

At the end of the procedure, CFSE-stained transduced T-cells (responders) were placed in culture in 24-well-plates with 2000 cGy irradiated allogeneic PBMCs (stimulators) in a 1:1 ratio. No cytokines were added to cell culture. CFSE-stained transduced T-cells placed in culture in the absence of stimulators were used as negative control. Cells placed in culture with soluble anti-CD3 antibody were used as positive control.

Read-Outs

At selected time points after stimulation, cells samples were collected and stained with fluorochrome-conjugated anti-surface markers monoclonal antibodies. Immediately before FACS acquisition, 1 μl To-Pro-3 solution was added to each FACS sample. To-Pro-3 is a high red intercalating DNA dye, detectable in fluorescence 4, which offers the possibility to co-stain cells with FITC, PE and APC conjugated antibodies. Its function is to reveal the dead cell fraction.

In Vivo Analyses

Mice with immunological defects in the adaptive (scid, recombination-activating genes$^{-/-}$) as well as in the innate compartment (NOD, common γ chain$^{-/-}$) are commonly used to study human lymphocyte biology in vivo. We utilized NOD/scid mice to test the activity of central memory genetically modified lymphocytes in vivo. Six- to 8-week-old female NOD/scid mice were obtained from Charles-River Italia (Calco, Italy). The experimental protocol was approved by the internal committee for animal studies of our Institute (Institutional Animal Care and Use Committee [IACUC]). Mice were treated according to the following protocols:

Xenogenic Graft-Versus-Host Disease Model 6-8 weeks old female NOD/scid mice were obtained from Charles-River Italia (Calco, Italy). One week before infusion, mice were transferred from laminar-flow isolators to normal cages and kept under specific pathogen-free conditions receiving sterile water and irradiated pellets ad libitum. The day before the experiment, mice were given 1 mg blocking anti-mouse IL-2R β monoclonal antibody i.p. to neutralize residual NK activity. The anti-IL2Rβ antibody was produced as described from the TMβ-1 hybridoma kindly provided by Prof. Tanaka (Osaka University, Japan). At day 0, mice received total body irradiation with a single dose of 350 cGy (gamma irradiation from a linear accelerator) and were immediately infused with unmodified PBL or human lymphocytes transduced with the SFCMM3 retroviral vector (28). Unmodified PBL were obtained from PBMC after the depletion of contaminating monocytes, B- and NK-cells with Pan T-cell isolation kit (Miltenyi, Bergisch Gladbach, Germany). Cells were re-suspended in 500 μl X-VIVO15 medium and infused i.p. Mice were then monitored for GvHD by calculating weight loss. Moribund mice were sacrificed for ethical reasons. Human chimerism was determined weekly by flow-cytometry after bleeding from the tail vein. Human chimerism was calculated as follows: human chimerism (%)=[huCD3$^+$/(huCD3$^+$+mCD45$^+$)]×100.

Analysis of Xenogenic GvHD

At week 1, 2 and 3 after T-cell infusion, mice were weighted and evaluated for xenogeneic GvHD according to the following score: weight loss (0 for weight loss <10%, 1 for 10%-25%, 2 for >25%), hunching (0-2), activity (0-2), fur texture (0-2), and skin integrity (0-2), maximum index 10. Weight loss was also estimated as an independent variable, since it was considered the most objective criterion (Table 1).

TABLE 1

Assessment of clinical xeno-GvHD in human T-cells infused mice.

| Criteria | Grade 0 | Grade 1 | Grade 2 |
|---|---|---|---|
| Weight loss | <10% | 10-25% | >25% |
| Posture | Normal | Hunching noted only at rest | Severe hunching impairs movement |

TABLE 1-continued

Assessment of clinical xeno-GvHD in human T-cells infused mice.

| Criteria | Grade 0 | Grade 1 | Grade 2 |
|---|---|---|---|
| Activity | Normal | Mild to moderately decreased | Stationary unless stimulated |
| Fur texture | Normal | Mild to moderately ruffling | Severe ruffling/poor grooming |
| Skin integrity | Normal | Scaling of paws/tail | Obvious areas of denuded skin. |

Allogeneic GvHD Model

In the allogeneic GvHD model, mice were transplanted with human skin and infused with allogeneic genetically modified lymphocytes to evaluate their ability to home to the human skin and mediate an allogenic GvH reaction. One week before transplantation, mice were transferred from laminar-flow isolators to normal cages and kept under specific pathogen-free conditions receiving sterile water and irradiated pellets ad libitum. Around three weeks before human T-cell infusion, mice are anesthetized with 12-18 mg avertin/mouse intraperitoneally. They were then depilated on the back, and an horizontal skin incision was performed bilaterally on the animal's back. A subcutaneous pocket was then opened, and a small piece of human abdominal epidermis (deprived from dermal fat and connective tissue) was introduced. At the end of the procedure, the wound was sutured. Since mice temperature progressively decreases during the operation, animals were placed in a heated box for about 30 min. and finally transferred into their cages.

Human T-Cell Infusion

To facilitate engraftment of human lymphocytes in NOD/scid mice, we functionally inactivated NK cells with anti-mouse IL-2 receptor β (TMβ-1) antibodies prior to lymphocytes transfer. The antibody was produced from the TMβ-1 hybridoma kindly provided by Prof Tanaka (Osaka University, Japan). At day 0, mice received total body irradiation with a single dose of 300 cGy (γ irradiation from a linear accelerator). Animals were then weighted and immediately infused with transduced human lymphocytes that had been harvested at day 9 after initial stimulation. Cells were infused intravenously in 250 μL saline solution.

Analysis of T Cell Engraftment

At week 1, 2 and 3 after T-cell infusion, about 300 μl blood/mouse was harvested from a little incision in the tail vein and collected in heparin-containing tubes. Red blood cells were lysed with a 3 min. exposure to ACK and then stained for cytofluorimetric analysis as described in the paragraph entitled "Staining for surface markers and cytofluorimetric analysis".

Analysis of Allogeneic GvHD

At week 3 after T-cell infusion, or earlier in case of severe GvHD, mice were sacrificed and the two pieces of human skin removed bilaterally. Formalin-fixed, paraffin-embedded skin was cut in 4-rpm thick sections and stained with hematoxylin and cosin for morphologic evaluation. Immunohistochemical assessment for the presence of human T lymphocytes was carried out with monoclonal anti-human CD3 antibody (Dako, Glostrup, Denmark) at 1:100 dilution, by way of the avidin/biotin peroxidase complex method using an automized Dako immunostainer. Staining reaction was revealed by the tetrahydrochloride chromogen method and sections were counterstained with hematoxylin. Pictures were taken with a Zeiss Axiocam HRC.

Statistical Analyses

For each variable considered in this study, mean, median and standard deviation were calculated. All statistical analyses were performed by using Microsoft Excel 2003 (Microsoft, Redmond, Wash.) and its add-in form Statcel2 (OMS publish, Saitama, Japan). Scheffe's F test following analysis of variance (ANOVA) was performed for parametric data, and Mann-Whitney's U test following Kruskal-Wallis test was performed for non-parametric data.

Results and Discussion

IL-7 Favors the Detection of Rare Tumor-Specific CD4$^+$ T Cells without the Need of Ag-Driven Cell Expansion.

The enumeration of Ag-specific T cells might be critical to several clinical conditions, for which the presence of Ag-specific T cells, is of diagnostic and prognostic interest. The authors recently developed a preclinical mouse model of tumor-disease with TS/A tumor cells expressing the *Leishmania Major*-derived model Ag LACK (TS/A-LACK). While LACK-specific naïve CD4 T cells can not be identified in unmanipulated BALB/c mice (29), the authors recently identified LACK-specific Ag-experienced CD44$^{high}$ CD4$^+$ T lymphocytes in TS/A-LACK tumor-bearing mice by fluorescent MHC class II/Ag multimers staining and by LACK-specific IL-2 and IFN-γ intracellular release (20).

In the effort of improving the detection and cloning of Ag-specific T cells, the authors investigated whether IL-7, known to favor survival of memory CD4$^+$ T cells (7, 9-14) might enrich the frequency of tumor-specific CD4$^+$ T cells. Control TS/A and TS/A-LACK tumor cells were subcutaneously injected in BALB/c mice. Twenty days after tumor cell injection, all the mice had developed measurable tumors. Mice were sacrificed and the tumor draining and non draining LN were surgically excised. While the formers contained a population of LACK-specific Ag-experienced CD44$^{high}$ CD4$^+$ T lymphocytes capable of IL-2 and IFN-γ production, the latter remained ignorant of the tumor and present LACK-specific naïve CD4$^+$ T lymphocytes (31). The frequency of LACK-specific CD4$^+$ T cells was analyzed ex vivo, and after 7 days in culture in the presence of recombinant IL-7 without any further Ag stimulation (FIG. 1). Ex vivo, the draining LN of TS/A-LACK-tumor bearing animals showed a low but significant frequency of CD4$^+$ I-A$^d$/LACK$^+$ cells expressing high levels of CD44 (FIG. 1A), and capable of producing IL-2 and/or IFN-γ upon LACK stimulation (FIG. 1B). After 7 days in culture with IL-7 alone, the frequencies of CD4$^+$ I-A$^d$/LACK$^+$ CD44$^{high}$ and LACK-specific cytokine-producing cells (FIG. 1A, B), as well as their total number (not shown, and FIG. 2, 4) was markedly increased. Among cytokine secreting cells, IL-2 and IFN-7 □producing cells, possibly representing intermediate memory T lymphocytes previously described as polyfunctional (30-33), were mostly enriched for. The frequency of LACK-specific T cells in the tumor-draining LN of control TS/A-tumor bearing mice and from the non draining LN of TS/A as wells as TS/A-LACK mice was comparable to the one found in naïve BALB/c mice ex vivo (FIG. 1C, D and not shown), and remained within background measures after the culture in IL-7 (FIG. 1C, D). Thus, IL-7 enriches LN cultures for in vivo-primed tumor-specific Ag-experienced CD4$^+$ T cells thus favoring their enumeration bypassing the need of in vitro Ag-driven cell expansion.

IL-7 and IL-2, but not Antigenic Stimulation Favor the Accumulation of Tumor-Specific CD4$^+$ T Cells.

Re-stimulation with Ag is most commonly used to expand, and in some instances to identify Ag-specific CD4$^+$ T cells (34). Furthermore, in addition to IL-7, also IL-2 and IL-15 control memory T cells proliferation (13, 35-37).

Hence, LN cells from TS/A-LACK tumor-bearing mice were cultured in the presence of irradiated singeneic APC unpulsed (APC) or pulsed with the LACK-derived peptide (Ag/APC) or in the presence of optimal amounts of IL-7, IL-2, IL-15 and IL-6, as control, and analyzed by flow cytometry. The frequency of CD4$^+$ I-A$^d$/LACK$^+$ CD44$^{high}$ T cells was slightly higher in cultured cells when compared to the one found ex vivo (FIG. 1A), but no difference was detected among control (APC) and Ag-stimulated cultures (Ag/APC) (FIG. 2A). In contrast, culturing the cells in IL-7 increased the frequency (FIG. 2A, B) as well as the total number (FIG. 2C, D) of LACK-specific CD4$^+$ T cells above the ones found in control (not shown) and IL-6-driven cultures. Similarly to IL-7, also IL-2 enriched LN cultures of CD4$^+$ I-A$^d$/LACK$^+$ CD44$^{high}$ T cells (FIG. 2A, C) and of CD4$^+$ cells capable of IL-2 and IFN-γ secretion upon Ag-specific stimulation (FIG. 2B, D). In IL-15-driven cultures, the frequency of CD4$^+$ I-A$^d$/LACK$^+$ CD44$^{high}$ T cells remained comparable to the one of control culture, but LACK-specific CD4$^+$ T cells capable of cytokine-secretion were enriched for in several independent experiments. Again, among the LACK-specific cytokine-producing cells, IL-2/IFN-γ-secreting CD4$^+$ T cells were mostly enriched for, and better favored in IL-7-driven culture (FIG. 2C,D).

IL-7 and IL-2 Sustain the Ag-Independent Spontaneous Proliferation and Survival of in Vivo-Primed Tumor-Specific CD4$^+$ T Cells.

The authors next investigated the mechanism by which IL-7 and IL-2 favor the accumulation of in vivo-primed LACK-specific CD4 T cells. First the authors analyzed the ability of these cytokines to support the expansion of these cells in vitro. LN cells were labeled with the CFSE vital dye, and cultured for a week in the absence or in the presence of the recombinant cytokines. In the absence of exogenous cytokines LN cells derived from naïve mice did not proliferate and retained their original CFSE content (FIG. 3A, left panel). In contrast, a detectable population of CD4$^+$ LN cells derived from TS/A-LACK-tumor-bearing mice proliferated and diluted its CFSE content in vitro in the absence of additional stimulation (FIG. 3A right panel). LACK-specific memory T cells, identified by their ability to secrete IL-2 and IFN-γ upon in vitro LACK restimulation were mainly contained among fast-proliferating CFSE$^{dim}$ cells (FIG. 3B, nil, MFI: 66), suggesting that they were committed to proliferate by a recent in vivo tumor-Ag encounter. In the presence of IL-7, a higher frequency of cells derived from tumor-draining LN completed 1-3 cell division, and LACK-specific T cells, identified by their ability to secrete IL-2 and IFN-g upon LACK-specific restimulation were markedly enriched for and had a lower CFSE content (MFI: 44) (FIGS. 3B and C). Indeed, LACK-specific CD4$^+$ T cells had performed more than 3-4 cell cycles, which distinguishes them from cells undergoing slow homeostatic-like cell division (less than 4 cell cycles). IL-7-driven homeostatic cell division was also found in the LN of naïve control mice (FIG. 5C). However, LACK-specific CD4$^+$ T cells were not enriched for in these cultures (not shown). Because of the spontaneous in vitro proliferation, and of the ability to produce both IL-2 and IFN-g upon restimulation, LACK-specific T cells found in tumor-draining LN and accumulating in vitro in response to IL-7 possibly represent recently primed unpolarized intermediate memory T cells, also found in vivo in chronically infected patients (32). In addition to IL-7, also IL-2 supported the in vitro proliferation of a fraction of CD4$^+$ T cells and increased the number of LACK-specific memory lymphocytes. In contrast, IL-15 and IL-6 failed to support either proliferation of the cells, or the accumulation of LACK-specific CD4$^+$ T cells over the one found in control (nil) cultures (FIGS. 3B, and D). Thus, IL-7 and IL-2 are capable of supporting the in vitro expansion of in vivo Ag-experienced memory T cells. In parallel experiments the authors showed that similar results were obtained by analyzing LN cultures derived from TS/A- and TS/A-LACK-tumor bearing 16.2β transgenic mice which contain a sizeable frequency of I-A$^d$/LACK$^+$ CD4$^+$ naïve T cells (25). Indeed as in the case of cultures derived from tumor-bearing BALB/c mice, the cultures derived from 16.2β mice contain LACK-specific CD4$^+$ expressing high levels of CD44 (FIG. 4A) and capable of IL-2 and IFN-γ LACK-specific release (FIG. 4B, 4C). IL-7, IL-2 and to a reduced extent IL-15, but not IL-6, TNF-α, and IL-10 enriched the cultures for these cells. LACK-specific CD4$^+$ T cells capable of IL-2 and IFN-γ LACK-specific release were contained again within CFSE dim cells (FIG. 4E).

Even in this unrelated model, IL-7 and IL-2 enrich LN cultures of Ag-experienced CD4$^+$ T cells by sustaining their in vitro proliferation bypassing the need of Ag-stimulation. To further characterize the relative potency of IL-7 and IL-2 in promoting the accumulation of Ag-experienced CD4$^+$ T cells, CFSE labeled cells were stained with the fluorescent dye TO-PRO-3, able to identify viable and dead cells within proliferating cells. IL-7 best preserved the viability of the cultures with only 15% of TO-PRO-3$^+$, dead cells after a week. At difference, up to 47% of the cells maintained in IL-2 and 60%, 57%, and 73% of the cells cultured in the absence of exogenous cytokine or in the presence of IL-15 and IL-6 resulted TO-PRO-3$^+$ (FIG. 5A). Moreover, while only 40% of CFSE dim cells excluded the dye in the presence of IL-2, up to 72% of these cells remained TO-PRO-3$^-$ in the presence of IL-7. This indicates that cells actively proliferating in the presence of IL-7 alone are more viable and possibly less susceptible to cell death when compared to the one cultured in IL-2 alone. The ability of IL-7 and IL-2 to favor T cell survival is linked to their capacity to regulate the expression of the anti-apoptotic factor Bcl-2 (10, 38). Thus, the authors analyzed Bcl-2 levels in CFSE-labeled LN cultures maintained in the absence and in the presence of recombinant cytokines. In every culture conditions, with the exception of IL-15, CFSE dim cells expressed optimal levels of Bcl-2 (FIG. 5B), suggesting that cells primed in vivo had received a pro-survival signal. IL-7 however, was unique in favoring the survival of both CFSE dim and CFSE bright cells. Indeed, up to 82.5% of CD4$^+$ T cells expressed optimal Bcl-2 levels in the presence of IL-7, whereas only 41.3%, 16.7%, 38%, and 10.5% of the cells respectively cultured in control medium, IL-2, IL-15 and IL-6 maintained high Bcl-2 expression (FIG. 5B, C). In the presence of IL-2 and IL-15 Bcl-2 expression in the majority of the cells was even reduced (FIG. 5C). Together these findings support the superior ability of IL-7 to favor CD4$^+$ T lymphocyte survival, when compared to IL-2 or IL-15 and suggest that IL-7 might be unique in preserving all the CD4$^+$ T lymphocyte subsets, regardless of their activation status. The authors further analyzed the surface phenotype in the tumor-draining LN derived cultures in order to assess whether IL-7 is more powerful than IL-2 in preserving all the subsets of in vivo-generated tumor-specific CD4 T+ cells and consequently if IL-7 is a major interesting tool to follow and detect rare in vivo Ag-experienced CD4+ T cells. TS/A-LACK tumor-draining LN cells were labeled with the CFSE vital dye and cultured for a week in the presence of IL-7 or IL-2 alone. Among CFSE dim cells maintained in IL-7 alone, a fraction of CD4$^+$ T cells, comparable to the one found ex vivo (FIG. 6A) retained high or low expression of CD44 and of CD62L (FIG. 6A, B). These cells are possibly representative of naïve, effector and central memory lymphocytes (8, 39-41). IL-7-treated CFSE dim cells expressed intermediate levels of CD25, and CD132, and downregulated the surface expression of CD127, as previously reported (42). At difference, most of CFSE dim cells maintained in IL-2 alone expressed a fully activated surface phenotype (CD44$^{high}$, CD25$^{high}$, CD62$^{low}$, Bcl-2$^{low}$, FIG. 6A), and cultures were enriched for CD44$^{high}$ T cells (FIGS. 6B and 7B). In cultures derived from 16.20 transgenic mice, while both IL-7 and IL-2 enriched for Ag-experienced CD4$^+$ T cells with a surface phenotype comparable to the one found ex vivo (FIG. 7A), only IL-7 maintained the original ratio between CD44 high and low cells among I-A$^d$/LACK$^+$ and I-A$^d$/LACK$^-$ CD4$^+$ T cells (FIG. 7B). The ability to preserve the relative lymphocyte representation might be relevant when attempting to exploit the short-term culture to determine the frequency of Ag-specific T cells in biological samples. Moreover, while most of Bcl-2$^+$ cells expressed low levels of the LN homing molecule CD62L in IL-2-cultured cells, in the presence of IL-7 up to 53% of CFSE dim CD4$^+$ T cells maintained an optimal expression of Bcl-2 and CD62L (FIG. 6C).

IL-7, IL-2 and IL-15 Expand Ag-Specific Specific Memory CD8$^+$ T Cells in an Ag-Independent Manner.

To further address the general usefulness of the Ag-independent short-term culture in IL-7 to reveal in vivo generated Ag-specific T cells the authors investigated whether Ag-specific CD8$^+$ T lymphocytes could be traced in a different context from tumor disease. The major aims were: 1) to evaluate the applicability of the invention for the tracing of in vivo Ag-experienced CD8$^+$ T cells, and not only in vivo Ag-experienced CD4$^+$ T cells, 2) to evaluate the applicability of the invention in a clinical setting (active vaccination), different from the diagnosis of anti-tumor immune responses.

In an attempt to investigate whether IL-7 could be used to reveal Ag-specific T cells in a clinical setting different from the one of tumor-disease, we analyzed peptide-specific CD8$^+$ T cells induced by a dendritic cell (DC)-based vaccine. C57BL/6 mice were vaccinated with bone marrow derived DC pulsed with the MHC class I restricted Tag IV peptide (DC-Tag) derived from the SV40 Large T antigen (18). Fourteen days later LN cells were analyzed by Ag-specific intracellular cytokine release ex vivo and after the cytokine-driven cultures. As a control LN cells were also derived from naïve unvaccinated C57BL/6 mice. Ex vivo, Tag IV specific CD8$^+$ T cells capable of producing only IFN-γ or IL-2 and IFN-γ after Ag re-stimulation were undetectable in naïve mice, and detectable at low frequencies in DC-vaccinated mice (0% and 0.37%, respectively). After 7 days in culture with IL-7, IL-2 and IL-15 in the absence of Ag re-stimulation the frequency (3.94%, 1.83% and 1.95%, respectively) as well as the total number (FIG. 8) of Tag IV-specific CD8$^+$ T cells were markedly increased in the cultures derived from DC-vaccinated mice and not from naïve mice (not shown).

In the same cultures the authors analyzed the relative enrichment of Tag IV-specific CD8$^+$ T cells in comparison to the total CD8$^+$ T cells (FIG. 9). Among all of the different conditions, the culture in IL-7, IL-2 and IL-15, but not IL-6 alone or plain medium increased the total counts of CD8$^+$ T cells by doubling their absolute number if compared to the ex vivo analysis (FIG. 9). By contrast despite the two-fold increase in total CD8$^+$ T cells, Tag IV specific CD8+ T cells had undergone a 5-7-fold-increase (FIG. 8) meaning that the in vivo Tag IV-vaccine experienced CD8 T cells have a major advantage among other CD8$^+$ T cell populations and are selectively enriched by the culture in the presence of pro-survival cytokines such as IL-7, IL-2 or IL-15. Thus IL-7 can be used to reveal tumor- and vaccine-induced CD8$^+$ T cell responses even in the absence of Ag re-stimulation.

IL-7 Reveals Antigen-Specific CD8$^+$ T Cells Otherwise Undetectable Ex Vivo.

TS/A cells naturally express the envelope protein gp70 of an endogenous MuLV for which an immunodominant epitope was previously described (AH-1, (19)). In their further attempt to address if the culture in IL-7 might also aid the identification of rare Ag-specific CD8$^+$ T cells, the authors compared the AH-1-specific CD8$^+$ T cell responses ex vivo and after a week in culture without or with IL-7, IL-2, IL-15 and IL-6 in the absence of Ag re-stimulation. Lymphocytes were analyzed by intracellular cytokine release upon stimulation with unpulsed and AH-1-pulsed syngeneic splenocytes (FIG. 10). In tumor-bearing mice AH-1-specific CD8$^+$ T cells were undetectable ex vivo since the frequency of cytokine producing cells remain within background levels (FIG. 10A) and was comparable to the one found in naïve mice (not shown). After 7 days, LN cultures derived from TS/A-LACK tumor-bearing LN and maintained with or without recombinant cytokines contained a variable frequency of cells producing IFN-γ independently from AH-1 re-stimulation (FIG. 10B). In the presence of IL-7 the cultures were enriched for AH-1-specific CD8+ T cells able to produce only IFN-γ or IL-2 and IFN-γ upon Ag re-stimulation (FIG. 10B). While also IL-2 increased the frequency and total number of AH-1-specific CD8$^+$ T cells (FIGS. 10B and C), these were not increased by IL-15- and IL-6 where the frequency remained comparable to the one found in cultures derived from naïve mice and within background levels (data not shown). Thus, IL-7, and IL-2 are able to reveal tumor-specific CD8$^+$ T cells otherwise undetectable ex vivo, bypassing the need for in vitro Ag-driven cell expansion.

Interleukin-7 Synergizes with a Cyclosporin A-Sensitive Signal for the Selective Expansion of Memory CD4$^+$ T Cells.

Proliferation and survival of memory CD4$^+$ T cells in vivo relies on both IL-7 as well as TCR-driven events (9). In vitro, TCR-driven proliferation of human memory T cells requires intact ERK activity, while cytokine-driven homeostatic cell division relies on p38 and is insensitive to Cyclosporin A (CsA) (13). The authors thus analyzed the requirements for the IL-7-driven accumulation of intermediate memory T cells by culturing lymphocytes in the presence of blocking antibodies or of inhibitors of selected signaling pathways. Cells were derived from the LN of naïve or TS/A-LACK-tumor bearing 16.2β mice, which are transgenic mice having a sizeable frequency of LACK-specific naïve CD4$^+$ T cells (25), labeled with CFSE and cultured in the presence of optimal IL-7 amounts, and the indicated inhibitory agents. As control, naïve T cells were stimulated with LACK-pulsed antigen presenting cells (APC) in the absence or in the presence of the selected inhibitors (FIG. 11A, B). Ag-driven T cell proliferation was markedly inhibited by anti-MHC class II mAb, and CsA, and partially hampered by anti-ICAM-1, anti-LFA-1 mAb (FIG. 11A, B). As expected Rapamycin (mTOR inhibitor) only delayed Ag-driven T cell division (FIG. 11A, B), while SB202190 (a p38 inhibitor) failed to inhibit Ag-stimulated T cell division, as previously reported (13). In the presence of IL-7 a fraction of CD4$^+$ T cells in cultures derived from control naïve mice performed 1-2 cycles of slow homeostatic cell division (FIG. 1 IC, nil, thin line), while a population of fast proliferating CD4+ CFSE$^{dim}$ cells accumulated in cultures derived from tumor-draining LN (FIG. 11C, nil, thick line). Again, -LACK-specific T cells capable of IFN-γ (FIG. 11E) and IL-2 (not shown) release were found mainly among the fast proliferation CD4 T cells. The addition of anti-MHC class II mAb to the IL-7-driven cultures of tumor-draining LN had a slight effect on the accumulation of fast proliferating CD4+ CFSE$^{dim}$ cells (FIG. 11D, thick line), and reduced the frequency of LACK-specific IFN-γ producing cells by 50% (FIG. 11E). Anti-ICAM-1, or anti-LFA-1 mAb, as well as CsA inhibited the IL-7-driven accumulation of fast-dividing CFSE$^{dim}$ CD4+ T cells, and of LACK-specific IFN-γ producing cells, leaving unchanged the IL-7-driven homeostatic cell division (FIG. 11D, thick lines and FIG. 11E). While SB202190, or PP2 only partially inhibited IL-7-driven accumulation of fast-proliferating LACK-specific CD4+ T (FIG. 11D, E), Rapamycin completely abolished the IL-7-driven slow and fast cell division (FIG. 11D, thick lines) and the IL-7-driven accumulation of LACK-specific T cells (FIG. 11E).

Together these findings indicate that IL-7 is able to drive the accumulation of fast proliferating IL-2/IFN-γ intermediate memory CD4+ T cells by the synergy with a cell-derived CsA sensitive signal possibly mediated by adhesion molecules and/or self peptide/MHC interaction.

IL-7 Sustains the Selective Accumulation of Fast-Dividing Peripheral Blood Human CD4 Memory T Lymphocytes.

It was previously reported that IL-7 and IL-15 sustain a slow homeostatic-like cell division of both central memory and effector human memory T cells (13). The authors investigated whether high-density culture conditions and optimal IL-7 amounts could instead reveal a population of fast-dividing intermediate memory T cells among peripheral blood-derived T lymphocytes. To this aim PBMC were derived from healthy donors, labeled with CFSE and cultured for 7 days at different cell densities in the absence or the presence of optimal IL-7 amounts (FIG. 12). At low cell density ($10^6$ cells per 24 well/ml), and in the absence of IL-7, all the cells failed to proliferate and retained the original CFSE content. At high cell density ($5\times10^6$ cells per 24 well/ml), a small, but measurable population of fast proliferating CFSE$^{dim}$ CD4+ T cells able to perform more than 4 cell division in the 7 days of culture appeared in control cultures maintained in Fetal Bovine Serum (FIG. 12, nil, top panels) or autologous serum (FIG. 13). In the presence of IL-7, a higher fraction of CD4 T cells proliferated, completing 1-6 cell division (FIG. 12, IL-7, bottom panels). Fast-proliferating cells able to perform more than 5 cell cycles were best revealed in high cell density cultures (FIG. 12B), and in optimal IL-7 amounts (FIG. 14). These fast-dividing cells mostly contained intermediate memory cells, as a large fraction of them produced IFN-γ (FIG. 15) and IL-2 (not shown) upon PMA and Ionomycin stimulation. IL-2/IFN-γ+ T cells best accumulated both in frequencies (FIG. 16), and in total number (not shown) at concentration above 50 ng/ml.

In addition to IL-7, also IL-2 and IL-15 sustained the in vitro proliferation of human CD4+ T cells (FIG. 17A), as also reported elsewhere (13), and the upregulation of Bcl-2 expression (FIG. 18). However, most of the cells proliferating in response to IL-2 and IL-15 completed 1-4 cycle of slow homeostatic-like cell division, and fast-proliferating memory T cells failed to accumulate. When CD8+ T cells were analyzed in the same cultures, IL-7 mostly supported the slow homeostatic division of a fraction of CD8+ T lymphocytes, while IL-2 and IL-15 allowed the accumulation of a population of fast-dividing CD8+ T lymphocytes (FIG. 17B) suggesting an analogous role for these cytokines on the two different T cell subsets.

IL-7 Driven T Cell Expansion of Peripheral Blood Human T Lymphocytes is Sensitive to Cyclosporin A.

The IL-7 and IL-15-driven slow homeostatic-like cell division of human memory T cells was reported to be insensitive to CsA, and instead rely on p38-dependent signaling (13). The authors next investigated the signaling required for the IL-7 driven expansion of the intermediate memory fast-proliferating human T cells. As in the case of mouse cells, the IL-7-driven accumulation of fast-proliferating CD4+ T cells was sensitive to CsA, and to RAPA, and to a lesser extent to SB (FIG. 19A) and PP2 (not shown). CsA did not prevent the cytokine-driven slow proliferation consistently with previous report (13). The expansion of fast-proliferating memory cells also relied on LFA-1-dependent interactions, as the addition of an anti-LFA-1 mAb inhibited their accumulation (FIG. 19B). Fast-proliferating CD4 T cells expanding in high cell density conditions, and in IL-7-driven cultures were represented by CD45RA−, CD62L− T lymphocytes (effector memory) and by CD45RA−, CD62L+ (central memory) CD4 T lymphocytes. Of note, CD45RA−, CD62L+ memory T cells appeared to be the largest fraction of spontaneously proliferating CD4 T cells, were mostly enriched for by the ex vivo expansion protocol, and were most sensitive to CsA inhibition (FIGS. 19B and C). Thus, the authors identified a population of CD45RA−, CD62L+ memory CD4+ T cells able of spontaneous in vitro fast proliferation in the peripheral blood of healthy donors. The accumulation of these memory CD4+ T cells was favored by IL-7, was cell density-dependent and CsA-sensitive.

IL-7-Driven Short-Term Cultures Aid the Enumeration of *Mycobacterium tuberculosis*-Specific CD4+ T Cells in Human Subjects.

Having determined that IL-7 sustains the in vitro expansion of a fast-proliferating memory T cells possibly programmed in vivo to proliferate in vitro, the authors investigated whether this could be exploited for the clinical investigation of immune-related pathologies. To this aim, crio-preserved PBMC samples of *M. tuberculosis*-infected (TB) patients were analyzed at the time of thaw or after a week in culture with optimal IL-7 amounts, by MTP-specific ELISPOT analysis (43). Patients were chosen based on their clinical history and manifestation of acute TB (clinic and culture confirmed), on their positive reaction to the TST, and on the ability to respond to MTP in the ELISPOT-IFN-γ assay. Crio-preserved PBMC from not infected healthy donors were also analyzed as control. Pt#1 showed a sizeable number of IFN-γ+ spots upon MTP-specific re-stimulation (FIG. 20A), at the time of thawing (Crio-preserved: 950 SFC×$10^6$ PBMC). Upon culturing the cells in control medium (Nil) the number of IFN-γ+ MTP-specific cells doubled (1890 SFC×$10^6$ PBMC), reflecting the increased frequency of CD4+ T cells in cultured cells (numbers in brackets in FIG. 20A). In the presence of IL-7 the number of IFN-γ+ MTP-specific cells (3930 SFC×$10^6$ PBMC) was 4 fold higher than the one found in crio-preserved/thawed samples, and doubled when compared to control cultures. Pt#2 and Pt#3 had detectable MTP-specific T cells at the time of sample collection (not shown), but not in crio-preserved/thawed samples (FIG. 20B, 20C). Upon the IL-7-driven culture, IFN-γ+ MTP-specific spots were instead revealed. IL-7 resulted in the increase in absolute numbers of MTP-specific T cells in all the TB-patients analyzed, and as a result, the difference among healthy donors and TB patients in the number of MTP-specific IFN-γ producing cells gained in significance (FIG. 21). MTP-specific T cells accumulating in response to IL-2 were mostly represented by IL-2/IFN-γ$^+$ memory CD4 T cells as determined by MTP-induced intracellular cytokine secretion (FIG. 22). Furthermore, the expansion of MTP-specific IL-2/IFN-γ$^+$ memory CD4 T cells was prevented in the presence of CsA (FIG. 23).

IL-7-Driven Short-Term Cultures Aid the Enumeration of *Candida* Antigen-Specific Human T Lymphocytes.

In addition to MTP-specific T cells, the authors also investigated whether IL-7 could enhance the identification of T lymphocytes specific for *Candida Albicans*-derived antigens. To this aim, PBMCs from Pt#1 were analyzed at the time of thawing or after a 7 days culture in plain medium or in the presence of IL-7, by an ELISPOT assay performed with unpulsed or *C. Albicans*-derived Ag-pulsed irradiated autologous PBMC. As in the case of *M. Tuberculosis*-specific T cell responses, also *C. Albicans*-specific T cells capable of IFN-γ release were enriched for by the short-term culture in IL-7 (FIG. 24A, B).

The Adoptive Cell Therapy with IL-7/IL-15 Cultured Memory T Cells Delays Tumor Growth In Vivo.

Having determined that IL-7 determines the accumulation of in vivo primed memory CD4 T cells, and that IL-15 best drives the expansion of CD8 memory T cells, the authors evaluated whether the expanded populations have a clinical relevance. To address this point lymph nodes were derived from TS/A-LACK tumor-bearing mice and cultured for 7 days in optimal cell density (5×10$^6$ cells/ml) and optimal cytokines amounts (50 ng/ml). As a control naïve T cells derived from a control mouse were also cultured in the same conditions. Thereafter 10$^7$ cultured cells bearing comparable frequencies of CD4 and CD8 T cells were adoptively transferred into naïve BALB/c mice. 48 hours later mice were challenged with 300.000 TS/A-LACK cells and tumor growth was monitored overtime. As shown in FIG. 25, TS/A-LACK tumors rapidly developed in control mice and in mice adoptively transferred with cytokine-treated naïve T cells. In contrast, tumor growth was significantly delayed in mice adoptively transferred with cytokine-treated tumor-bearing mice derived T cells (FIG. 25). This indicates that the IL-7/IL-15-driven cultures determined the expansion of a population of clinically relevant memory T cells.

Generation of Gene-Modified Central Memory Human T-Cells

Cell proliferation is required for retroviral transduction of T lymphocytes. The authors activated PBMC with aCD3 or baCD3/CD28. Cells were activated with baCD3/CD28 and cultured with IL-7 and IL-15 or with aCD3 and cultured with IL-2 (FIG. 27A). Cells were transduced at day 2, by spinoculation, with the SFCMM3 retroviral vector. Transduction was performed at the same time and following the same protocol. Activation with baCD3/CD28 in the presence of IL-7 and IL-15 promoted a higher T cell expansion (FIG. 27A) and led to a higher transduction efficiency than activation with aCD3 in the presence of IL-2 (FIG. 27B). In addition, at the end of the culture period, the physiological CD4/CD8 ratio was analyzed and found to be better maintained in transduced cells activated with baCD3/CD28 and cultured with IL-7 and IL-15 than with cells activated with aCD3 and cultured with IL-2 (FIG. 27C).

Polyclonal Activation Required for Retroviral Transduction of T Lymphocytes Enriches for Memory Cells.

To determine the relative distribution of memory subsets in human T-cells transduced with the retroviral vector, the authors analyzed CD45RA/CD62L co-expression. At day 14, transduced T-cells activated with aCD3 and cultured with IL-2 were mainly CD45RA$^-$ CD62L$^-$, i.e, effector memory cells. On the contrary, transduced CD4$^+$ T-cells activated with baCD3/CD28 and cultured IL-7 and IL-15 were highly enriched for CD45RA$^-$CD62L$^+$, i.e., central memory cells (FIG. 28 A). An enrichment of CD45RA$^-$CD62L$^+$ central memory cells in the case of cells activated by baCD3/CD28 and cultured with IL-7 and IL-15 was also observed for transduced CD8$^+$ cells (FIG. 28B). To better define the memory phenotype, we also analyzed CD28/CD27 co-expression. Whereas for transduced CD4$^+$ cells there was no difference in the relative distribution of the subsets between the two conditions (FIG. 28C), for transduced CD8$^+$ cells, activation with baCD3/CD28 and culture with IL-7 and IL-15 advantaged CD28$^+$CD27$^+$ T-cells (FIG. 28D).

Functional Correlates of Gene-Modified Central Memory Human T-Cells

Central and effector memory human T lymphocytes, as identified by surface phenotype, differ in the ability to produce effector cytokines. At day 14, the authors re-stimulated the two populations of gene-modified T-cells and analyzed them for cytokine production. CD4$^+$ T-cells stimulated with aCD3 and cultured with IL-2 efficiently produced the prototypical effector cytokine IFN-γ In sharp contrast, the majority of CD4$^+$ T-cells stimulated with baCD3/CD28, IL-7 and IL-15 were un-polarized cells and neither produced IFN-γ nor IL-4 (FIG. 29A). A similar result was obtained with CD8$^+$ T-cells (FIG. 29B).

GvHD Potential of Gene-Modified Central Memory Human T-Cells.

Different xenograft models have been proposed to study GvHD induced by human lymphocytes. In order to evaluate the relative anti-host reactivity of the two suicide gene-modified central and effector memory human T lymphocytes in vivo, these populations were infused into NOD/scid mice conditioned with non-lethal irradiation and anti-NK antibodies. Control mice were infused with human purified syngeneic PBL. The authors observed that central memory gene-modified lymphocytes were more efficient at engrafting than their effector memory counterpart (human chimerism at week 1: average 0.45% range 0.2-1.1 for effector memory genetically modified cells vs average 4.5% range 4.1-5.2 for central memory genetically modified cells, Table 2. 5 out of 6 mice infused with effector memory gene-modified T-cells presented a decreased human chimerism after week 1 and did not show GvHD. On the other hand, persistent human chimerism was observed in the majority of mice infused with central memory suicide gene-modified T-cells and 4 mice out of 6 developed severe GvHD.

TABLE 2

Engraftment and gaft-versus-host disease

|  | PBL | Effector memory TK$^+$ cells | Central memory TK$^+$ cells |
|---|---|---|---|
| Human chimerism in % (range)$^a$ | 3.6 (2.5-5) | 0.45 (0.2-1.1) | 4.5 (4.1-5.2) |
| GvHD incidence$^b$ | 6/6 | 1/6 | 4/6 |

$^a$Average (range) at week 1 after infusion
$^b$Defined as weight loss >10% from initial body weight Generation of Gene-Modified Central Memory Human T Cells To determine the minimal requirements to obtain a number of gene-modified central memory human T-cells suitable for clinical application, we compared the following five T-cell transduction conditions:
1. soluble anti-CD3 antibodies (OKT-3)+high doses of interleukin 2 (600 UI/ml);
2. anti CD3/CD28 cell sized beads without any cytokine;
3. anti CD3/CD28 cell sized beads+low doses of IL-2 (200 IU/ml);
4. anti CD3/CD28 cell sized beads+low doses of IL-7 (5 ng/ml);
5. anti CD3/CD28 cell sized beads+low doses of IL-7 (5 ng/ml)+low doses of IL-15 (5 ng/ml).

Cells were transduced and cultured following protocols described in materials and methods. These experiments produced the following results:

1. Activation with Anti CD3/CD28 Beads Allows Higher Transduction Efficiency than Activation with Soluble Anti-CD3 Antibodies As shown in FIG. 30A retroviral transduction efficiency was significantly higher after stimulation with cell sized magnetic beads than after stimulation with the soluble anti-CD3 antibody. This result was independent from the use of cytokines in the culture cocktail.

2. Activation with CD3/CD28 Beads Followed by Culture in the Presence of Cytokine (IL2, IL7+IL15 or IL7) Preserves the Physiological CD4/CD8 Ratio in Transduced T Lymphocytes.

To evaluate the ability of our transduction protocols in preserving the physiologic CD4/CD8 ratio, we analysed the CD4/CD8 ratio of transduced cells produced by different protocols, 10 days after initial stimulation. As shown in FIG. 30B, only stimulation with magnetic beads followed by culture in cytokines (IL2, IL7 or IL7+IL15) maintained a physiological CD4/CD8 ratio in transduced T-cells, while the average CD4/CD8 ratios observed with other culture conditions did not exceed 1/1.

3. Activation with CD3/CD28 Beads Followed by Culture in the Presence of Cytokine (IL2. IL7+IL15 or IL7) Induces a Significantly Higher Proliferation Rate of Transduced Cells than Other Culture Conditions.

Protocol of ex vivo gene transfer designed for clinical application must fulfil to the relevant criteria related to feasibility: one of the major feasibility issue in the clinical translation of a gene therapy approach relates to cell number and cell expansion in vitro. As shown in FIG. 30C, a statistically significant difference was observed in cell numbers obtained between genetically modified cells stimulated with beads and cultured with cytokines, compared to the other conditions (beads alone and OKT3+IL-2). These results show that transduced lymphocytes obtained with anti-CD3/CD28-conjugated beads and culture with IL-7, IL-7+IL-15 or IL-2 rapidly expand in vitro to numbers suitable for clinical application.

4. Activation with Anti CD3/CD28 Beads Generates Mainly Central Memory CD8$^+$ and CD4$^+$ Transduced Lymphocytes We investigated the immunophenotype of transduced cells obtained by different culture conditions through FACS staining for CD3, CD4, CD8, CD45RA, and CD62L 10 days after initial stimulation. We observed that a very high fraction (about 80%) of both CD8$^+$ and CD4$^+$ T-cells, which had been stimulated with anti CD3/CD28 beads, was CD45RA$^-$ CD62L$^+$: this pattern corresponds to central memory T-lymphocytes. On the contrary, OKT3-stimulated T-cells showed 60% CD8$^+$ and 45% CD4$^+$ effector memory T-cells (CD45RA$^-$ CD62L-) versus 30% CD8$^+$ and 50% CD4$^+$ central memory TK$^+$ lymphocytes. (FIG. 31).

γ-Chain Receptor Expression During Culture of Transduced Lymphocytes

Cytokine receptors' expressions are tightly regulated during T-cell stimulation. We analysed the expression kinetic of γ-chain cytokine receptors during the different T cell culture and transduction protocols, as a measure of T cell functions and potential. To this purpose, we performed cytofluorimetric analysis after staining transduced cells with fluorochrome-labeled antibodies to CD122 (IL-2/15 receptor common β chain), CD25 (IL-2 receptor α chain) and CD127 (IL-7 receptor α chain) at different time-points after first stimulation.

1. IL-2/15 Receptor β Chain (CD122) Expression does not Change Among the Different Transduction Protocols During the course of immune responses IL-2/IL-15 receptor β expression increases after T cell activation and then decreases to an intermediate level of expression that is retained throughout the memory-cell phase (13).

FIG. 32 shows the expression kinetic of CD122 in transduced lymphocytes during 13 days of culture. We did not observe any differences in terms of CD122 expression on T cells cultured among the five protocols. In all cases, T-cells, and in particular CD4$^+$ cells, up-regulated CD122 after activation, reaching a peak around day 4, when almost 100% of genetically modified cells expressed the molecule. Cells then slowly down-regulated CD122 expression, reaching the same level of expression observed before stimulation 13 days after the beginning of T-cell culture, when cells had reached the resting state.

2. Stimulation with Beads CD3/CD28 Promotes an Intense and Prolonged Expression of IL-2 Receptor α in Transduced T-Cells IL-2 receptor α (CD25) is a relevant activation marker for T-lymphocytes. In physiological conditions, naïve T cells do not express CD25; however, its expression is rapidly upregulated by T-cell activation and usually declines before the proliferative peak of the response. In transduced cells activated by beads, independently from subsequent culture conditions, flow cytometry analysis showed that at day 2 after stimulation the majority of T-cells underwent a significant increase in IL-2 receptor α expression. On the contrary, only 40% of transduced cells activated with soluble OKT3 up-regulated the receptor (FIG. 33), suggesting that the majority of T cells were not properly activated with this stimulation procedure. As long as CD25 is expressed, T cells can proliferate to IL-2, thus actively participating to the immune response. In transduced cells produced after beads activation, the expression of CD25 remained high in the majority of cells up to day 13. On the contrary, cells that up-regulated CD25 after stimulation with soluble anti-CD3 antibody reached a peak of expression 2 days later than cells activated with beads and then rapidly down-regulated the CD25 molecule.

3. Transduced Cells Activated with Anti-CD3/CD28 Beads+IL-7 Show the Maximal Expression of IL-7 Receptor α, a Marker of Long-Surviving Memory T-Cells In physiological conditions, IL-7 receptor α (CD127) is constitutively expressed by naïve T cells. Its expression is downregulated by T-cell activation (in a specular manner compared to CD25) and such down-regulation might promote cell death. Conversely, expression of CD127 increases as the immune response proceeds, reaching high levels in memory T cells. IL-7 is a potent survival factor for memory T-lymphocytes: triggering of the receptor by IL7 promotes T cell survival and proliferation and protects cells from apoptosis through different intracellular signal pathways. We analysed the kinetic of CD127 expression in our transduced cells. IL-7 receptor α underwent a deep down-regulation after stimulation (approximately between day 1 and day 6).

From day 7, its expression progressively increased and interestingly, we observed a significant difference in the proportion of CD127+ transduced cells obtained with beads CD3/CD28 and IL-7 compared to all other conditions (FIG. 34). From day 9, more than 80% of both $CD8^+$ and $CD4^+$ $TK^+$ cells, which had been stimulated with cell-sized beads and IL-7, were positive for IL-7 receptor α. This suggests that IL-7 is responsible for the maintenance of high levels of CD127 expression in the majority of T cells after activation, thus providing an exclusive long-term survival advantage to transduced cells.

Transduced Lymphocytes Generated with Beads+IL-7 have the Highest Alloreactive Potential From the results previously shown, it emerges that activation with anti-CD3/CD28 magnetic beads and the adjuvant effect of cytokines (in particular IL-7) are important factors for the generation of central memory transduced T-lymphocytes, with a high survival potential. Our next aim was to investigate whether these CM transduced T-lymphocytes were actually able to elicit a powerful and effective immune response. We addressed this issue in vitro by stimulating transduced cells with allogeneic antigens and we obtained the following results:

1. Transduced Lymphocytes Generated with Beads+IL-7 have the Highest Proliferative Potential, when Stimulated with an Allogenic Antigen.

Transduced T cells generated with each of the five conditions were stained with CFSE and co-cultured with irradiated allogeneic PBMCs. After 1 week we counted cell numbers and analyzed CFSE dilution by FACS to evaluate the percentage of dividing cells. As shown in FIG. 35A, we found a statistically significant difference between IL-7-containing conditions and the other protocols. in $CD3^+$ and $CD8^+$ T-cells: Indeed, a high percentage (40%) of transduced cells generated with beads CD3/CD28+IL-7 had divided in 1 week after allogeneic stimulation. On the contrary, only 20% of transduced cells generated with OKT3-had divided in the same culture conditions.

2. Transduced Lymphocytes Generated with Beads+IL-7 have the Lowest Sensitivity to Death.

In order to maintain T-lymphocytes homeostasis, massive T-cell activation in response to an allogeneic challenge is usually followed by an extensive apoptotic program, IL-2 being the main player in the so called "activation induced cell death" (AICD). Mechanisms to counteract AICD are required for the development of an efficient and long-lasting immunological memory after primary immune responses. To investigate the sensitivity of transduced cells to AICD, we stained allo-stimulated $CFSE^+$ lymphocytes with To-Pro 3, a fluorescent dye, which selectively binds to dead cells. We calculated the number of dead cells in dividing and non dividing transduced cell populations, in order to evaluate respectively activation induced cell death and death by neglect (FIG. 35B). Transduced cells cultured in IL2 (independently from the activation signal) proved highly sensitive to AICD and death by neglect. On the contrary, transduced cells generated with beads CD3/CD28+IL-7 displayed the lowest mortality, comparable to that of unmodified lymphocytes. This observation may be related to the persistent expression of CD127 on a high proportion (33% of $CD8^+$ and 52% of $CD4^+$) of genetically modified lymphocytes generated with beads CD3/CD28 and IL-7.

In accordance with this observation, transduced lymphocytes generated with beads CD3/CD28 and IL-2, who proved highly sensitive to cell death, showed the lowest proportion of cells expressing $CD127^+$ cells (30%). FACS plots in FIG. 36A show a representative example of CD127 detection in CFSE-stained transduced T-lymphocytes 10 days after allogeneic stimulation.

3. Transduced Lymphocytes Generated with Beads+IL-7 Preserve a Central Memory Phenotype after Allogeneic Stimulation.

Immunological memory is ensured by a self-renewal capacity of memory cells, that, upon antigen re-encounter, divide, and generate both effectors, able to directly eliminate the pathogen, and memory cells, able to protect the host long-term. To verify whether central memory genetically modified lymphocytes had this self-renewal capacity, we analysed the expression of CCR7 (a marker of central memory cells) on CFSE-stained cells, at day 10 after allogeneic stimulation. As shown in FIG. 36A, our data show that 59% of $CD3^+$ genetically modified lymphocytes generated with beads CD3/CD28 and IL-7, that had undergone at least one division, were positive for CCR7 expression. On the contrary, only 17% of $CD3^+$ genetically modified lymphocytes generated with OKT3 expressed CCR7. Culture in the presence od IL-7 was essential for preserving the self-renewal capacity of central memory lymphocytes, since only 36% of $CD3^+$ genetically modified lymphocytes generated with beads CD3/CD28 and IL-2 maintain the expression of CCR7 after allogeneic stimulation. According to this result, when cells were re-challenged in vitro with the same allogeneic stimulators, following the same culture conditions utilized in the first stimulation, more than 70% of transduced cells generated with CD3/CD28 beads and IL-7 and only 50% of transduced cells generated with OKT3 proliferated in the following week (FIG. 36B).

Transduced Lymphocytes Generated with Beads+IL-7 have the Highest Alloreactive Potential In Vivo To evaluate the efficacy of central memory transduced T-cells in vivo, we established a new chimeric model, based on NOD/Scid mice transplanted with human skin. Based on results obtained in vitro we decided to investigate the potency of genetically modified central memory lymphocytes generated with beads CD3/CD28+IL-7, beads CD3/CD28+IL-2 and to compare the functional activity of these cells with genetically modified effector memory lymphocytes, generated with OKT-3 and IL-2, and currently utilized in clinical trials. After infusion of transduced cells, xenogeneic T-cell reactivity was determined by clinical observation, while allogeneic GvHD was evaluated histologically and correlated to the analysis of human skin infiltration by transduced cells. Results of these studies are summarized here below:

Genetically Modified Cells Generated with CD3/CD28 and IL-7 Rapidly Engraft in Skin-Transplanted NOD/Scid Mice The number of human T-lymphocytes in mice peripheral blood increased from week one to week 2 after infusion. Transduced cells generated with beads engrafted at higher extent than transduced cells generated with OKT-3. The difference was more evident at the second week after T cell infusion (FIG. 37).

Activation with Beads CD3/CD28 and IL-7 Stimulation Confer to Transduced Cells the Highest Reactivity Against Xenogeneic Antigens. Xenogeneic GvHD was Monitored According to a Clinical Score Described in Material and Methods and by Measuring Weight Loss.

Infused NOD/Scid mice progressively lost their weight and some of them eventually died for xenogeneic GvHD or were sacrificed for ethical reasons. The most xeno-reactive T-cells were those stimulated with anti CD3/CD28 beads and cultured with IL-7, followed by transduced cells generated with CD3/CD28 beads and IL-2. The stimulation with soluble anti CD3 antibodies did not generate strongly xeno-reactive T-cells, as mice infused with these lymphocytes did show neither a significant body weight loss, nor the appearance of other clinical xeno-GvHD signs (FIG. 38).

Activation with Beads CD3/CD28 and IL-7 Stimulation Confer to Transduced Cells the Highest Reactivity Against Allogeneic Antigens Our NOD/Scid human skin chimera mouse model consists of NOD/Scid mice, that had undergone skin transplantation, through the insertion of two pieces of human abdominal epidermis into two subcutaneous pockets on the mouse back and that were subsequently infused intravenously with genetically modified cells. Human skin transplantation allows to investigate T-cell reactivity against allogeneic antigens, by histological studies. Transplanted human skin, indeed, contains not only epidermal and stromal cells, but also some antigen presenting cells, which are able to attract circulating lymphocytes and possibly promote their activation. Three weeks after human T-cell infusion, we sacrificed NOD/Scid chimera mice and removed human skin bilaterally. All biopsies were subsequently blindly analysed by pathologists through both ematossilin-eosin (EE) and anti human CD3 staining. We observed a massive human T-cell infiltration in the context of human skin, only in mice that had been infused with "beads+IL-7" stimulated T-lymphocytes. In "OKT-3" conditions the level of T-cell tissue infiltration, if any, was clearly spare. FIG. 39 shows representative examples of these results.

CONCLUSION

Although it is generally recognized that T cells play a central role in the generation of immunity to pathogens, to tumors, and to immuno-deficiencies and in autoimmune disorders, it has been difficult to use them as diagnostic and prognostic markers of immunocompetence in humans. Furthermore, techniques suitable for the expansion of non polarized poly-functional intermediate and central memory lymphocytes are currently missing.

The results described in this report of invention identify new culture conditions which:
A) allow the Ag-independent accumulation of in vive primed memory T cells;
B) guide expansion of central memory lymphocytes in spite of lymphocyte polyclonal stimulation and genetic manipulation.

Results indicate that IL-7, and IL-15 can be used to enrich biological samples, such as peripheral LN, blood, and tumor for in vivo primed Ag (tumor/pathogens/allergens/self antigens)-specific $CD4^+$ or $CD8^+$ T cells. When compared to IL-2, IL-7 better maintained the original lymphocyte phenotype and representation and better favored the survival of all T lymphocyte subsets, allowing the detection and expansion of rare $CD4^+$ T memory lymphocytes.

The ability to enumerate Ag-specific $CD4^+$ or $CD8^+$ T cells in the context of chronic viral infection, autoimmune disease, vaccination or immunotherapy would provide a direct measure for the patient immunocompetence or disease and assist clinicians in the choice of the most appropriate therapy. Furthermore, the possibility to enrich in vivo-primed memory T cells without altering their phenotype might improve their characterization, as well as their exploitation for the immune response in adoptive immunotherapy strategies. Finally, genetically modified central memory T-cells can be obtained upon CD3/CD28 activation and culture with homeostatic cytokines. When infused in conditioned immunodeficient hosts genetically modified central memory T-cells i) engraft and expand at significantly higher levels than effector memory genetically modified T cells and ii) are more potent than effector memory genetically modified lymphocytes at inducing an immune response to host and allogeneic antigens.

These results demonstrate that fully functional central memory gene-modified lymphocytes can be obtained and exploited for the cure of human diseases.

REFERENCES

1. Jenkins, M. K., A. Khoruts, E. Ingulli, D. L. Mueller, S. J. McSorley, R. L. Reinhardt, A. Itano, and K. A. Pape. 2001. In vivo activation of antigen-specific CD4 T cells. *Annu Rev Immunol* 19:23-45.
2. Sprent, J., and C. D. Surh. 2002. T cell memory. *Annu Rev Immunol* 20:551-579.
3. Marrack, P., J. Bender, D. Hildeman, M. Jordan, T. Mitchell, M. Murakami, A. Sakamoto, B. C. Schaefer, B. Swanson, and J. Kappler. 2000. Homeostasis of alpha beta TCR+ T cells. *Nat Immunol* 1:107-111.
4. Novak, E. J., A. W. Liu, G. T. Nepom, and W. W. Kwok. 1999. MHC class II tetramers identify peptide-specific human CD4(+) T cells proliferating in response to influenza A antigen. *J Clin Invest* 104:R63-67.
5. Mallone, R., and G. T. Nepom. 2004. MHC Class II tetramers and the pursuit of antigen-specific T cells: define, deviate, delete. *Clin Immunol* 110:232-242.
6. Boursalian, T. E., and K. Bottomly. 1999. Survival of naive CD4 T cells: roles of restricting versus selecting MHC class II and cytokine milieu. *J Immunol* 162:3795-3801.
7. Seddon, B., and R. Zamoyska. 2002. TCR and IL-7 receptor signals can operate independently or synergize to promote lymphopenia-induced expansion of naive T cells. *J Immunol* 169:3752-3759.
8. Sallusto, F., D. Lenig, R. Forster, M. Lipp, and A. Lanzavecchia. 1999. Two subsets of memory T lymphocytes with distinct homing potentials and effector functions. *Nature* 401:708-712.
9. Seddon, B., P. Tomlinson, and R. Zamoyska. 2003. Interleukin 7 and T cell receptor signals regulate homeostasis of CD4 memory cells. *Nat Immunol* 4:680-686.
10. Kondrack, R. M., J. Harbertson, J. T. Tan, M. E. McBreen, C. D. Surh, and L. M. Bradley. 2003. Interleukin 7 regulates the survival and generation of memory CD4 cells. *J Exp Med* 198:1797-1806.
11. Li, J., G. Huston, and S. L. Swain. 2003. IL-7 promotes the transition of CD4 effectors to persistent memory cells. *J Exp Med* 198:1807-1815.
12. Lenz, D. C., S. K. Kurz, E. Lemmens, S. P. Schoenberger, J. Sprent, M. B. Oldstone, and D. Homann. 2004. IL-7 regulates basal homeostatic proliferation of antiviral $CD4^+$ T cell memory. *Proc Natl Acad Sci USA* 101:9357-9362.
13. Geginat, J., F. Sallusto, and A. Lanzavecchia. 2001. Cytokine-driven proliferation and differentiation of human naive, central memory, and effector memory CD4 (+) T cells. *J Exp Med* 194:1711-1719.
14. Rivino, L., M. Messi, D. Jarrossay, A. Lanzavecchia, F. Sallusto, and J. Geginat. 2004. Chemokine receptor expression identifies Pre-T helper (Th)1, Pre-Th2, and nonpolarized cells among human CD4+ central memory T cells. *J Exp Med* 200:725-735.
15. Jaleco, S., L. Swainson, V. Dardalhon, M. Burjanadze, S. Kinet, and N. Taylor. 2003. Homeostasis of naive and memory CD4+ T cells: IL-2 and IL-7 differentially regulate the balance between proliferation and Fas-mediated apoptosis. *J Immunol* 171:61-68.
16. Jameson, S. C. 2002. Maintaining the norm: T-cell homeostasis. *Nat Rev Immunol* 2:547-556.
17. Benigni, F., V. S. Zimmermann, S. Hugues, S. Caserta, V. Basso, L. Rivino, E. Ingulli, L. Malherbe, N. Glaichenhaus, and A. Mondino. 2005. Phenotype and homing of CD4 tumor-specific T cells is modulated by tumor bulk. *J Immunol* 175:739-748.
18. Degl'Innocenti, E., M. Grioni, A. Boni, A. Camporeale, M. T. Bertilaccio, M. Freschi, A. Monno, C. Arcelloni, N. M. Greenberg, and M. Bellone. 2005. Peripheral T cell tolerance occurs early during spontaneous prostate cancer development and can be rescued by dendritic cell immunization. *Eur J Immunol* 35:66-75.
19. Rosato, A., S. D. Santa, A. Zoso, S. Giacomelli, G. Milan, B. Macino, V. Tosello, P. Dellabona, P. L. Lollini, C. De Giovanni, and P. Zanovello. 2003. The cytotoxic T-lymphocyte response against a poorly immunogenic mammary adenocarcinoma is focused on a single immunodominant class I epitope derived from the gp70 Env product of an endogenous retrovirus. *Cancer Res* 63:2158-2163.
20. Appelbaum, F. R. 2001. Haematopoietic cell transplantation as immunotherapy. *Nature* 411:385-389.
21. Bonini, C., G. Ferrari, S. Verzeletti, P. Servida, E. Zappone, L. Ruggieri, M. Ponzoni, S. Rossini, F. Mavilio, C. Traversari, and C. Bordignon. 1997. HSV-TK gene transfer into donor lymphocytes for control of allogeneic graft-versus-leukemia. *Science* 276:1719-1724.
22. Fehse, B., F. A. Ayuk, N. Kroger, L. Fang, K. Kuhlcke, M. Heinzelmann, T. Zabelina, A. A. Fauser, and A. R. Zander. 2004. Evidence for increased risk of secondary graft failure after in vivo depletion of suicide gene-modified T lymphocytes transplanted in conjunction with CD34+-enriched blood stem cells. *Blood* 104:3408-3409.
23. Tiberghien, P., C. Ferrand, B. Lioure, N. Milpied, R. Angonin, E. Deconinck, J. M. Certoux, E. Robinet, P. Saas, B. Petracca, C. Juttner, C. W. Reynolds, D. L. Longo, P. Herve, and J. Y. Cahn. 2001. Administration of herpes simplex-thymidine kinase-expressing donor T cells with a T-cell-depleted allogeneic marrow graft. *Blood* 97:63-72.
24. Mougneau, E., F. Altare, A. E. Wakil, S. Zheng, T. Coppola, Z. E. Wang, R. Waldmann, R. M. Locksley, and N. Glaichenhaus. 1995. Expression cloning of a protective *Leishmania* antigen. *Science* 268:563-566.
25. Malherbe, L., C. Filippi, V. Julia, G. Foucras, M. Moro, H. Appel, K. Wucherpfennig, J. C. Guery, and N. Glaichenhaus. 2000. Selective activation and expansion of high-affinity CD4$^+$ T cells in resistant mice upon infection with *Leishmania major*. *Immunity* 13:771-782.
26. Lollini, P. L., C. de Giovanni, V. Eusebi, G. Nicoletti, G. Prodi, and P. Nanni. 1984. High-metastatic clones selected in vitro from a recent spontaneous BALB/c mammary adenocarcinoma cell line. *Clin Exp Metastasis* 2:251-259.
27. Verzeletti, S., C. Bonini, S. Marktel, N. Nobili, F. Ciceri, C. Traversari, and C. Bordignon. 1998. Herpes simplex virus thymidine kinase gene transfer for controlled graft-versus-host disease and graft-versus-leukemia: clinical follow-up and improved new vectors. *Hum Gene Ther* 9:2243-2251.
28. Bondanza, A., V. Valtolina, Z. Magnani, M. Ponzoni, K. Fleischhauer, M. Bonyhadi, C. Traversari, F. Sanvito, S. Toma, M. Radrizzani, S. La Seta-Catamancio, F. Ciceri, C. Bordignon, and C. Bonini. 2005. Suicide gene therapy of graft-versus-host disease induced by central memory human T lymphocytes. *Blood*
29. Stetson, D. B., M. Mohrs, V. Mallet-Designe, L. Teyton, and R. M. Locksley. 2002. Rapid expansion and IL-4 expression by *Leishmania*-specific naive helper T cells in vivo. *Immunity* 17:191-200.
30. Iezzi, G., K. Karjalainen, and A. Lanzavecchia. 1998. The duration of antigenic stimulation determines the fate of naive and effector T cells. *Immunity* 8:89-95.
31. Gett, A. V., F. Sallusto, A. Lanzavecchia, and J. Geginat. 2003. T cell fitness determined by signal strength. *Nat Immunol* 4:355-360.
32. Harari, A., S. Petitpierre, F. Vallelian, and G. Pantaleo. 2004. Skewed representation of functionally distinct populations of virus-specific CD4 T cells in HIV-1-infected subjects with progressive disease: changes after antiretroviral therapy. *Blood* 103:966-972.
33. Harari, A., F. Vallelian, P. R. Meylan, and G. Pantaleo. 2005. Functional heterogeneity of memory CD4 T cell responses in different conditions of antigen exposure and persistence. *J Immunol* 174:1037-1045.
34. Jackson, H. M., N. Dimopoulos, Q. Chen, T. Luke, T. Yee Tai, E. Maraskovsky, L. J. Old, I. D. Davis, J. Cebon, and W. Chen. 2004. A robust human T-cell culture method suitable for monitoring CD8+ and CD4$^+$ T-cell responses from cancer clinical trial samples. *J Immunol Methods* 291:51-62.
35. Unutmaz, D., F. Baldoni, and S. Abrignani. 1995. Human naive T cells activated by cytokines differentiate into a split phenotype with functional features intermediate between naive and memory T cells. *Int Immunol* 7:1417-1424.
36. Unutmaz, D., P. Pileri, and S. Abrignani. 1994. Antigen-independent activation of naive and memory resting T cells by a cytokine combination. *J Exp Med* 180:1159-1164.
37. Dudley, M. E., J. R. Wunderlich, T. E. Shelton, J. Even, and S. A. Rosenberg. 2003. Generation of tumor-infiltrating lymphocyte cultures for use in adoptive transfer therapy for melanoma patients. *J Immunother* 26:332-342.
38. Hassan, J., and D. J. Reen. 1998. IL-7 promotes the survival and maturation but not differentiation of human post-thymic CD4$^+$ T cells. *Eur J Immunol* 28:3057-3065.
39. Reinhardt, R. L., A. Khoruts, R. Merica, T. Zell, and M. K. Jenkins. 2001. Visualizing the generation of memory CD4 T cells in the whole body. *Nature* 410:101-105.
40. Roman, E., E. Miller, A. Harmsen, J. Wiley, U. H. Von Andrian, G. Huston, and S. L. Swain. 2002. CD4 effector T cell subsets in the response to influenza: heterogeneity, migration, and function. *J Exp Med* 196:957-968.
41. Sallusto, F., J. Geginat, and A. Lanzavecchia. 2004. Central memory and effector memory T cell subsets: function, generation, and maintenance. *Annu Rev Immunol* 22:745-763.
42. Park, J. H., Q. Yu, B. Erman, J. S. Appelbaum, D. Montoya-Durango, H. L. Grimes, and A. Singer. 2004. Suppression of IL7Ralpha transcription by IL-7 and other prosurvival cytokines: a novel mechanism for maximizing IL-7-dependent T cell survival. *Immunity* 21:289-302.
43. Scarpellini, P., S. Tasca, L. Galli, A. Beretta, A. Lazzarin, and C. Fortis. 2004. Selected pool of peptides from ESAT-6 and CFP-10 proteins for detection of *Mycobacterium tuberculosis* infection. *J Clin Microbiol* 42:3469-3474.

The invention claimed is:

1. A method of treating cancer, comprising administering a genetically modified T cell population, that is CD4+ or CD8+, to a patient in need thereof, the genetically modified T cell population, that is CD4+ or CD8+, having been prepared by the steps comprising:
   a) activating lymphocytes in vitro in a cell-free medium with at least two specific activating receptor agonist antibodies that are able to drive lymphocyte activation, wherein one of the lymphocyte activating receptor agonist antibodies is specific for CD3 polypeptide and the other lymphocyte activating receptor agonist antibody is specific for CD28;
   b) exposing activated lymphocytes in vitro, in a cell-free medium, to an effective amount of interleukin added to the medium, wherein the interleukin is at least IL-7 and IL-15, able to selectively expand populations of memory T cells; and
   c) inserting and expressing an exogenous gene by means of an appropriate vector into the lymphocytes as obtained in b) to produce a genetically modified memory T cell population that is CD4+ or CD8+;
   wherein the effective amount of the interleukin added to the medium is from 5 ng/ml to 50 ng/ml;
   wherein the medium and interleukin of step b) are replaced every 3 to 4 days; and
   wherein about 80% of both CD8+ and CD4+ T– cells of steps b) and c) are positive for the marker CD62L and marker CD127 and are central memory T-lymphocytes.

2. The method of claim 1 wherein the lymphocytes of step (a) are derived from a biological sample selected from the group consisting of: blood and other liquid samples of biological origin, solid tissue samples, tissue cultures of cells derived therefrom and the progeny thereof, isolated cells from biological samples.

3. The method of claim 1, wherein the specific lymphocyte activating receptor agonist of step (a) is conjugated to cell-mimicking cell-free supports.

4. The method of claim 3, wherein the cell-mimicking supports are paramagnetic beads.

5. The method of claim 1, wherein the vector of step (c) is a viral vector.

6. The method of claim 1, wherein the exogenous gene of step (c) comprises a gene selected from the group consisting of a suicide gene, a marker gene, a biologically active molecule, a receptor, a soluble factor retained in the cell or released outside the cell, a gene conferring resistance to a prodrug and combinations thereof.

7. The method of claim 1, wherein the effective amount of the interleukin added to the medium is 5 ng/ml or 50 ng/ml.

8. The method of claim 1, wherein the cancer is an adenocarcinoma.

9. The method of claim 8, wherein the cancer is a mammary adenocarcinoma.

* * * * *